(12) United States Patent
Angermann et al.

(10) Patent No.: US 8,835,657 B2
(45) Date of Patent: Sep. 16, 2014

(54) CYCLOPENTANEDIONE COMPOUNDS AND THEIR USE AS INSECTICIDES, ACARICIDES AND/OR FUNGICIDES

(75) Inventors: Alfred Angermann, Kriftel (DE); Reiner Fischer, Monheim (DE); Stefan Lehr, Liederbach (DE); Arnd Voerste, Köln (DE)

(73) Assignee: Bayer CropScience AG, Monheim (DE)

( * ) Notice: Subject to any disclaimer, the term of this patent is extended or adjusted under 35 U.S.C. 154(b) by 226 days.

(21) Appl. No.: 13/319,035

(22) PCT Filed: Apr. 28, 2010

(86) PCT No.: PCT/EP2010/002609
§ 371 (c)(1),
(2), (4) Date: Jan. 30, 2012

(87) PCT Pub. No.: WO2010/127797
PCT Pub. Date: Nov. 11, 2010

(65) Prior Publication Data
US 2012/0123129 A1   May 17, 2012

(30) Foreign Application Priority Data
May 6, 2009 (EP) .................................. 09159547

(51) Int. Cl.
*C07D 307/93* (2006.01)
*A01N 43/90* (2006.01)
(52) U.S. Cl.
CPC ..................................... A01N 43/90 (2013.01)
USPC ....................................................... 549/459
(58) Field of Classification Search
CPC ...................................................... A01N 43/90
USPC ....................................................... 549/459
See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,761,373 A | 8/1988 | Anderson et al. | |
| 4,808,430 A | 2/1989 | Kouno | |
| 5,013,659 A | 5/1991 | Bedbrook et al. | |
| 5,084,082 A | 1/1992 | Sebastian | |
| 5,141,870 A | 8/1992 | Bedbrook et al. | |
| 5,198,599 A | 3/1993 | Thill | |
| 5,273,894 A | 12/1993 | Strauch et al. | |
| 5,276,268 A | 1/1994 | Strauch et al. | |
| 5,304,732 A | 4/1994 | Anderson et al. | |
| 5,331,107 A | 7/1994 | Anderson et al. | |
| 5,378,824 A | 1/1995 | Bedbrook et al. | |
| 5,434,283 A | 7/1995 | Wong et al. | |
| 5,463,175 A | 10/1995 | Barry et al. | |
| 5,561,236 A | 10/1996 | Leemans et al. | |
| 5,605,011 A | 2/1997 | Bedbrook et al. | |
| 5,637,489 A | 6/1997 | Strauch et al. | |
| 5,646,024 A | 7/1997 | Leemans et al. | |
| 5,648,477 A | 7/1997 | Leemans et al. | |
| 5,712,107 A | 1/1998 | Nichols | |
| 5,731,180 A | 3/1998 | Dietrich | |
| 5,739,082 A | 4/1998 | Donn | |
| 5,767,361 A | 6/1998 | Dietrich | |
| 5,773,702 A | 6/1998 | Penner et al. | |
| 5,776,760 A | 7/1998 | Barry et al. | |
| 5,789,566 A | 8/1998 | Bonhomme et al. | |
| 5,808,135 A | 9/1998 | Fischer et al. | |
| 5,824,790 A | 10/1998 | Keeling et al. | |
| 5,840,946 A | 11/1998 | Wong et al. | |
| 5,866,782 A | 2/1999 | Iwabuchi et al. | |
| 5,876,739 A | 3/1999 | Turnblad et al. | |
| 5,908,810 A | 6/1999 | Donn | |
| 5,908,975 A | 6/1999 | Caimi et al. | |
| 5,928,937 A | 7/1999 | Kakefuda et al. | |
| 5,965,755 A | 10/1999 | Sernyk et al. | |
| 5,969,169 A | 10/1999 | Fan | |

(Continued)

FOREIGN PATENT DOCUMENTS

| | | | |
|---|---|---|---|
| GB | WO 2009019015 | * 2/2009 | .......... C07D 493/04 |
| JP | 2006-304779 A | 11/2006 | |

(Continued)

OTHER PUBLICATIONS

Barry, G., et al., "Inhibitors of Amino Acid Biosynthesis: Strategies for Imparting Glyphosate Tolerance to Crop Plants," *Current Topics in Plant Pathology* 7:139-145, American Society of Plant Physiologists, United States (1992).

Comai, L., et al., "An Altered aroA Gene Product Confers Resistance to the Herbicide Glyphosate," *Science* 221:370-371, American Association for the Advancement of Science, United States (1983).

Crickmore, N., et al., "Revision of the Nomenclature for the *Bacillus thuringiensis* Pesticidal Crystal Proteins," *Microbiology and Molecular Biology Reviews* 62(3):807-813, American Society for Microbiology, United States (1998).

(Continued)

*Primary Examiner* — Nizal Chandrakumar
(74) *Attorney, Agent, or Firm* — Sterne, Kessler, Goldstein & Fox P.L.L.C.

(57) ABSTRACT

The present invention relates to the use of compounds of Formula (I)

(I)

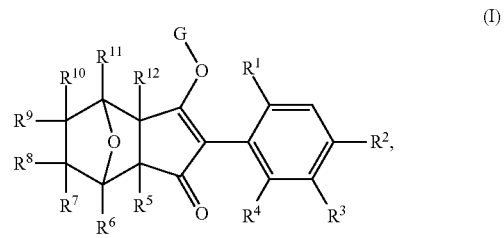

wherein
$R^1, R^2, R^3, R^4, R^5, R^6, R^7, R^8, R^9, R^{10}, R^{11}, R^{12}$ and G have the meanings given above as insecticides and/or acaricides and/or fungicides.

10 Claims, No Drawings

(56) References Cited

U.S. PATENT DOCUMENTS

| | | | |
|---|---|---|---|
| 6,013,861 A | 1/2000 | Bird et al. |
| 6,063,947 A | 5/2000 | DeBonte et al. |
| 6,130,367 A | 10/2000 | Kossmann et al. |
| 6,162,966 A | 12/2000 | Kossmann et al. |
| 6,169,190 B1 | 1/2001 | Lanuza et al. |
| 6,207,880 B1 | 3/2001 | Kossmann et al. |
| 6,211,436 B1 | 4/2001 | Kossmann et al. |
| 6,229,072 B1 | 5/2001 | Burns et al. |
| 6,245,968 B1 | 6/2001 | Boudec et al. |
| 6,255,561 B1 | 7/2001 | Kossman et al. |
| 6,255,563 B1 | 7/2001 | Emmermann et al. |
| 6,268,549 B1 | 7/2001 | Sailland et al. |
| 6,270,828 B1 | 8/2001 | DeBonte et al. |
| 6,284,479 B1 | 9/2001 | Nichols |
| 6,307,124 B1 | 10/2001 | Kossmann et al. |
| 6,323,392 B1 | 11/2001 | Charne |
| 6,566,585 B1 | 5/2003 | Quanz |
| 6,566,587 B1 | 5/2003 | Lebrun et al. |
| 6,590,141 B1 | 7/2003 | Frohberg |
| 6,596,928 B1 | 7/2003 | Landschütze |
| 6,642,180 B1 | 11/2003 | Fischer et al. |
| 6,699,694 B1 | 3/2004 | Buttcher et al. |
| 6,734,341 B2 | 5/2004 | Singletary et al. |
| 6,791,010 B1 | 9/2004 | Frohberg |
| 6,812,010 B1 | 11/2004 | Derose et al. |
| 6,890,732 B1 | 5/2005 | Loerz et al. |
| 6,891,088 B1 | 5/2005 | Neuhaus et al. |
| 6,951,969 B1 | 10/2005 | Loerz et al. |
| 7,112,665 B1 | 9/2006 | Leemans et al. |
| 7,304,209 B2 | 12/2007 | Zink et al. |
| 2002/0031826 A1 | 3/2002 | Nichols |
| 2003/0073851 A1 | 4/2003 | Lieb et al. |
| 2003/0176428 A1 | 9/2003 | Schneidersmann et al. |
| 2003/0216260 A1 | 11/2003 | Ruther et al. |
| 2005/0257283 A1 | 11/2005 | Matringe et al. |
| 2006/0015966 A1 | 1/2006 | Landschutze |
| 2006/0058194 A1 | 3/2006 | Fischer et al. |
| 2006/0122061 A1 | 6/2006 | Lieb et al. |
| 2006/0166829 A1 | 7/2006 | Fischer et al. |
| 2006/0168690 A1 | 7/2006 | Shibatani et al. |
| 2008/0250533 A1 | 10/2008 | Frohberg |
| 2012/0142529 A1* | 6/2012 | Tyte et al. ................ 504/103 |

FOREIGN PATENT DOCUMENTS

| | | |
|---|---|---|
| WO | WO 89/10396 A1 | 11/1989 |
| WO | WO 91/02069 A1 | 2/1991 |
| WO | WO 92/14827 A1 | 9/1992 |
| WO | WO 94/04692 A1 | 3/1994 |
| WO | WO 94/04693 A2 | 3/1994 |
| WO | WO 94/09144 A1 | 4/1994 |
| WO | WO 94/11520 A2 | 5/1994 |
| WO | WO 94/21795 A1 | 9/1994 |
| WO | WO 95/04826 A1 | 2/1995 |
| WO | WO 95/07355 A1 | 3/1995 |
| WO | WO 95/13389 A1 | 5/1995 |
| WO | WO 95/26407 A1 | 10/1995 |
| WO | WO 95/31553 A1 | 11/1995 |
| WO | WO 95/35026 A1 | 12/1995 |
| WO | WO 96/01904 A1 | 1/1996 |
| WO | WO 96/19581 A1 | 6/1996 |
| WO | WO 96/21023 A1 | 7/1996 |
| WO | WO 96/33270 A1 | 10/1996 |
| WO | WO 96/34968 A2 | 11/1996 |
| WO | WO 97/20936 A1 | 6/1997 |
| WO | WO 97/41218 A1 | 11/1997 |
| WO | WO 97/45545 A1 | 12/1997 |
| WO | WO 97/47806 A1 | 12/1997 |
| WO | WO 97/47807 A1 | 12/1997 |
| WO | WO 97/47808 A1 | 12/1997 |
| WO | WO 98/00549 A1 | 1/1998 |
| WO | WO 98/20145 A2 | 5/1998 |
| WO | WO 98/22604 A1 | 5/1998 |
| WO | WO 98/27212 A1 | 6/1998 |
| WO | WO 98/27806 A1 | 7/1998 |
| WO | WO 98/32326 A2 | 7/1998 |
| WO | WO 98/39460 A1 | 9/1998 |
| WO | WO 98/40503 A1 | 9/1998 |
| WO | WO 99/12950 A2 | 3/1999 |
| WO | WO 99/24593 A1 | 5/1999 |
| WO | WO 99/53072 A1 | 10/1999 |
| WO | WO 99/57965 A1 | 11/1999 |
| WO | WO 99/66050 A1 | 12/1999 |
| WO | WO 00/04173 A1 | 1/2000 |
| WO | WO 00/11192 A2 | 3/2000 |
| WO | WO 00/14249 A1 | 3/2000 |
| WO | WO 00/28052 A2 | 5/2000 |
| WO | WO 00/47727 A2 | 8/2000 |
| WO | WO 00/66746 A1 | 11/2000 |
| WO | WO 00/66747 A1 | 11/2000 |
| WO | WO 00/77229 A2 | 12/2000 |
| WO | WO 01/14569 A2 | 3/2001 |
| WO | WO 01/17333 A1 | 3/2001 |
| WO | WO 01/19975 A2 | 3/2001 |
| WO | WO 01/24615 A1 | 4/2001 |
| WO | WO 01/65922 A2 | 9/2001 |
| WO | WO 01/66704 A2 | 9/2001 |
| WO | WO 01/98509 A2 | 12/2001 |
| WO | WO 02/26995 A1 | 4/2002 |
| WO | WO 02/28186 A2 | 4/2002 |
| WO | WO 02/34923 A2 | 5/2002 |
| WO | WO 02/36782 A2 | 5/2002 |
| WO | WO 02/45485 A1 | 6/2002 |
| WO | WO 02/079410 A2 | 10/2002 |
| WO | WO 02/080675 A1 | 10/2002 |
| WO | WO 02/101059 A2 | 12/2002 |
| WO | WO 03/013226 A2 | 2/2003 |
| WO | WO 03/033540 A2 | 4/2003 |
| WO | WO 03/059065 A1 | 7/2003 |
| WO | WO 03/071860 A2 | 9/2003 |
| WO | WO 03/092360 A2 | 11/2003 |
| WO | WO 2004/040012 A2 | 5/2004 |
| WO | WO 2004/053219 A2 | 6/2004 |
| WO | WO 2004/056999 A1 | 7/2004 |
| WO | WO 2004/078983 A2 | 9/2004 |
| WO | WO 2004/090140 A2 | 10/2004 |
| WO | WO 2004/106529 A2 | 12/2004 |
| WO | WO 2005/002324 A1 | 1/2005 |
| WO | WO 2005/002359 A1 | 1/2005 |
| WO | WO 2005/012515 A2 | 2/2005 |
| WO | WO 2005/017157 A1 | 2/2005 |
| WO | WO 2005/020673 A1 | 3/2005 |
| WO | WO 2005/030941 A1 | 4/2005 |
| WO | WO 2005/030942 A1 | 4/2005 |
| WO | WO 2005/093093 A2 | 10/2005 |
| WO | WO 2005/095617 A2 | 10/2005 |
| WO | WO 2005/095618 A2 | 10/2005 |
| WO | WO 2005/095619 A1 | 10/2005 |
| WO | WO 2005/095632 A2 | 10/2005 |
| WO | WO 2005/123927 A1 | 12/2005 |
| WO | WO 2006/007373 A2 | 1/2006 |
| WO | WO 2006/015376 A2 | 2/2006 |
| WO | WO 2006/018319 A1 | 2/2006 |
| WO | WO 2006/021972 A1 | 3/2006 |
| WO | WO 2006/024351 A1 | 3/2006 |
| WO | WO 2006/032469 A2 | 3/2006 |
| WO | WO 2006/032538 A1 | 3/2006 |
| WO | WO 2006/045633 A1 | 5/2006 |
| WO | WO 2006/060634 A2 | 6/2006 |
| WO | WO 2006/063862 A1 | 6/2006 |
| WO | WO 2006/072603 A2 | 7/2006 |
| WO | WO 2006/103107 A1 | 10/2006 |
| WO | WO 2006/108702 A1 | 10/2006 |
| WO | WO 2006/133827 A2 | 12/2006 |
| WO | WO 2006/136351 A2 | 12/2006 |
| WO | WO 2007/009823 A1 | 1/2007 |
| WO | WO 2007/024782 A2 | 3/2007 |
| WO | WO 2007/027777 A2 | 3/2007 |
| WO | WO 2007/039314 A2 | 4/2007 |
| WO | WO 2007/039316 A1 | 4/2007 |
| WO | WO 2007/107326 A1 | 9/2007 |
| WO | WO 2007/131699 A2 | 11/2007 |
| WO | WO 2008/017518 A1 | 2/2008 |

(56) References Cited

FOREIGN PATENT DOCUMENTS

| WO | WO 2008/080630 A1 | 7/2008 |
|----|-------------------|--------|
| WO | WO 2008/080631 A1 | 7/2008 |
| WO | WO 2008/090008 A1 | 7/2008 |
| WO | WO 2009/019015 A1 | 2/2009 |

OTHER PUBLICATIONS

Draber, W., "Chemie der Pflanzenschutz-und Schactlingsbekampfungsmittel [Chemistry of Plant Protection and Pest Control Agents]," R. Wegler ed. 2:401-412, Springer-Verlag, Berlin, Germany (1970).

English language translation of Draber, W., "Chemie der Pflanzenschutz-und Schadlingsbekampfungsmittel [Chemistry of Plant Protection and Pest Control Agents]," R. Wegler ed. 2:1-15, Springer-Verlag, Berlin, Germany (1970).

Gasser, C.S., et al., "Structure, Expression, and Evolution of the 5-Enolpyruvylshikimate-3-phosohate Synthase Genes of Petunia and Tomato," *The Journal of Biological Chemistry* 263(9):4280-4289, American Society for Biochemistry and Molecular Biology, Inc., United States (1988).

Moellenbeck, D.J., et al., "Insecticidal proteins from *Bacillus thuringiensis* protect corn from corn rootworms," *Nature Biotechnology* 19:668-672, Nature Publishing Group, United States (2001).

Schnepf, H.E., et al., "Characterization of Cry34/Cry35 Binary insecticidal Proteins from Diverse *Bacillus thuringlensis* Strain Collections," *Applied and Environmental Microbiology* 71(4):1765-1774, American Society for Microbiology, United States (2005).

Shah, D.M., et al., "Engineering Herbicide Tolerance in Transgenic Plants," *Science* 233:478-481, American Association for the Advancement of Science, United States (1986).

Tranel, P.J. and Wright, T.R., "Resistance of weeds to ALS-inhibiting herbicides: what have we learned?," *Weed Science* 50:700-712, Weed Science Society of America, United States (2002).

English language Abstract of Japanese Patent Publication No. 2006-304779 A, Japanese Patent Office, Patent & Utility Model Gazette DB, Patent Abstracts of Japan (2006).

English language Abstract of International Patent Publication No. WO 01/14569 A2, European Patent Office, espacenet database—Worldwide Database (2001).

English language Abstract of International Patent Publication No. WO 99/57965 A1, European Patent Office, espacenet database—Worldwide Database (1999).

International Search Report for International Application No. PCT/EP2010/002609, European Patent Office, The Hague, Netherlands, mailed on Feb. 22, 2011.

* cited by examiner

CYCLOPENTANEDIONE COMPOUNDS AND THEIR USE AS INSECTICIDES, ACARICIDES AND/OR FUNGICIDES

The present invention relates to the use of cyclopentanedione compounds, and derivatives thereof as insecticides, acaricides and/or fungicides.

Cyclopentanedione compounds having herbicidal action are described, for example, in WO 01/74770, WO 96/03366 and WO 2009/019015.

Cyclopentanedione compounds having insecticidal and/or acaricidal and/or fungicidal properties have now been found.

The present invention accordingly relates to the use of compounds of formula I

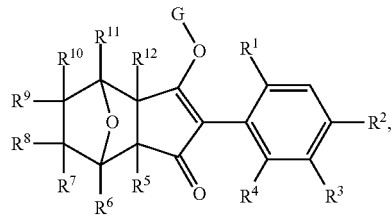

(I)

wherein $R^1$ is methyl, ethyl, n-propyl, isopropyl, halomethyl, haloethyl, halogen, vinyl, ethynyl, methoxy, ethoxy, halomethoxy, haloethoxy or cyclopropyl, $R^2$ and $R^3$ are independently of each other hydrogen, halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$haloalkenyl, $C_2$-$C_6$alkynyl, $C_3$-$C_6$alkenyloxy, $C_3$-$C_6$haloalkenyloxy, $C_3$-$C_6$alkynyloxy, $C_3$-$C_6$cycloalkyl, $C_1$-$C_6$alkylthio, $C_1$-$C_6$alkylsulfinyl, $C_1$-$C_6$alkylsulfonyl, $C_1$-$C_6$alkoxysulfonyl, $C_1$-$C_6$haloalkoxysulfonyl, cyano, nitro, optionally substituted aryl or optionally substituted heteroaryl, where at least one of $R^2$ and $R^3$ is optionally substituted aryl or optionally substituted heteroaryl, $R^4$ is hydrogen, methyl, ethyl, n-propyl, isopropyl, halomethyl, haloethyl, halogen, vinyl, ethynyl, methoxy, ethoxy, halomethoxy or haloethoxy, $R^5$ and $R^{12}$ are independently of each other hydrogen, $C_1$-$C_3$alkyl, $C_1$-$C_3$haloalkyl, $C_1$-$C_3$alkoxy, $C_1$-$C_3$alkylthio, halogen or $C_1$-$C_6$alkoxycarbonyl, or $R^5$ and $R^{12}$ join together to form a 3-7 membered carbocyclic ring, optionally containing an oxygen or sulfur atom, and $R^6$, $R^7$, $R^8$, $R^9$, $R^{10}$ and $R^{11}$ are independently of each other hydrogen or a substituent, or $R^7$ and $R^8$ or $R^9$ and $R^{10}$, together with the carbon atoms to which they are attached form a keto, or optionally substituted imino or optionally substituted alkenyl unit, or any two of $R^7$, $R^8$, $R^9$ and $R^{10}$ together form a 3-8 membered carbocyclic ring optionally containing a heteroatom selected from O, S or N and optionally substituted, or $R^7$ and $R^{10}$ together form a bond, and G represents hydrogen (a) or represents one of the groups

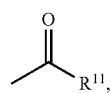

(b)

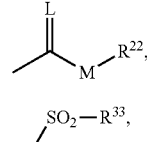

(c)

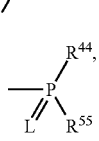

(d)

(e)

E or (f)

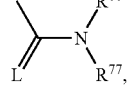

(g)

in which

E represents a metal ion or an ammonium ion,

L represents oxygen or sulphur and

M represents oxygen or sulphur, $R^{11}$ represents in each case optionally halogen- or cyano-substituted $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl or poly-$C_1$-$C_8$-alkoxy-$C_1$-$C_8$-alkyl or represents optionally halogen-, $C_1$-$C_6$-alkyl- or $C_1$-$C_6$-alkoxy-substituted $C_3$-$C_8$-cycloalkyl in which optionally one or two not directly adjacent methylene groups are replaced by oxygen and/or sulphur, represents optionally halogen-, cyano-, nitro-, $C_1$-$C_6$-alkyl-, $C_1$-$C_6$-alkoxy-, $C_1$-$C_6$-haloalkyl-, $C_1$-$C_6$-haloalkoxy-, $C_1$-$C_6$-alkylthio- or $C_1$-$C_6$-alkylsulphonyl-substituted phenyl, represents optionally halogen-, nitro-, cyano-, $C_1$-$C_6$-alkyl-, $C_1$-$C_6$-alkoxy-, $C_1$-$C_6$-haloalkyl- or $C_1$-$C_6$-haloalkoxy-substituted phenyl-$C_1$-$C_6$-alkyl, represents optionally halogen- or $C_1$-$C_6$-alkyl-substituted 5- or 6-membered hetaryl having one or two heteroatoms from the group consisting of oxygen, sulphur and nitrogen, represents optionally halogen- or $C_1$-$C_6$-alkyl-substituted phenoxy-$C_1$-$C_6$-alkyl or represents optionally halogen-, amino- or $C_1$-$C_6$-alkyl-substituted 5- or 6-membered hetaryloxy-$C_1$-$C_6$-alkyl having one or two heteroatoms from the group consisting of oxygen, sulphur and nitrogen, $R^{22}$ represents in each case optionally halogen- or cyano-substituted $C_1$-$C_{20}$-alkyl, $C_2$-$C_{20}$-alkenyl, $C_1$-$C_8$-alkoxy-$C_2$-$C_8$-alkyl or poly-$C_1$-$C_3$-alkoxy-$C_2$-$C_8$-alkyl, represents optionally halogen-, $C_1$-$C_6$-alkyl- or $C_1$-$C_6$-alkoxy-substituted $C_3$-$C_8$-cycloalkyl or represents in each case optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl, $R^{33}$ represents optionally halogen-substituted $C_1$-$C_8$-alkyl or in each case optionally halogen-, $C_1$-$C_6$-alkyl-, $C_1$-$C_6$-alkoxy-, $C_1$-$C_4$-haloalkoxy-, cyano- or nitro-substituted phenyl or benzyl, $R^{44}$ and $R^{55}$ independently of one another represent in each case optionally halogen-substituted $C_1$-$C_8$-alkyl, $C_1$-$C_8$-alkoxy, $C_1$-$C_8$-alkylamino, di($C_1$-$C_8$-alkyl)amino, $C_1$-$C_8$-alkylthio or $C_3$-$C_8$-alkenylthio or represent in each case optionally halogen-, nitro-, cyano-, $C_1$-$C_4$-alkoxy-, $C_1$-$C_4$-haloalkoxy-, $C_1$-$C_4$-haloalkylthio-, $C_1$-$C_4$-alkyl- or $C_1$-$C_4$-haloalkyl-substituted phenyl, phenoxy or phenylthio, $R^{66}$ and $R^{77}$ independently of one another represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl or together represent an optionally $C_1$-$C_6$-alkyl-substituted $C_3$-$C_6$-alkylene radical in which optionally one methylene group is replaced by oxygen or sulphur as insecticides, acaricides and/or fungicides.

In the substituent definitions of the compounds of the formula I, each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, isopropyl, n-butyl, sec-butyl, isobutyl, tert-butyl or neopentyl. The alkyl groups are suitably $C_1$ to $C_6$ alkyl groups, but are preferably $C_1$-$C_4$ alkyl and, more preferably, $C_1$-$C_2$ alkyl groups.

Alkenyl and alkynyl moieties can be in the form of straight or branched chains, and the alkenyl moieties, where appropriate, can be of either the (E)- or (Z)-configuration. Examples are vinyl, allyl and propargyl. Alkenyl and alkynyl moieties can contain one or more double and/or triple bonds in any combination. It is understood, that allenyl and alkylinylalkenyl are included in these terms.

Halogen is fluorine, chlorine, bromine or iodine.

Haloalkyl groups are alkyl groups which are substituted with one or more of the same or different halogen atoms and are, for example, $CF_3$, $CF_2Cl$, $CF_2H$, $CCl_2H$, $FCH_2$, $ClCH_2$, $BrCH_2$, $CH_3CHF$, $(CH_3)_2CF$, $CF_3CH_2$ or $CHF_2CH_2$.

In the context of the present specification the term "aryl" preferably refers to phenyl and naphthyl. The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulphur. Examples of such groups include furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl. Preferred examples of heteroaromatic radicals include pyridyl, pyrimidinyl, triazinyl, thienyl, furyl, oxazolyl, isoxazolyl, 2,1,3-benzoxadiazolyl and thiazolyl.

Cycloalkyl includes preferably cyclopropyl, cyclobutyl, cyclopentyl and cyclohexyl. Cycloalkylalkyl is preferentially cyclopropylmethyl. Cycloalkenyl includes cyclopentenyl and cyclohexenyl.

Carbocyclic rings such as those formed together by any two of $R^7$, $R^8$, $R^9$ and $R^{10}$ include cycloalkyl and cycloalkenyl groups with up to 7 atoms, optionally including one or more, preferably 1 or 2 heteroatoms selected from O, S and N leading to heterocycles such as 1,3-dioxolane, oxetane, tetrahydrofuran, morpholine, thiomorpholine and piperazine.

When present, the optional substituents on aryl, heteroaryl, cycloalkyl or heterocyclyl are selected independently, from halogen, nitro, cyano, rhodano, isothiocyanato, $C_{1-6}$ alkyl, $C_{1-6}$ haloalkyl, $C_{1-6}$ alkoxy-($C_{1-6}$)alkyl, $C_{2-6}$ alkenyl, $C_{2-6}$ haloalkenyl, $C_{2-6}$ alkynyl, $C_{3-7}$ cycloalkyl (itself optionally substituted with $C_{1-6}$ alkyl or halogen), $C_{5-7}$ cycloalkenyl (itself optionally substituted with $C_{1-6}$ alkyl or halogen), hydroxy, $C_{1-10}$ alkoxy, $C_{1-10}$alkoxy($C_{1-10}$)alkoxy, tri($C_{1-4}$) alkylsilyl($C_{1-6}$)alkoxy, $C_{1-6}$ alkoxycarbonyl($C_{1-10}$)alkoxy, $C_{1-10}$ haloalkoxy, aryl($C_{1-4}$)alkoxy (where the aryl group is optionally substituted with halogen or $C_{1-6}$ alkyl), $C_{3-7}$ cycloalkyloxy (where the cycloalkyl group is optionally substituted with $C_{1-6}$ alkyl or halogen), $C_{3-10}$ alkenyloxy, $C_{3-10}$ alkynyloxy, mercapto, $C_{1-10}$ alkylthio, $C_{1-10}$ haloalkylthio, aryl($C_{1-4}$)alkylthio, $C_{3-7}$ cycloalkylthio (where the cycloalkyl group is optionally substituted with $C_{1-6}$ alkyl or halogen), tri($C_{1-4}$)-alkylsilyl($C_{1-6}$)-alkylthio, arylthio, $C_{1-6}$ alkylsulfonyl, $C_{1-6}$ haloalkylsulfonyl, $C_{1-6}$ alkylsulfinyl, $C_{1-6}$ haloalkylsulfinyl, arylsulfonyl, tri($C_{1-4}$)alkylsilyl, aryldi($C_{1-4}$)-alkylsilyl, ($C_{1-4}$)alkyldiarylsilyl, triarylsilyl, $C_{1-10}$ alkylcarbonyl, $HO_2C$, $C_{1-10}$ alkoxycarbonyl, aminocarbonyl, $C_{1-6}$ alkylaminocarbonyl, di($C_{1-6}$alkyl)-aminocarbonyl, N—($C_{1-3}$ alkyl)-N—($C_{1-3}$ alkoxy)aminocarbonyl, $C_{1-6}$ alkylcarbonyloxy, arylcarbonyloxy, di($C_{1-6}$)alkylamino-carbonyloxy, aryl (itself optionally substituted with $C_{1-6}$ alkyl or halogen), heteroaryl (itself optionally substituted with $C_{1-6}$ alkyl or halogen), heterocyclyl (itself optionally substituted with $C_{1-6}$ alkyl or halogen), aryloxy (where the aryl group is optionally substituted with $C_{1-6}$ alkyl or halogen), heteroaryloxy (where the heteroaryl group is optionally substituted with $C_{1-6}$ alkyl or halogen), heterocyclyloxy (where the heterocyclyl group is optionally substituted with $C_{1-6}$ alkyl or halogen), amino, $C_{1-6}$ alkylamino, di($C_{1-6}$)alkylamino, $C_{1-6}$ alkylcarbonylamino, N—($C_{1-6}$)alkylcarbonyl-N—($C_{1-6}$)alkylamino, arylcarbonyl, (where the aryl group is itself optionally substituted with halogen or $C_{1-6}$ alkyl) or two adjacent positions on an aryl or heteroaryl system may be cyclised to form a 5, 6 or 7 membered carbocyclic or heterocyclic ring, itself optionally substituted with halogen or $C_{1-6}$ alkyl. Further substituents for aryl or heteroaryl include arylcarbonylamino (where the aryl group is substituted by $C_{1-6}$ alkyl or halogen), ($C_{1-6}$) alkoxycarbonylamino ($C_{1-6}$)alkoxycarbonyl-N—($C_{1-6}$)alkylamino, aryloxycarbonylamino (where the aryl group is substituted by $C_{1-6}$ alkyl or halogen), aryloxycarbonyl-N—($C_{1-6}$)alkylamino, (where the aryl group is substituted by $C_{1-6}$ alkyl or halogen), arylsulphonylamino (where the aryl group is substituted by $C_{1-6}$ alkyl or halogen), arylsulphonyl-N—($C_{1-6}$)alkylamino (where the aryl group is substituted by $C_{1-6}$ alkyl or halogen), aryl-N—($C_{1-6}$)alkylamino (where the aryl group is substituted by $C_{1-6}$ alkyl or halogen), arylamino (where the aryl group is substituted by $C_{1-6}$ alkyl or halogen), heteroaryl amino (where the heteroaryl group is substituted by $C_{1-6}$ alkyl or halogen), heterocyclylamino (where the heterocyclyl group is substituted by $C_{1-6}$ alkyl or halogen), aminocarbonylamino, $C_{1-6}$ alkylaminocarbonylamino, di($C_{1-6}$) alkylaminocarbonylamino, arylaminocarbonylamino where the aryl group is substituted by $C_{1-4}$ alkyl or halogen), aryl-N—($C_{1-6}$)alkylamino-carbonylamino where the aryl group is substituted by $C_{1-6}$ alkyl or halogen), $C_{1-6}$ alkylaminocarbonyl-N—($C_{1-6}$)alkylamino, di($C_{1-6}$)alkylaminocarbonyl-N—($C_{1-6}$)alkylamino, arylaminocarbonyl-N—($C_{1-6}$)alkylamino where the aryl group is substituted by $C_{1-6}$ alkyl or halogen) and aryl-N—($C_{1-6}$)alkylaminocarbonyl-N—($C_{1-6}$)alkylamino where the aryl group is substituted by $C_{1-6}$ alkyl or halogen).

For substituted aryl moieties, heterocyclyl and heteroaryl groups it is particularly preferred that one or more substituents are independently selected from halogen, in particular chloro, cyano, $C_{1-6}$ alkyl, $C_{1-6}$ haloalkyl, $C_{1-6}$ alkoxy, $C_{1-6}$ haloalkoxy, $C_{1-6}$ alkylthio, $C_{1-6}$ alkylsulfinyl, $C_{1-6}$ alkylsulfonyl, nitro and cyano. It is to be understood that dialkylamino substituents include those where the dialkyl groups together with the N atom to which they are attached form a five, six or seven-membered heterocyclic ring which may contain one or two further heteroatoms selected from O, N or S and which is optionally substituted by one or two independently selected ($C_{1-6}$)alkyl groups. When heterocyclic rings are formed by joining two groups on an N atom, the resulting rings are suitably pyrrolidine, piperidine, thiomorpholine and morpholine each of which may be substituted by one or two independently selected ($C_{1-6}$) alkyl groups.

The invention relates also to the salts which the compounds of formula I are able to form with amines, alkali metal and alkaline earth metal bases or quaternary ammonium bases.

Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{16}$alkylamines, $C_1$-$C_4$hydroxyalkylamines and $C_2$-$C_4$-alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamlne, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula [N($R_a R_b R_c R_d$)]OH wherein $R_a$, $R_b$, $R_c$, and $R_d$ are each independently of the others $C_1$-$C_4$alkyl. Further suitable tetraalkylammonium bases with other anions can be obtained, for example, by anion exchange reactions.

The latentiating groups G are selected to allow their removal by one or a combination of biochemical, chemical or physical processes to afford compounds of formula I where G is H before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

Depending on the nature of the substituents G, $R^1$, $R^2$, $R^3$, $R^4$, $R^5$, $R^6$, $R^7$ and $R^8$, compounds of formula I may exist in different isomeric forms. When G is hydrogen, for example, compounds of formula I may exist in different tautomeric forms. Also, when substituents contain double bonds, cis- and trans-isomers can exist. This invention covers all such isomers and tautomers and mixtures thereof in all proportions. These isomers, too, are within the scope of the claimed compounds of the formula I.

In a preferred group of compounds of the formula I, $R^1$ is methyl, ethyl, vinyl, ethynyl, cyclopropyl, difluoromethoxy or trifluoromethoxy. More preferably, $R^1$ is methyl or ethyl.

Preferably, $R^2$ and $R^3$ are independently of each other hydrogen, optionally substituted phenyl, optionally substituted naphthyl or optionally substituted heteroaryl. More preferably, $R^2$ and $R^3$ are independently of each other hydrogen, phenyl or phenyl substituted by $C_1$-$C_2$ alkyl, $C_1$-$C_2$haloalkyl, $C_1$-$C_2$alkoxy, $C_1$-$C_2$haloalkoxy, fluoro, chloro, bromo or cyano, heteroaryl or heteroaryl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano.

It is particularly preferred, that $R^2$ is hydrogen and $R^3$ is phenyl or phenyl substituted by $C_1$-$C_2$ alkyl, $C_1$-$C_2$haloalkyl, $C_1$-$C_2$alkoxy, $C_1$-$C_2$haloalkoxy, fluoro, chloro, bromo or cyano, or that $R^2$ is phenyl or phenyl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano and $R^3$ is hydrogen.

Preference is given to those phenyl groups $R^2$ and $R^3$, which are substituted by fluoro, chloro, bromo, especially fluoro or chloro, in the 4-position.

Preferably, $R^4$ is hydrogen, methyl, ethyl, vinyl or ethynyl. More preferably, $R^4$ is hydrogen, methyl or ethyl.

In preferred compounds of the formula I $R^5$ and $R^{12}$ are independently of each other hydrogen or $C_1$-$C_3$alkyl, where, more preferably, $R^5$ and $R^{12}$ are hydrogen.

Preferably, in the compounds of the formula I, $R^6$ and $R^{11}$ are independently of each other hydrogen, halogen, formyl, cyano or nitro or $R^6$ and $R^{11}$ are independently of each other $C_1$-$C_6$alkyl, $C_2$-$C_6$alkenyl, $C_2$-$C_6$alkynyl, $C_1$-$C_6$alkoxy, $C_3$-$C_7$ cycloalkyl, $C_3$-$C_7$ cycloalkenyl, phenyl, heteroaryl or a 3-7 membered heterocyclyl, where all these substituents are optionally substituted, or $R^6$ and $R^{11}$ are independently of each other a group $COR^{13}$, $CO_2R^{14}$ or $CONR^{15}R^{16}$, $CR^{17}$=$NOR^{18}$, $CR^{19}$=$NNR^{20}R^{21}$, $NHR^{22}$, $NR^{22}R^{23}$ or $OR^{24}$ wherein $R^{13}$ is $C_1$-$C_6$ alkyl, $C_2$-$C_6$ alkenyl, $C_2$-$C_6$ alkynyl, $C_3$-$C_7$ cycloalkyl, $C_5$-$C_7$ cycloalkenyl, phenyl, heteroaryl or a 3-7 membered heterocyclyl, where all these substituents are optionally substituted, $R^{14}$ is hydrogen, $C_1$-$C_6$ alkyl, $C_3$-$C_6$alkenyl, $C_3$-$C_6$ alkynyl, $C_3$-$C_7$ cycloalkyl, $C_5$-$C_7$ cycloalkenyl, phenyl, heteroaryl or is 3-7 membered heterocyclyl, where all these substituents are optionally substituted, $R^{15}$ is hydrogen, $C_1$-$C_6$ alkyl, $C_3$-$C_6$alkenyl, $C_3$-$C_6$ alkynyl, $C_3$-$C_7$ cycloalkyl, $C_5$-$C_7$ cycloalkenyl, phenyl, heteroaryl or a 3-7 membered heterocyclyl, where all these substituents are optionally substituted, $R^{16}$ is hydrogen, $C_1$-$C_6$ alkyl, $C_3$-$C_6$ alkenyl, $C_1$-$C_6$ alkynyl, $C_1$-$C_6$ alkoxy, $C_1$-$C_6$haloalkoxy, $C_3$-$C_7$ cycloalkyl, $C_5$-$C_7$ cycloalkenyl, $C_1$-$C_6$ alkylsulfonyl, phenylsulfonyl, heteroarylsulfonyl, amino, $C_1$-$C_6$ alkylamino, di$C_1$-$C_6$ alkylamino, phenyl, heteroaryl or a 3-7 membered heterocyclyl, where all these substituents are optionally substituted, or $R^{15}$ and $R^{18}$ may be joined to form an optionally substituted 3-7 membered ring, optionally containing an oxygen, sulfur or nitrogen atom, $R^{17}$ and $R^{19}$ are independently of each other hydrogen, $C_1$-$C_3$ alkyl or $C_3$-$C_6$ cycloalkyl, $R^{18}$, $R^{20}$ and $R^{21}$ are independently of each other hydrogen, $C_1$-$C_6$ alkyl, $C_3$-$C_6$ alkenyl, $C_3$-$C_6$ alkynyl, $C_3$-$C_7$ cycloalkyl, $C_1$-$C_6$ alkylcarbonyl, $C_1$-$C_6$ alkoxycarbonyl, $C_1$-$C_6$ alkylthiocarbonyl, aminocarbonyl, $C_1$-$C_6$alkylaminocarbonyl, di$C_1$-$C_6$alkylaminocarbonyl, phenyl or heteroaryl, where all these substituents are optionally substituted, $R^2$ is $C_1$-$C_6$ alkylcarbonyl, $C_1$-$C_6$ alkoxycarbonyl, $C_1$-$C_6$alkylthiocarbonyl, $C_1$-$C_6$ alkylaminocarbonyl, di$C_1$-$C_6$alkylaminocarbonyl, $C_1$-$C_6$ alkylsulfonyl, phenylcarbonyl, phenoxycarbonyl, phenylaminocarbonyl, phenylthiocarbonyl, phenylsulfonyl, heteroarylcarbonyl, heteroaryloxycarbonyl, heteroarylaminocarbonyl, heteroarylthiocarbonyl or heteroarylsulfonyl, where all these substituents are optionally substituted, $R^3$ is $C_1$-$C_6$ alkyl, $C_3$-$C_6$alkenyl, $C_3$-$C_6$alkynyl, $C_3$-$C_7$ cycloalkyl, $C_1$-$C_6$alkylcarbonyl, $C_{1\text{-}6}$alkoxycarbonyl, $C_1$-$C_6$alkylthiocarbonyl, $C_1$-$C_6$alkylaminocarbonyl, di$C_1$-$C_6$alkylaminocarbonyl, $C_1$-$C_6$alkylsulfonyl, phenyl or heteroaryl, where all these substituents are optionally substituted, or $R^{22}$ and $R^{23}$ may be joined to form an optionally substituted 3-7 membered ring, optionally containing an oxygen, sulfur or nitrogen atom, where all these substituents are optionally substituted, and $R^{24}$ is $C_3$-$C_6$alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$ alkylthiocarbonyl, aminocarbonyl, $C_1$-$C_6$ alkylaminocarbonyl, di$C_1$-$C_6$ alkylaminocarbonyl, $C_1$-$C_6$ alkylsulfonyl, tri($C_1$-$C_6$alkyl)silyl, phenyl or heteroaryl, where all these substituents are optionally substituted.

More preferably, $R^6$ and $R^{11}$ are independently of each other hydrogen, halogen, cyano, optionally substituted $C_1$-$C_6$alkyl or a group $COR^{13}$, $CO_2R^{14}$ or $CONR^{15}R^{16}$, $CR^{17}=NOR^{18}$ or $CR^{19}=NNR^{20}R^{21}$, wherein $R^{13}$, $R^{14}$, $R^{15}$ and $R^{16}$ are $C_1$-$C_6$ alkyl, $R^{17}$ and $R^{19}$ are hydrogen or $C_1$-$C_3$ alkyl, $R^{18}$ is $C_1$-$C_3$ alkyl, and $R^{20}$ and $R^{21}$ are independently of each other hydrogen or $C_1$-$C_3$alkyl, where $R^6$ and $R^{11}$ being independently of each other hydrogen, methyl or methyl substituted by $C_1$-$C_3$ alkoxy is particularly preferred.

Preference is given to compounds of formula I wherein $R^7$, $R^8$, $R^9$ and $R^{10}$ are independently of each other hydrogen, halogen, hydroxyl, formyl, amino, cyano or nitro, or $R^7$, $R^8$, $R^9$ and $R^{10}$ are independently of each other $C_1$-$C_8$alkyl, $C_2$-$C_6$ alkenyl, $C_2$-$C_6$alkynyl, $C_1$-$C_6$ alkoxy, $C_1$-$C_6$ alkylthio, $C_1$-$C_6$ alkylsulfinyl, $C_1$-$C_6$alkylsulfonyl, $C_3$-$C_7$ cycloalkyl, $C_4$-$C_7$ cycloalkenyl, tri($C_1$-$C_6$ alkyl)silyl, phenyl, heteroaryl or a 3-7 membered heterocyclyl, where all these substituents are optionally substituted, or $R^7$, $R^8$, $R^9$ and $R^{10}$ are independently of each other a group $COR^{13}$, $CO_2R^{14}$ or $CONR^{15}R^{16}$, $CR^{17}=NOR^{18}$, $CR^{19}=NNR^{20}R^{21}$, $NR^{22}R^{23}$ or $OR^{24}$, wherein $R^{13}$ is $C_1$-$C_6$alkyl, $C_2$-$C_6$alkenyl, $C_2$-$C_6$ alkynyl, $C_3$-$C_7$ cycloalkyl, $C_5$-$C_7$ cycloalkenyl, phenyl, heteroaryl or a 3-7 membered heterocyclyl, where all these substituents are optionally substituted, $R^{14}$ is hydrogen, $C_1$-$C_6$alkyl, $C_3$-$C_6$ alkenyl, $C_3$-$C_6$alkynyl, $C_3$-$C_7$ cycloalkyl, $C_5$-$C_7$ cycloalkenyl, phenyl, heteroaryl or is 3-7 membered heterocyclyl, where all these substituents are optionally substituted, $R^{15}$ is hydrogen, $C_1$-$C_6$alkyl, $C_3$-$C_6$alkenyl, $C_3$-$C_6$alkynyl, $C_1$-$C_6$alkoxy, $C_1$-$C_7$haloalkoxy, $C_3$-$C_7$ cycloalkyl, $C_5$-$C_7$ cycloalkenyl, phenyl, heteroaryl or a 3-7 membered heterocyclyl, where all these substituents are optionally substituted, $R^{18}$ is hydrogen, $C_1$-$C_6$alkyl, $C_3$-$C_6$alkenyl, $C_3$-$C_6$alkynyl, $C_1$-$C_6$alkoxy, $C_1$-$C_6$haloalkoxy, $C_3$-$C_7$ cycloalkyl, $C_5$-$C_7$ cycloalkenyl, $C_1$-$C_6$alkylsulfonyl, amino, $C_1$-$C_6$alkylamino, di$C_1$-$C_6$alkylamino, phenyl, heteroaryl or a 3-7 membered heterocyclyl, where all these substituents are optionally substituted, or $R^{15}$ and $R^{16}$ may be joined to form an optionally substituted 3-7 membered ring, optionally containing an oxygen, sulfur or nitrogen atom, $R^{17}$ and $R^{19}$ are independently of each other hydrogen, $C_1$-$C_3$alkyl or $C_3$-$C_6$cycloalkyl, $R^{18}$, $R^{20}$ and $R^{21}$ are independently of each other hydrogen, $C_1$-$C_6$ alkyl, $C_3$-$C_6$ alkenyl, $C_3$-$C_6$ alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$alkylaminocarbonyl, di$C_1$-$C_6$ alkylaminocarbonyl, phenyl or heteroaryl, where all these substituents are optionally substituted, $R^{22}$ and $R^{23}$ are independently of each other $C_1$-$C_6$alkyl, $C_3$-$C_6$ alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$ alkylthiocarbonyl, $C_1$-$C_6$alkylaminocarbonyl, di$C_1$-$C_6$ alkylaminocarbonyl, $C_1$-$C_6$ alkylsulfonyl, phenyl or heteroaryl or $R^{22}$ and $R^{23}$ may be joined to form an optionally substituted 3-7 membered ring, optionally containing an oxygen, sulfur or nitrogen atom, where all these substituents are optionally substituted, and $R^{24}$ is $C_3$-$C_6$ alkenyl, $C_3$-$C_6$alkynyl, $C_3$-$C_7$ cycloalkyl, $C_1$-$C_6$alkylcarbonyl, $C_1$-$C_6$alkoxycarbonyl, $C_1$-$C_6$alkylthiocarbonyl, $C_1$-$C_6$ alkylaminocarbonyl, di$C_1$-$C_6$alkylaminocarbonyl, $C_1$-$C_6$ alkylsulfonyl, tri($C_1$-$C_6$ alkyl) silyl, phenyl or heteroaryl, where all these substituents are optionally substituted.

More preferably, $R^7$, $R^8$, $R^9$ and $R^{10}$ are independently of each other hydrogen, cyano, $C_1$-$C_6$alkyl, $C_2$-$C_6$alkenyl, $C_1$-$C_6$alkoxy, $C_1$-$C_6$alkoxy$C_1$-$C_6$alkyl, 3-7 membered heterocyclyl or $CR^{17}=NOR^{18}$, wherein $R^{17}$ is hydrogen or $C_1$-$C_3$ alkyl and $R^{18}$ is $C_1$-$C_3$ alkyl.

It is especially preferred that $R^7$, $R^8$, $R^9$ and $R^{10}$ are independently of each other hydrogen, $C_1$-$C_6$alkyl, $C_2$-$C_6$ alkenyl, $C_1$-$C_6$alkoxy or $C_1$-$C_6$alkoxy$C_1$-$C_6$alkyl.

In a group of preferred compounds of the formula I $R^7$ and $R^8$ together form a unit $=O$, or form a unit $=CR^{25}R^{26}$, or form a unit $=NR^{27}$, or form together with the carbon atom to which they are attached a 3-8 membered ring, optionally containing a heteroatom selected from O, S or N and optionally substituted by $C_1$-$C_3$alkyl, $C_1$-$C_3$alkoxy, $C_1$-$C_3$alkylthio, $C_1$-$C_3$alkylsulfinyl, $C_1$-$C_3$alkylsulfonyl, $C_1$-$C_3$haloalkyl, halogen, phenyl, phenyl substituted by $C_1$-$C_4$alkyl, $C_1$-$C_4$ haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$ alkylcarbonyl, $C_1$-$C_4$alkoxycarbonyl, aminocarbonyl, $C_1$-$C_6$alkylaminocarbonyl, di$C_1$-$C_6$alkylaminocarbonyl, halogen, cyano or by nitro, heteroaryl or heteroaryl substituted by $C_1$-$C_4$ alkyl, $C_1$-$C_4$ haloalkyl, $C_1$-$C_4$ alkoxy, $C_1$-$C_4$ haloalkoxy, $C_1$-$C_4$ alkylthio, $C_1$-$C_4$ alkylsulfinyl, $C_1$-$C_4$ alkylsulfonyl, $C_1$-$C_4$ alkylcarbonyl, halogen, cyano or by nitro, wherein $R^{25}$ and $R^{26}$ are independently of each other hydrogen, halogen, cyano or nitro, or $R^{25}$ and $R^{26}$ are independently of each other $C_1$-$C_6$ alkyl, $C_1$-$C_6$ alkoxy, $C_1$-$C_6$alkylamino, di$C_1$-$C_6$ alkylamino, $C_1$-$C_6$alkylcarbonyl, $C_1$-$C_6$ alkoxycarbonyl, C₁-C₆alkylaminocarbonyl, diC₁-C₆alkylaminocarbonyl, N-phenyl-N—C₁-C₆ alkylaminocarbonyl, N-phenylC₁-C₆alkyl-N—C₁-C₆ alkylaminocarbonyl, N-heteroaryl-N—C₁-C₆ alkylaminocarbonyl, N-heteroarylC₁-C₆ alkyl-N—C₁-C₆ alkylaminocarbonyl, phenyl, heteroaryl, C₃-C₈ cycloalkyl or 3-7 membered heterocyclyl, where all these substituents are optionally substituted, or R²⁵ and R²⁶ may be joined together to form a 5-8 membered ring optionally containing a heteroatom selected from O, S or N and optionally substituted by C₁-C₂ alkyl or C₁-C₂ alkoxy, R²⁷ is nitro or cyano, or R²⁷ is C₁-C₆ alkylamino, diC₁-C₆ alkylamino, C₁-C₆ alkoxy, C₃-C₆alkenyloxy, C₃-C₆alkynyloxy, phenoxy, phenylamino, N-phenyl-N—C₁-C₆alkylamino, N-phenylC₁-C₆alkyl-N—C₁-C₆alkylamino heteroaryloxy, heteroarylamino, N-heteroaryl-N—C₁-C₆ alkylamino or N-heteroarylC₁-C₆ alkyl-N—C₁-C₆ alkylamino, where all these substituents are optionally substituted, where It is particularly preferred, when R⁷ and R⁸ together form a unit =O or =NR⁷, wherein R²⁷ is C₁₋₃alkoxy.

Preference is given to compounds of the formula I, wherein R⁷ and R¹⁰ together with the carbon atoms to which they are attached form a saturated 3-4 membered ring, optionally containing a heteroatom or group selected from O, S, or NR²⁸, and optionally substituted by C₁-C₄ alkyl, C₁-C₄ alkoxy, C₁-C₄ alkylthio, halogen, C₁-C₄ alkylcarbonyl or C₁-C₄ alkoxycarbonyl, or R⁷ and R¹⁰ together with the carbon atoms to which they are attached form a 5-8 membered ring, optionally containing a heteroatom selected from O, S or N, and optionally substituted by C₁-C₃ alkyl, C₁-C₃ alkoxy, C₁-C₃alkylthio, C₁-C₃ alkylsulfinyl, C₁-C₃ alkylsulfonyl, C₁-C₃ haloalkyl, halogen, phenyl, phenyl substituted by C₁-C₄alkyl, C₁-C₄haloalkyl, C₁-C₄alkoxy, C₁-C₄haloalkoxy, C₁-C₄alkylthio, C₁-C₆alkylsulfinyl, C₁-C₆alkylsulfonyl, C₁-C₄ alkylcarbonyl, C₁-C₄alkoxycarbonyl, aminocarbonyl, C₁-C₈ alkylaminocarbonyl, diC₁-C₈alkylaminocarbonyl, halogen, cyano or by nitro, heteroaryl or heteroaryl substituted by C₁-C₄ alkyl, C₁-C₄ haloalkyl, C₁-C₄ alkoxy, C₁-C₄ haloalkoxy, C₁-C₄ alkylthio, C₁-C₄ alkylsulfinyl, C₁-C₄ alkylsulfonyl, C₁-C₄ alkylcarbonyl, halogen, cyano or by nitro, or R⁷ and R¹⁰ together form a bond, wherein R²⁸ is hydrogen, C₁-C₆ alkyl, C₃-C₆alkenyl, C₃-C₆ alkynyl, C₁-C₆ alkoxy, C₁-C₆ alkylcarbonyl, C₁-C₆ alkoxycarbonyl, C₁-C₆ alkylaminocarbonyl, diC₁-C₆ alkylaminocarbonyl, phenoxycarbonyl C₁-C₆ alkylsulfonyl, phenylsulfonyl or heteroaryloxycarbonyl, where all these substituents are optionally substituted.

More preferably, R⁷ and R¹⁰ together form a bond.

The compounds of the formula (I) are known compounds (see references cited on page 1). The process of preparation is described therein.

The following compounds are preferred compounds:

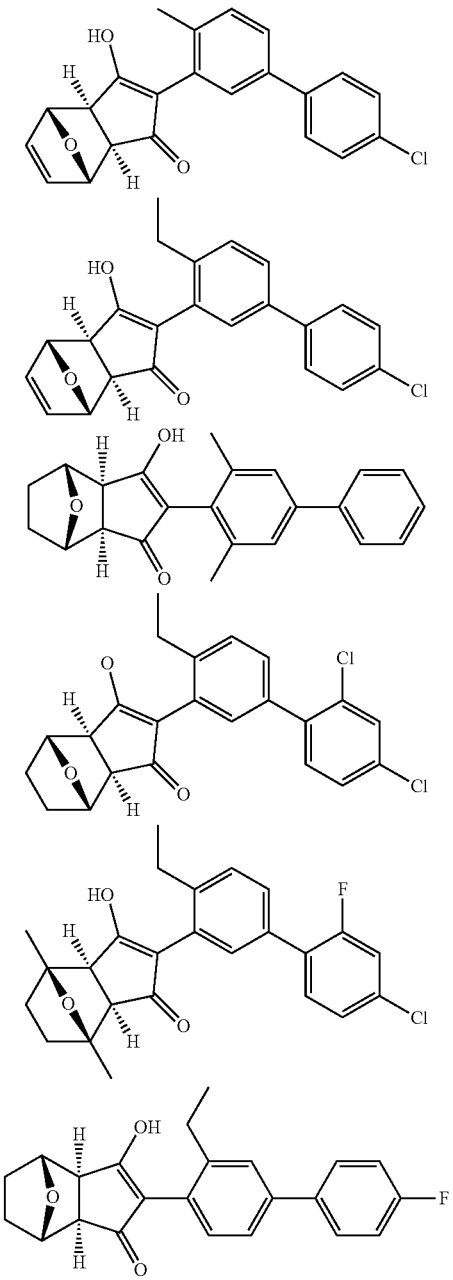

TABLE T1

| Compound Number | Structure | ¹H nmr (CDCl₃ unless stated) or other physical data |
|---|---|---|
| T1 | 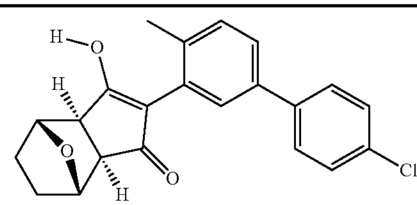 | δ_H 7.52-7.19 (7H, m), 4.62-4.58 (2H, m), 2.69-2.67 (2H, m), 2.12 (3H, s), 1.76-1.73 (2H, m), 1.47-1.41 (2H, m). |

TABLE T1-continued

| Compound Number | Structure | $^1$H nmr (CDCl$_3$ unless stated) or other physical data |
|---|---|---|
| T2 | 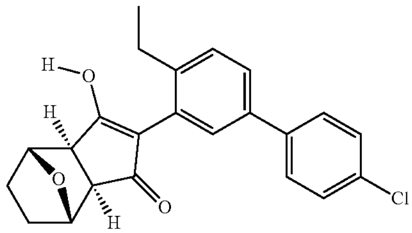 [SMILES: CCc1ccc(-c2ccc(Cl)cc2)cc1C1=C(O)[C@H]2[C@@H](C1=O)[C@@H]1CC[C@H]2O1] | $\delta_H$ 7.61-7.18 (7H, m), 4.62 (2H, br. s), 2.85 (2H, br. s). 2.52 (2H, q), 1.86-1.78 (2H, m), 1.68-1.63 (2H, m), 1.11 (3H, t). |
| T3 | 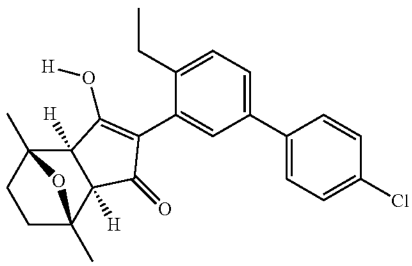 [SMILES: CCc1ccc(-c2ccc(Cl)cc2)cc1C1=C(O)[C@H]2[C@@H](C1=O)[C@]1(C)CC[C@@]2(C)O1] | $\delta_H$ 7.51-7.47 (3H, m), 7.40-7.37 (3H, m), 7.23 (1H, apparent s), 2.81 (2H, br. s), 2.60-2.53 (2H, m), 1.75-1.72 (4H, m), 1.58 (6H, s), 1.16 (3H, t). |
| T4 | 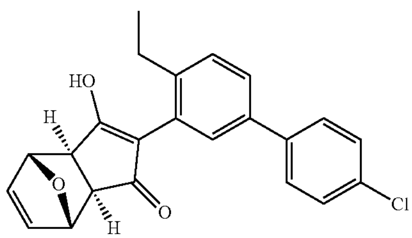 [SMILES: CCc1ccc(-c2ccc(Cl)cc2)cc1C1=C(O)[C@H]2[C@@H](C1=O)[C@@H]1C=C[C@H]2O1] | $\delta_H$ 7.52-7.47 (3H, m), 7.40-7.37 (3H, m), 7.25 (1H, m), 6.51 (2H, s), 5.10 (2H, br. s), 2.81 (2H, br. s), 2.53 (2H, q), 1.15-1.12 (3H, m). |
| T5 | 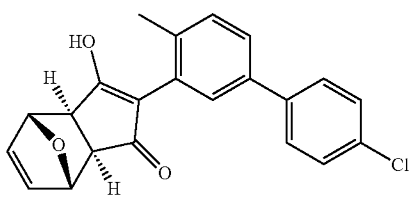 [SMILES: Cc1ccc(-c2ccc(Cl)cc2)cc1C1=C(O)[C@H]2[C@@H](C1=O)[C@@H]1C=C[C@H]2O1] | $\delta_H$ 7.31-7.10 (7H, m), 6.54-6.49 (2H, m), 5.17 (1H, s), 5.13 (1H, s), 3.16 (1H, d), 2.77 (1H, d), 2.26 (3H, s). |
| T6 | 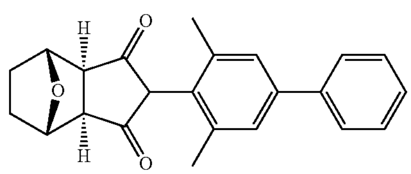 [SMILES: Cc1cc(-c2ccccc2)cc(C)c1C1C(=O)[C@@H]2[C@H](C1=O)[C@H]1CC[C@@H]2O1] | (d$_4$-MeOH) $\delta_H$ 7.60 (2H, d), 7.43 (2H, t), 7.39-7.31 (3H, m), 4.64 (2H, m), 2.90 (2H, s), 2.19 (6H, s), 1.88-1.82 (2H, m), 1.73-1.67 (2H, m). |
| T7 | 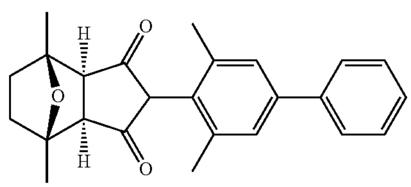 [SMILES: Cc1cc(-c2ccccc2)cc(C)c1C1C(=O)[C@@H]2[C@H](C1=O)[C@@]1(C)CC[C@]2(C)O1] | $\delta_H$ 7.55 (2H, d), 7.43 (2H, t), 7.36-7.30 (3H, m), 3.03 (1H, d), 2.69 (1H, d), 2.24 (3H, s), 2.18 (3H, s), 1.80-1.70 (4H, m), 1.57 (d, 6H). |
| T8 | 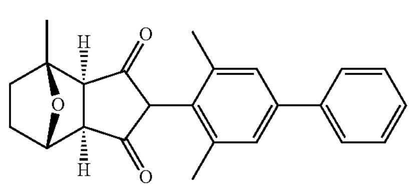 [SMILES: Cc1cc(-c2ccccc2)cc(C)c1C1C(=O)[C@H]2[C@@H]3CC[C@@](C)(O3)[C@H]2C1=O] | $\delta_H$ 7.56 (2H, d), 7.43 (2H, t), 7.36-7.31 (3H, m), 4.70 (0.5H, d), 4.66 (0.5H, d), 3.08 (0.5H, d), 2.94 (0.5H, d), 2.83 (0.5H, d), 2.62 (0.5H, d), 2.23 (3H, d), 2.18 (H, s), 2.04-1.94 (1H, m), 1.69-1.59 (6H, m). |

TABLE T1-continued

| Compound Number | Structure | ¹H nmr (CDCl₃ unless stated) or other physical data |
|---|---|---|
| T9 | 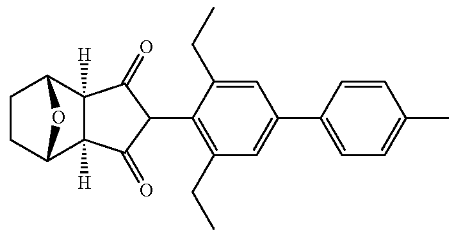 [SMILES: CCc1cc(-c2ccc(C)cc2)cc(CC)c1C1C(=O)[C@@H]2[C@H](C1=O)[C@H]1CC[C@@H]2O1] | δ$_H$ 7.47 (2H, d), 7.32 (2H, d), 7.24 (2H, d), 6.99 (1H, br s), 4.72 (2H, s), 2.96 (1H, br s), 2.73 (1H, br s), 2.47 (4H, br m), 2.39 (3H, s), 1.84 (2H, br s), 1.58 (2H, d), 1.1 (6H, m). |
| T10 | 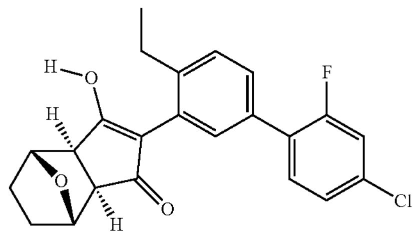 [SMILES: CCc1ccc(-c2ccc(Cl)cc2F)cc1C1=C(O)[C@H]2[C@@H](C1=O)[C@@H]1CC[C@H]2O1] | (d₄-MeOH) δ$_H$ 7.48-7.41 (2H, m), 7.34 (1H, d), 7.26-7.24 (2H, m), 7.15 (1H, s), 4.61 (2H, s), 2.85 (2H, s), 2.51 (2H, q), 1.82-1.80 (2H, m), 1.65 (2H, d), 1.11 (3H, t). |
| T11 | 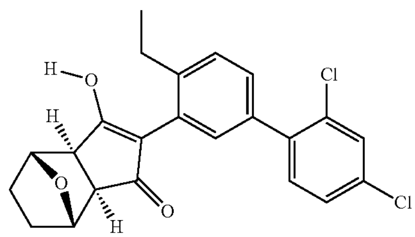 [SMILES: CCc1ccc(-c2ccc(Cl)cc2Cl)cc1C1=C(O)[C@H]2[C@@H](C1=O)[C@@H]1CC[C@H]2O1] | (d₄-MeOH) δ$_H$ 7.52-7.51 (1H, m), 7.35-7.32 (4H, m), 7.03 (1H, s), 4.61-4.60 (2H, m), 2.84 (2H, s), 2.52 (2H, q), 1.82-1.79 (2H, m), 1.67-1.64 (2H. m), 1.12 (3H, t). |
| T12 | 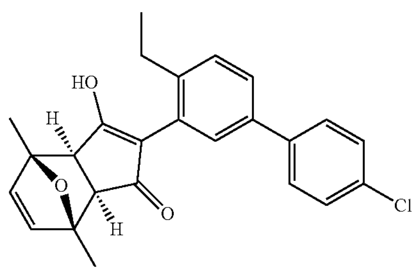 [SMILES: CCc1ccc(-c2ccc(Cl)cc2)cc1C1=C(O)[C@H]2[C@@H](C1=O)[C@]1(C)C=C[C@@]2(C)O1] | (d₄-MeOH) δ$_H$ 7.59-7.56 (2H, m), 7.51 (1H, dd), 7.42-7.39 (2H, m), 7.35 (1H, d), 7.26 (1H, d), 6.36 (2H, s), 2.80 (2H, s), 2.54 (2H, q), 1.63 (6H, s), 1.12 (3H, t). |
| T13 | 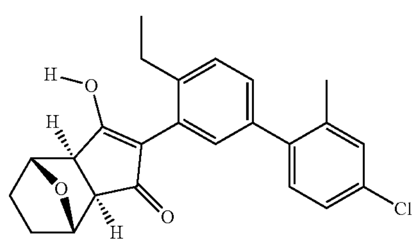 [SMILES: CCc1ccc(-c2ccc(Cl)cc2C)cc1C1=C(O)[C@H]2[C@@H](C1=O)[C@@H]1CC[C@H]2O1] | δ$_H$ 7.28 (1H, s), 7.17-7.11 (4H, m), 6.96 (1H, s), 4.63 (2H, s), 2.73 (2H, s), 2.51-2.46 (2H, m), 2.22 (3H, s), 1.79 (2H, br. m), 1.55 (2H, d), 1.10 (3H, t). |
| T14 | 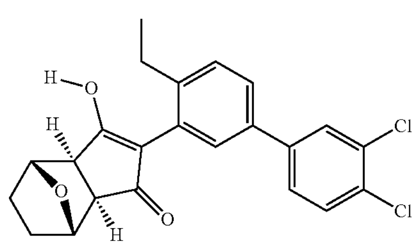 [SMILES: CCc1ccc(-c2ccc(Cl)c(Cl)c2)cc1C1=C(O)[C@H]2[C@@H](C1=O)[C@@H]1CC[C@H]2O1] | δ$_H$ 7.80 (1H, s), 7.38-7.36 (3H, br. m), 7.29-7.27 (1H, br. m), 7.20 (1H, br. s), 4.65 (2H, s), 2.70 (2H, br. s), 2.50-2.40 (2H, br. m), 1.77 (2H, br. s), 1.49 (2H, br. s), 1.09 (3H, br. s). |

TABLE T1-continued

| Compound Number | Structure | ¹H nmr (CDCl₃ unless stated) or other physical data |
|---|---|---|
| T15 | 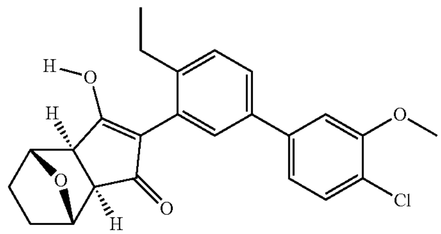 [SMILES: CCc1ccc(-c2ccc(Cl)c(OC)c2)cc1C1=C(O)[C@H]2[C@@H](C1=O)[C@@H]1CC[C@H]2O1] | $\delta_H$ 7.41 (1H, d), 7.31 (2H, t), 7.22 (1H, br. s), 7.09-7.04 (2H, m), 4.66 (2H, s), 3.91 (3H, s), 2.75 (2H, s), 2.50-2.45 (2H, q), 1.82-1.80 (2H, m), 1.56 (2H, d), 1.09 (3H, 1). |
| T16 | 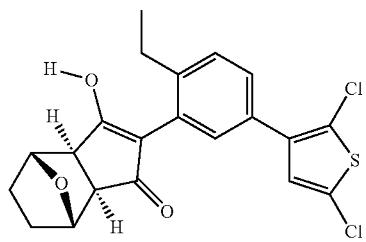 [SMILES: CCc1ccc(-c2cc(Cl)sc2Cl)cc1C1=C(O)[C@H]2[C@@H](C1=O)[C@@H]1CC[C@H]2O1] | $\delta_H$ 7.42 (1H, d), 7.28 (1H, d), 7.15 (1H, s), 6.87 (1H, s), 4.65 (2H, s), 2.71 (2H, s), 2.50-2.48 (2H, m), 1.77 (2H, br. s), 1.50 (2H, br. s), 1.13-1.08 (3H, br. m). |
| T17 | 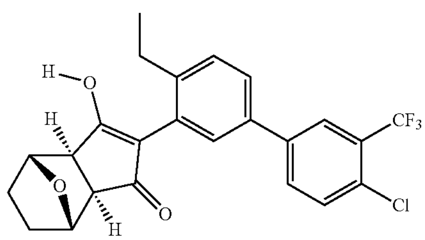 [SMILES: CCc1ccc(-c2ccc(Cl)c(C(F)(F)F)c2)cc1C1=C(O)[C@H]2[C@@H](C1=O)[C@@H]1CC[C@H]2O1] | $\delta_H$ 7.86 (1H, s), 7.65 (1H, s), 7.51-7.30 (4H, m), 4.70 (2H, s), 2.77-2.55 (4H, m), 1.82 (2H, br. s), 1.55 (2H, br. s), 1.15 (3H, br. apparent s). |
| T18 | 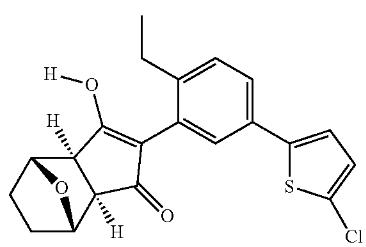 [SMILES: CCc1ccc(-c2ccc(Cl)s2)cc1C1=C(O)[C@H]2[C@@H](C1=O)[C@@H]1CC[C@H]2O1] | $\delta_H$ 7.56-7.54 (1H, br. m), 7.36-7.34 (1H, m), 7.22-7.18 (1H, m), 6.98 (1H, s), 6.82 (1H, s), 4.67 (2H, s), 2.73 (2H, s), 2.47-2.40 (2H, m), 1.79 (2H, 8), 1.52 (2H, s), 1.09 (3H, br. apparent s). |
| T19 | 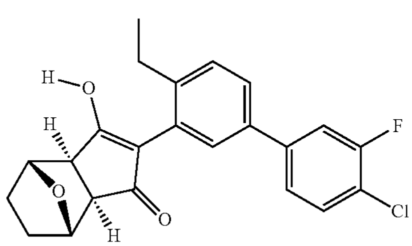 [SMILES: CCc1ccc(-c2ccc(Cl)c(F)c2)cc1C1=C(O)[C@H]2[C@@H](C1=O)[C@@H]1CC[C@H]2O1] | $\delta_H$ 7.41-7.38 (1H, m), 7.35 (1H, d), 7.30 (2H, d), 7.24-7.21 (2H, br. m), 4.66 (2H, s), 2.73 (2H, s), 2.51-2.46 (2H, m), 1.80-1.78 (2H, m), 1.52 (2H, d), 1.10 (3H, t). |
| T20 | 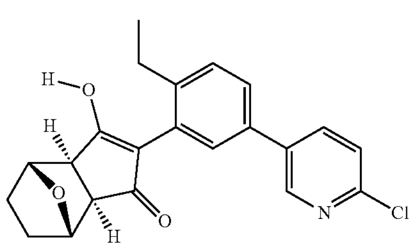 [SMILES: CCc1ccc(-c2ccc(Cl)nc2)cc1C1=C(O)[C@H]2[C@@H](C1=O)[C@@H]1CC[C@H]2O1] | $\delta_H$ 7.79-7.71 (2H, m), 7.22-7.20 (2H, m), 7.08-7.02 (2H, br. m), 4.75 (2H, s), 2.58-2.53 (4H, m), 1.85-1.84 (2H, br. m), 1.58 (2H, d), 1.08 (3H, t). |

TABLE T1-continued

| Compound Number | Structure | $^1$H nmr (CDCl$_3$ unless stated) or other physical data |
|---|---|---|
| T21 | 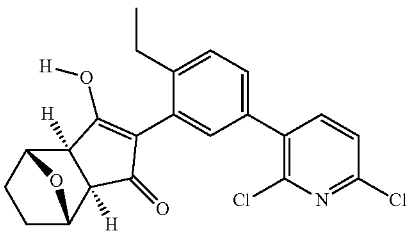 [SMILES: CCc1ccc(-c2ccc(Cl)nc2Cl)cc1C1=C(O)[C@H]2[C@@H](C1=O)[C@@H]1CC[C@H]2O1] | δ$_H$ 7.65-7.83 (1H, m), 7.32-7.28 (3H, m), 7.06 (1H, s), 4.64 (2H, s), 2.73 (2H, s), 2.50-2.48 (2H, m), 1.80-1.79 (2H, m), 1.54-1.53 (2H, m), 1.12-1.07 (3H, m). |
| T22 | 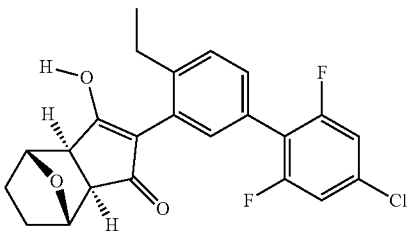 [SMILES: CCc1ccc(-c2c(F)cc(Cl)cc2F)cc1C1=C(O)[C@H]2[C@@H](C1=O)[C@@H]1CC[C@H]2O1] | δ$_H$ 7.37-7.32 (2H, m), 7.13 (1H, br. s), 6.98 (2H, d), 4.69 (2H, s), 2.75-2.53 (4H, m), 1.81 (2H, br. s), 1.55 (2H, br. s), 1.14 (3H, t). |
| T23 | 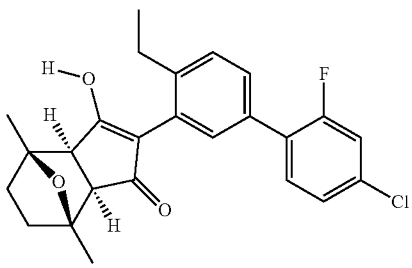 [SMILES: CCc1ccc(-c2ccc(Cl)cc2F)cc1C1=C(O)[C@H]2[C@@H](C1=O)[C@]1(C)CC[C@@]2(C)O1] | (d$_4$-MeOH) δ$_H$ 7.45-7.43 (1H, m), 7.38-7.31 (2H, m), 7.16-7.13 (3H, m), 2.78 (2H, br. s), 2.54 (2H, br. m), 1.75-1.70 (4H, m), 1.56 (6H, s), 1.15 (3H, t) |
| T24 | 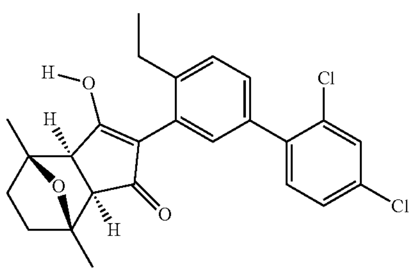 [SMILES: CCc1ccc(-c2ccc(Cl)cc2Cl)cc1C1=C(O)[C@H]2[C@@H](C1=O)[C@]1(C)CC[C@@]2(C)O1] | (d$_4$-MeOH) δ$_H$ 7.52 (1H), 7.37-7.34 (4H, m), 7.05 (1H, s), 2.85 (2H, s), 2.56-2.54 (2H, m), 1.85-1.81 (2H, m), 1.69-1.66 (2H, m), 1.52 (6H, s), 1.14 (3H, t) |
| T25 | 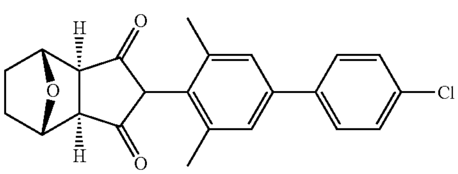 [SMILES: Cc1cc(-c2ccc(Cl)cc2)cc(C)c1C1C(=O)[C@@H]2[C@H](C1=O)[C@H]1CC[C@@H]2O1] | (d$_4$-MeOH) δ$_H$ 7.58 (2H, d), 7.40 (2H, d), 7.28 (2H, s), 4.61 (2H, m), 2.87 (2H, s), 2.15 (6H, s), 1.82 (2H, m), 1.67 (2H, m) |
| T26 | 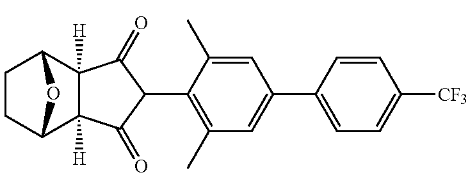 [SMILES: Cc1cc(-c2ccc(C(F)(F)F)cc2)cc(C)c1C1C(=O)[C@@H]2[C@H](C1=O)[C@H]1CC[C@@H]2O1] | (d4-DMSO) δ$_H$ 7.80 (2H, d), 7.74 (2H, d), 7.31 (2H, s), 4.46 (2H, s), 2.73 (2H, s), 2.04 (6H, d), 1.61 (2H, m), 1.51 (2H, m) |
| T27 | 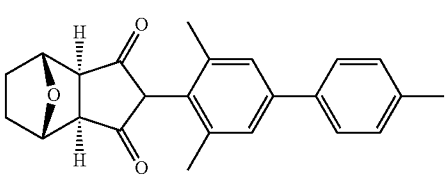 [SMILES: Cc1ccc(-c2cc(C)c(C3C(=O)[C@@H]4[C@H](C3=O)[C@H]3CC[C@@H]4O3)c(C)c2)cc1] | (d$_3$-Acetonitrile) δ$_H$ 7.55 (2H, d), 7.33 (2H, s), 7.28 (2H, d), 4.60 (2H, d), 2.85 (2H, s), 2.1.6 (6H, d), 1.80 (2H, m), 1.65 (2H, m) |

TABLE T1-continued

| Compound Number | Structure | $^1$H nmr (CDCl$_3$ unless stated) or other physical data |
|---|---|---|
| T28 | 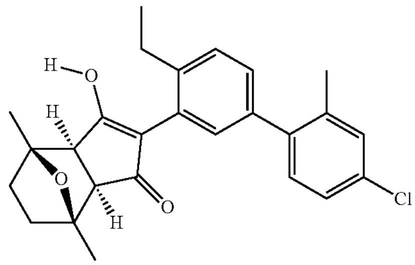 [SMILES: CCc1ccc(-c2ccc(Cl)cc2C)cc1C1=C(O)[C@H]2[C@@H](C1=O)[C@]1(C)CC[C@@]2(C)O1] | $\delta_H$ 7.29 (1H, d), 7.20-7.07 (4H, m), 6.91 (1H, s), 2.73 (2H, br. s), 2.52 (2H, br. m), 2.22 (3H, s), 1.68 (4H, s), 1.53 (6H, s), 1.13 (3H, t). |
| T29 | 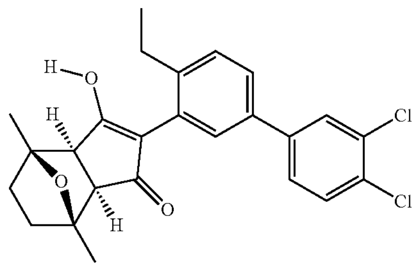 [SMILES: CCc1ccc(-c2ccc(Cl)c(Cl)c2)cc1C1=C(O)[C@H]2[C@@H](C1=O)[C@]1(C)CC[C@@]2(C)O1] | $\delta_H$ 7.59 (1H, s), 7.43 (2H, d), 7.34 (2H, d), 7.17 (1H, s), 2.78 (2H, br. s), 2.52 (2H, br. m), 1.71 (4H, s), 1.54 (6H, s), 1.12 (3H, t). |
| T30 | 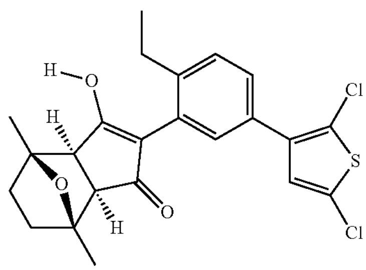 [SMILES: CCc1ccc(-c2cc(Cl)sc2Cl)cc1C1=C(O)[C@H]2[C@@H](C1=O)[C@]1(C)CC[C@@]2(C)O1] | $\delta_H$ 7.45 (1H, d), 7.35 (1H, d), 7.17 (1H, d), 6.87 (1H, s), 2.78 (2H, br. s), 2.57-2.53 (2H, br. m), 1.75-1.70 (4H, m), 1.56 (6H, s), 1.14 (3H, t). |
| T31 | 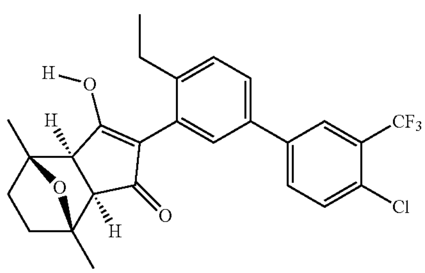 [SMILES: CCc1ccc(-c2ccc(Cl)c(C(F)(F)F)c2)cc1C1=C(O)[C@H]2[C@@H](C1=O)[C@]1(C)CC[C@@]2(C)O1] | $\delta_H$ 7.80 (1H, s), 7.59 (1H, d), 7.46 (2H, dd), 7.35 (1H, d), 7.18 (1H. s), 2.76 (2H, br. s), 2.50 (2H, br. apparent s), 1.69 (4H, s), 1.54 (6H, s), 1.12 (3H, t). |
| T32 | 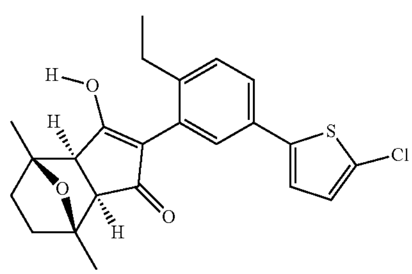 [SMILES: CCc1ccc(-c2ccc(Cl)s2)cc1C1=C(O)[C@H]2[C@@H](C1=O)[C@]1(C)CC[C@@]2(C)O1] | $\delta_H$ 7.35 (1H, d), 7.22 (1H, d), 7.11 (1H, s), 6.98 (1H, d), 6.82 (1 H, d), 2.68 (2H, s), 2.44 (2H, br. apparent s), 1.64 (4H, s), 1.51 (6H, s), 1.07 (3H, t). |

TABLE T1-continued

| Compound Number | Structure | ¹H nmr (CDCl₃ unless stated) or other physical data |
|---|---|---|
| T33 | 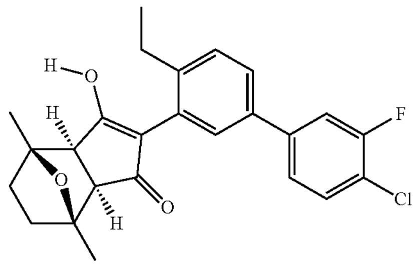 [SMILES: CCc1ccc(-c2ccc(Cl)c(F)c2)cc1C1=C(O)[C@H]2[C@@H](C1=O)[C@]1(C)CC[C@@]2(C)O1] | δ_H 7.42-7.21 (5H, m), 7.14 (1H, s), 2.71 (2H, br. s), 2.49-2.47 (2H, br. m), 1.68 (4H, s), 1.52 (6H, s), 1.10 (3H, t). |
| T34 | 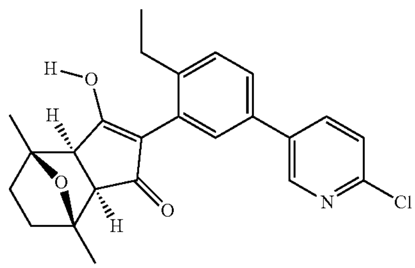 [SMILES: CCc1ccc(-c2ccc(Cl)nc2)cc1C1=C(O)[C@H]2[C@@H](C1=O)[C@]1(C)CC[C@@]2(C)O1] | δ_H 7.67 (1H, d), 7.51 (1H, s), 7.15 (2H, br. s), 6.94-6.88 (2H, m), 2.57 (4H, br. m), 1.76-1.72 (4H, br. m), 1.63 (6H, br. s), 1.09 (3H, t). |
| T35 | 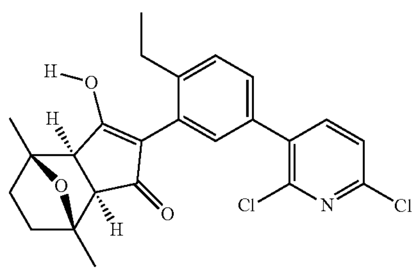 [SMILES: CCc1ccc(-c2ccc(Cl)nc2Cl)cc1C1=C(O)[C@H]2[C@@H](C1=O)[C@]1(C)CC[C@@]2(C)O1] | δ_H 7.63 (1H, d), 7.38 (2H, s), 7.29 (1H, d), 7.12 (1H, s), 2.81 (2H, br. s), 2.57 (2H, br. m), 1.76-1.71 (4H, m), 1.57 (6H, s), 1.17 (3H, t). |
| T36 | 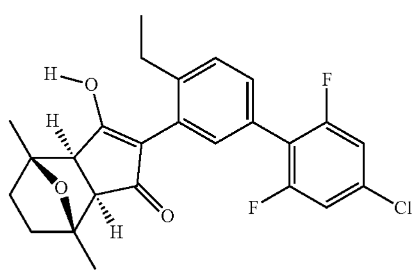 [SMILES: CCc1ccc(-c2c(F)cc(Cl)cc2F)cc1C1=C(O)[C@H]2[C@@H](C1=O)[C@]1(C)CC[C@@]2(C)O1] | δ_H 7.42-7.37 (2H, m), 7.11 (1H, s), 7.01-6.99 (2H, m), 2.80-2.53 (3H, m), 2.00 (1H, s), 1.76-1.71 (4H, m), 1.57 (6H, s), 1.17 (3H, t). |
| T37 | 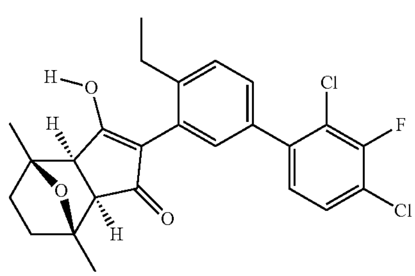 [SMILES: CCc1ccc(-c2ccc(Cl)c(F)c2Cl)cc1C1=C(O)[C@H]2[C@@H](C1=O)[C@]1(C)CC[C@@]2(C)O1] | δ_H 7.40 (1H, d), 7.35-7.33 (1H, m), 7.16-7.13 (2H, m), 7.10-7.06 (1H, m), 2.72 (2H, br. s), 2.50-2.49 (2H, br. m), 1.68 (4H, s), 1.53 (6H, s), 1.12 (3H, t). |

TABLE T1-continued

| Compound Number | Structure | ¹H nmr (CDCl₃ unless stated) or other physical data |
|---|---|---|
| T38 | 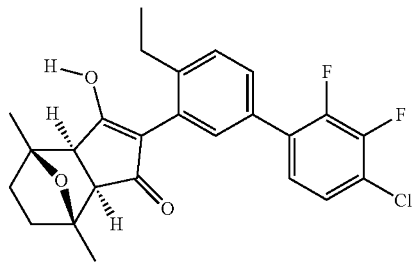 [SMILES: CCc1ccc(-c2ccc(Cl)c(F)c2F)cc1C1=C(O)[C@H]2[C@@H](C1=O)[C@]1(C)CC[C@@]2(C)O1] | $\delta_H$ 7.32-7.27 (2H, br. m), 7.04-7.02 (3H, br. m), 2.82-2.67 (2H, br. m), 2.51 (2H, s), 1.69 (4H, s), 1.53 (6H, s), 1.13 (3H, t). |
| T39 | 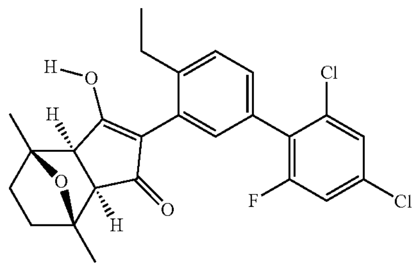 [SMILES: CCc1ccc(-c2c(F)cc(Cl)cc2Cl)cc1C1=C(O)[C@H]2[C@@H](C1=O)[C@]1(C)CC[C@@]2(C)O1] | $\delta_H$ 7.41 (1H, d), 7.31-7.29 (2H, m), 7.10 (1H, dd), 7.01 (1H, br. s), 2.79 (2H, br. s), 2.61-2.53 (2H, m), 1.76-1.71 (4H, m), 1.57 (6H, s), 1.18 (3H, t). |
| T40 | 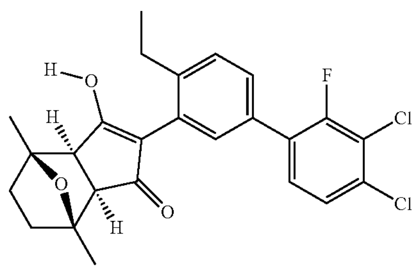 [SMILES: CCc1ccc(-c2ccc(Cl)c(Cl)c2F)cc1C1=C(O)[C@H]2[C@@H](C1=O)[C@]1(C)CC[C@@]2(C)O1] | (d₆-acetone) $\delta_H$ 7.50-7.43 (3H, m), 7.36 (1H, d), 7.19 (1H, s), 2.83 (2H, br. s), 2.58 (2H, q), 1.81-1.77 (2H, m), 1.63-1.60 (2H, m), 1.50 (6H, s), 1.13 (3H, t). |
| T41 | 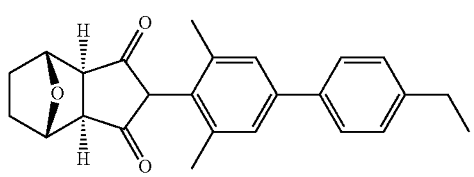 [SMILES: CCc1ccc(-c2cc(C)c(C3C(=O)[C@@H]4[C@H](C3=O)[C@H]3CC[C@@H]4O3)c(C)c2)cc1] | (d₆-DMSO) $\delta_H$ 7.55 (2H, d), 7.28 (2H, d), 7.26 (2H, s), 4.52 (2H, s), 2.80 (2H, s), 2.64 (2H, q), 2.07 (6H, d), 1.68 (2H, m), 1.57 (2H, m), 1.21 (3H, t). |
| T42 | 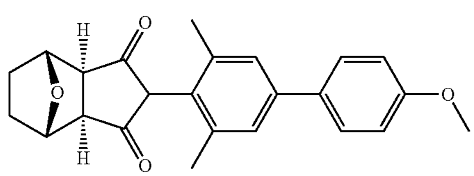 [SMILES: COc1ccc(-c2cc(C)c(C3C(=O)[C@@H]4[C@H](C3=O)[C@H]3CC[C@@H]4O3)c(C)c2)cc1] | (d₆-DMSO) $\delta_H$ 7.57 (2H, d), 7.24 (2H, s), 7.01 (2H, d), 4.52 (2H, s), 3.79 (314, s), 2.80 (2H, s), 2.08 (6H, d), 1.67 (2H, m), 1.57 (2H, m). |
| T43 | 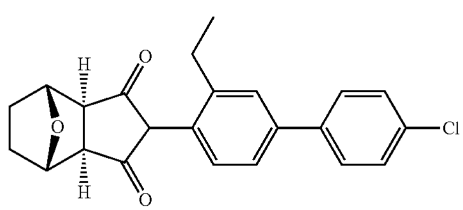 [SMILES: CCc1cc(-c2ccc(Cl)cc2)ccc1C1C(=O)[C@@H]2[C@H](C1=O)[C@H]1CC[C@@H]2O1] | (d₄-methanol) $\delta_H$ 7.61 (2H, dd), 7.49 (1H, d), 7.39-7.45 (3H, m), 7.08 (1H, dd), 4.62 (2H, s), 2.85 (2H, s), 2.54 (2H, q), 1.79-1.86 (2H, m) 1.67 (2H, m), 1.13 (3H, t). |
| T44 | 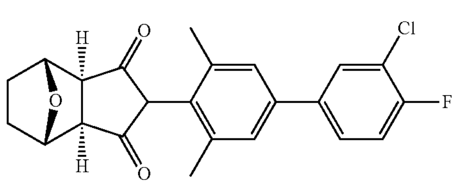 [SMILES: Cc1cc(-c2ccc(F)c(Cl)c2)cc(C)c1C1C(=O)[C@@H]2[C@H](C1=O)[C@H]1CC[C@@H]2O1] | $\delta_H$ 7.50 (2H, d), 7.40 (1H, m), 7.10 (2H, d), 4.50 (2H, s), 2.80 (2H, s), 2.10 (6H, d), 1.70 (2H, m), 1.40 (2H, d). |

TABLE T1-continued
| Compound Number | Structure | ¹H nmr (CDCl₃ unless stated) or other physical data |
|---|---|---|
| T45 | 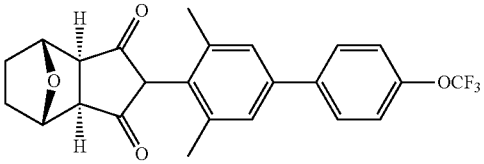 [SMILES: Cc1cc(-c2ccc(OC(F)(F)F)cc2)cc(C)c1C1C(=O)[C@@H]2[C@H](C1=O)[C@H]1CC[C@@H]2O1] | δ_H 7.50 (2H, d), 7.20 (4H, m), 4.40 (2H, m), 2.80 (2H, m), 2.00 (6H, d), 1.60 (2H, m), 1.50 (2H, d). |
| T46 | 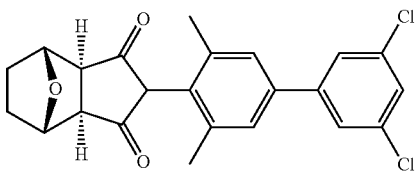 [SMILES: Cc1cc(-c2cc(Cl)cc(Cl)c2)cc(C)c1C1C(=O)[C@@H]2[C@H](C1=O)[C@H]1CC[C@@H]2O1] | δ_H 7.50 (1H, d), 7.40 (1H, s), 7.35 (1H, d), 7.10 (2H, d), 4.50 (2H, s), 2.80 (2H, s), 2.10 (6H, s), 1.70 (2H, m), 1.40 (2H, d). |
| T47 | 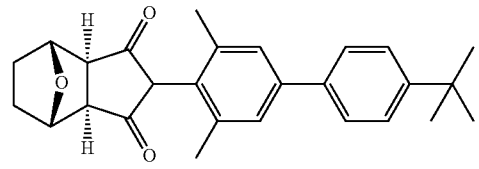 [SMILES: Cc1cc(-c2ccc(C(C)(C)C)cc2)cc(C)c1C1C(=O)[C@@H]2[C@H](C1=O)[C@H]1CC[C@@H]2O1] | δ_H 7.50 (2H, d), 7.40 (2H, s), 7.20 (2H, s), 4.50 (2H, s), 2.80 (2H, m), 2.00 (6H, d), 1.65 (2H, m), 1.50 (2H, d), 1.20 (9H, s). |
| T48 | 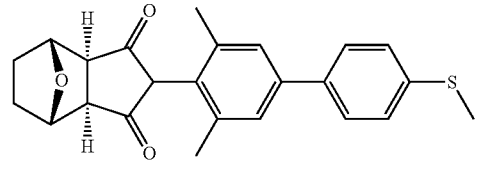 [SMILES: CSc1ccc(-c2cc(C)c(C3C(=O)[C@@H]4[C@H](C3=O)[C@H]3CC[C@@H]4O3)c(C)c2)cc1] | δ_H 7.60 (2H, d), 7.30 (2H, d), 7.20 (2H, s), 4.50 (2H, s), 2.80 (2H, m), 2.50 (3H, s), 2.00 (6H, d), 1.65 (2H, m), 1.50 (2H, d): |
| T49 | 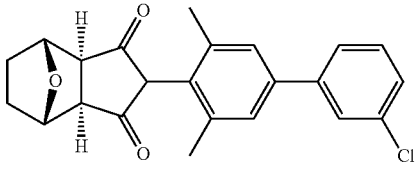 [SMILES: Cc1cc(-c2cccc(Cl)c2)cc(C)c1C1C(=O)[C@@H]2[C@H](C1=O)[C@H]1CC[C@@H]2O1] | δ_H 7.60 (1H, s), 7.50 (1H, d), 7.40 (1H, m), 7.35 (1H, m), 7.30 (2H, s), 4.50 (2H, m), 2.70 (2H, m), 2.00 (6H, d), 1.60 (2H, m), 1.50 (2H, d). |
| T50 | 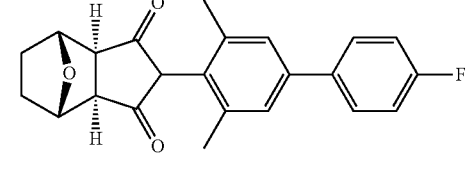 | δ_H 7.60 (2H, m), 7.20 (4H, m), 4.40 (2H, m), 2.80 (2H, m), 2.00 (6H, d), 1.60 (2H, m), 1.50 (2H, d). |
| T51 | 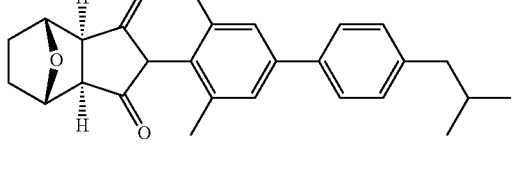 | δ_H 7.50 (2H, m), 7.20 (2H, s), 7.15 (2H, d), 4.40 (2H, m), 3.70 (2H, m), 2.40 (2H, m), 2.00 (6H, d), 1.80 (1H, m), 1.60 (2H, m), 1.50 (2H, d), 1.08 (6H, d). |
| T52 | 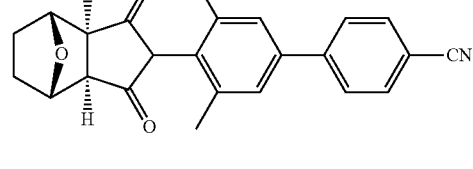 | δ_H 7.70 (2H, m), 7.30 (4H, m), 4.40 (2H, m), 2.80 (2H, m), 2.00 (6H, d), 1.60 (2H, m), 1.50 (2H, d). |

TABLE T1-continued

| Compound Number | Structure | $^1$H nmr (CDCl$_3$ unless stated) or other physical data |
|---|---|---|
| T53 | 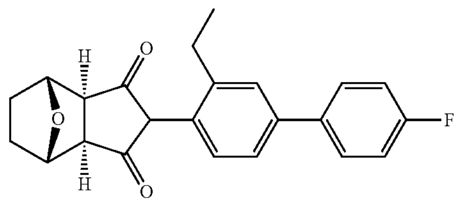 [SMILES: CCc1cc(-c2ccc(F)cc2)ccc1C1C(=O)[C@@H]2[C@H](C1=O)[C@H]1CC[C@@H]2O1] | (d$_4$-methanol) $\delta_H$ 7.62 (2H, m), 7.46 (1H, m), 7.39 (1H, dd), 7.15 (2H, m), 7.06 (1H, d), 4.61 (2H, m), 2.85 (2H, s), 2.53 (2H, q), 1.78-1.86 (2H, m) 1.63-1.70 (2H, m), 1.12 (3H t). |

The compounds of the following Tables 1 to 192 can be obtained in an analogous manner. Table 1 covers 378 compounds of the type T-1.

T-1 wherein R$^1$ is methyl, R$^4$ is hydrogen, R$^5$, R$^6$, R$^7$, R$^8$, R$^9$, R$^{10}$, R$^{11}$ and R$^{12}$ are hydrogen and R$^2$ and R$^3$ are as defined in Table 1.

| Compound Number | R$^2$ | R$^3$ |
|---|---|---|
| 1.001 | phenyl | H |
| 1.002 | 2-fluorophenyl | H |
| 1.003 | 3-fluorophenyl | H |
| 1.004 | 4-fluorophenyl | H |
| 1.005 | 2-chlorophenyl | H |
| 1.006 | 3-chlorophenyl | H |
| 1.007 | 4-chlorophenyl | H |
| 1.008 | 2-bromophenyl | H |
| 1.009 | 3-bromophenyl | H |
| 1.010 | 4-bromophenyl | H |
| 1.011 | 2-methylphenyl | H |
| 1.012 | 3-methylphenyl | H |
| 1.013 | 4-methylphenyl | H |
| 1.014 | 4-ethylphenyl | H |
| 1.015 | 4-isopropylphenyl | H |
| 1.016 | 4-isobutylphenyl | H |
| 1.017 | 4-ten-butylphenyl | H |
| 1.018 | 2-cyanophenyl | H |
| 1.019 | 3-cyanophenyl | H |
| 1.020 | 4-cyanophenyl | H |
| 1.021 | 2-methoxyphenyl | H |
| 1.022 | 3-methoxyphenyl | H |
| 1.023 | 4-methoxyphenyl | H |
| 1.024 | 2-trifluoromethylphenyl | H |
| 1.025 | 3-trifluoromethylphenyl | H |
| 1.026 | 4-trifluoromethylphenyl | H |
| 1.027 | 4-trifluoromethoxyphenyl | H |
| 1.028 | 4-difluoromethoxyphenyl | H |
| 1.029 | 4-methylthiophenyl | H |
| 1.030 | 4-methylsulfinylphenyl | H |
| 1.031 | 4-methylsulfonylphenyl | H |
| 1.032 | 4-trifluoromethylthiophenyl | H |
| 1.033 | 4-trifluoromethylsulfinylphenyl | H |
| 1.034 | 4-trifluoromethylsulfonylphenyl | H |
| 1.035 | 2,3-difluorophenyl | H |
| 1.036 | 2,4-difluorophenyl | H |
| 1.037 | 2,5-difluorophenyl | H |
| 1.038 | 2,6-difluorophenyl | H |
| 1.039 | 3,4-difluorophenyl | H |
| 1.040 | 3,5-difluorophenyl | H |
| 1.041 | 2,3-dichlorophenyl | H |

T-1

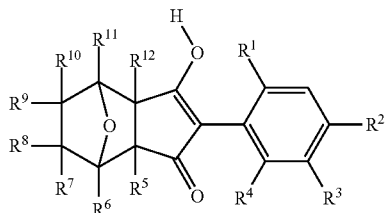

wherein $R^1$ is methyl, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1.

| Compound Number | $R^2$ | $R^3$ |
|---|---|---|
| 1.042 | 2,4-dichlorophenyl | H |
| 1.043 | 2,5-dichlorophenyl | H |
| 1.044 | 2,6-dichlorophenyl | H |
| 1.045 | 3,4-dichtorophenyl | H |
| 1.046 | 3,5-dichlorophenyl | H |
| 1.047 | 2,3,4-trichlorophenyl | H |
| 1.048 | 2,3,5-trichlorophenyl | H |
| 1.049 | 2,3,6-trichlorophenyl | H |
| 1.050 | 2,4,5-trichlorophenyl | H |
| 1.051 | 2,4,6-trichlorophenyl | H |
| 1.052 | 3,4,5-trichlorophenyl | H |
| 1.053 | 2-chloro-3-fluorophenyl | H |
| 1.054 | 2-chloro-4-fluorophenyl | H |
| 1.055 | 2-chloro-4-fluorophenyl | H |
| 1.056 | 2-chloro-4-fluorophenyl | H |
| 1.057 | 3-chloro-2-fluorophenyl | H |
| 1.058 | 3-chloro-4-fluorophenyl | H |
| 1.059 | 3-chloro-5-fluorophenyl | H |
| 1.060 | 4-chloro-2-fluorophenyl | H |
| 1.061 | 4-chloro-3-fluorophenyl | H |
| 1.062 | 5-chloro-2-fluorophenyl | H |
| 1.063 | 4-chloro-2-methylphenyl | H |
| 1.084 | 4-chloro-3-methylphenyl | H |
| 1.065 | 4-chloro-2-trifluoromethylphenyl | H |
| 1.066 | 4-chloro-3-trifluoromethylphenyl | H |
| 1.067 | 4-chloro-2-cyanophenyl | H |
| 1.068 | 4-chloro-3-cyanophenyl | H |
| 1.069 | 4-chloro-2-methoxyphenyl | H |
| 1.070 | 4-chloro-3-methoxyphenyl | H |
| 1.071 | 4-fluoro-2-methylphenyl | H |
| 1.072 | 4-fluoro-3-methylphenyl | H |
| 1.073 | 4-fluoro-2-trifluoromethylphenyl | H |
| 1.074 | 4-fluoro-3-trifluoromethylphenyl | H |
| 1.075 | 2-fluoro-4-trifluoromethylphenyl | H |
| 1.076 | 3-fluoro-4-trifluoromethylphenyl | H |
| 1.077 | 2,3,4-trifluorophenyl | H |
| 1.078 | 2,3,5-trifluorophenyl | H |
| 1.079 | 2,3,6-trifluorophenyl | H |
| 1.080 | 2,4,5-trifluorophenyl | H |
| 1.081 | 2,4,6-trifluorophenyl | H |
| 1.082 | 3,4,5-trifluorophenyl | H |
| 1.083 | 3,4-dichloro-2-fluorophenyl | H |
| 1.084 | 3,4-dichoro-5-fluorophenyl | H |
| 1.085 | 4,5-dichloro-2-fluorophenyl | H |
| 1.086 | 2-chloro-3,4-difluorophenyl | H |
| 1.087 | 2-chloro-4,5-difluorophenyl | H |
| 1.088 | 2-chloro-4,6-difluorophenyl | H |
| 1.089 | 3-chloro-4,5-difluorophenyl | H |
| 1.090 | 3,4-methylenedioxyphenyl | H |
| 1.091 | benzo[1,3]drox-5-yl | H |
| 1.092 | 2,3-dihydrobenzo[1,4]dioxin-6-yl | H |
| 1.093 | 2-naphthyl | H |
| 1.094 | 2-pyridyl | H |
| 1.095 | 3-pyridyl | H |
| 1.096 | 4-pyridyl | H |
| 1.097 | 3-chloropyridin-2-yl | H |
| 1.098 | 4-chloropyridin-2-yl | H |
| 1.099 | 5-chloropyridin-2-yl | H |
| 1.100 | 6-chloropyridin-2-yl | H |
| 1.101 | 2-chloropyridin-3-yl | H |
| 1.102 | 4-chloropyridin-3-yl | H |

T-1

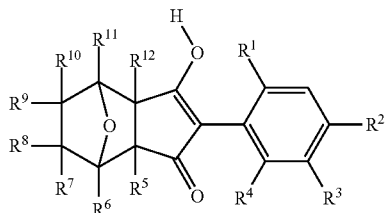

wherein R¹ is methyl, R⁴ is hydrogen, R⁵, R⁶, R⁷, R⁸, R⁹, R¹⁰, R¹¹ and R¹² are hydrogen and R² and R³ are as defined in Table 1.

| Compound Number | R² | R³ |
|---|---|---|
| 1.103 | 2-chloropyridin-4-yl | H |
| 1.104 | 3-chloropyridin-4-yl | H |
| 1.105 | 2-chloropyridin-5-yl | H |
| 1.106 | 3-chloropyridin-5-yl | H |
| 1.107 | 3-methylpyridin-2-yl | H |
| 1.108 | 4-methylpyridin-2-yl | H |
| 1.109 | 5-methylpyridin-2-yl | H |
| 1.110 | 6-methylpyridin-2-yl | H |
| 1.111 | 2-methylpyridin-3-yl | H |
| 1.112 | 4-methylpyridin-3-yl | H |
| 1.113 | 2-methylpyridin-4-yl | H |
| 1.114 | 3-methylpyridin-4-yl | H |
| 1.115 | 2-methylpyridin-5-yl | H |
| 1.116 | 3-methylpyridinyl-5-yl | H |
| 1.117 | 2-trifluoromethylpyridin-5-yl | H |
| 1.118 | 3-trifluoromethylpyridin-5-yl | H |
| 1.119 | 2,6-dichloropyridin-3-yl | H |
| 1.120 | 2-chloro-4-methylpyridin-5-yl | H |
| 1.121 | 6-chloro-2-methylpyridin-3-yl | H |
| 1.122 | 5-chlorothiophen-2-yl | H |
| 1.123 | 2-chlorothiophen-3-yl | H |
| 1.124 | 2,5-dichlorothiophen-3-yl | H |
| 1.125 | 1-methylpyrazol-4-yl | H |
| 1.126 | 4-chloropyrazol-1-yl | H |
| 1.127 | H | phenyl |
| 1.128 | H | 2-fluorophenyl |
| 1.129 | H | 3-fluorophenyl |
| 1.130 | H | 4-fluorophenyl |
| 1.131 | H | 2-chlorophenyl |
| 1.132 | H | 3-chlorophenyl |
| 1.133 | H | 4-chlorophenyl |
| 1.134 | H | 2-bromophenyl |
| 1.135 | H | 3-bromophenyl |
| 1.136 | H | 4-bromophenyl |
| 1.137 | H | 2-methylphenyl |
| 1.138 | H | 3-methylphenyl |
| 1.139 | H | 4-methylphenyl |
| 1.140 | H | 4-ethylphenyl |
| 1.141 | H | 4-isopropylphenyl |
| 1.142 | H | 4-isobutylphenyl |
| 1.143 | H | 4-tert-butylphenyl |
| 1.144 | H | 2-cyanophenyl |
| 1.145 | H | 3-cyanophenyl |
| 1.146 | H | 4-cyanophenyl |
| 1.147 | H | 2-methoxyphenyl |
| 1.148 | H | 3-methoxyphenyl |
| 1.149 | H | 4-methoxyphenyl |
| 1.150 | H | 2-trifluoromethylphenyl |
| 1.151 | H | 3-trifluoromethylphenyl |
| 1.152 | H | 4-trifluoromethylphenyl |
| 1.153 | H | 4-trifludromethoxyphenyl |
| 1.154 | H | 4-difluoromethoxyphenyl |
| 1.155 | H | 4-methylthiophenyl |
| 1.156 | H | 4-methylsulfinylphenyl |
| 1.157 | H | 4-methylsulfonylphenyl |
| 1.158 | H | 4-trifluoromethylthiophenyl |
| 1.159 | H | 4-trifluoromethylsulfinylphenyl |
| 1.160 | H | 4-trifluoromethylsulfonylphenyl |
| 1.161 | H | 2,3-difluorophenyl |
| 1.162 | H | 2,4-difluorophenyl |
| 1.163 | H | 2,5-difluorophenyl |

-continued

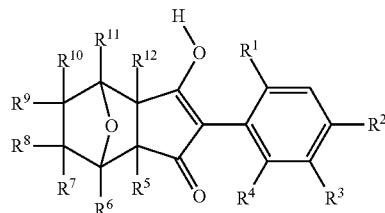

T-1 wherein $R^1$ is methyl, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1.

| Compound Number | $R^2$ | $R^3$ |
|---|---|---|
| 1.164 | H | 2,6-difluorophenyl |
| 1.165 | H | 3,4-difluorophenyl |
| 1.166 | H | 3,5-difluorophenyl |
| 1.167 | H | 2,3-dichlorophenyl |
| 1.168 | H | 2,4-dichlorophenyl |
| 1.169 | H | 2,5-dichlorophenyl |
| 1.170 | H | 2,6-dichlorophenyl |
| 1.171 | H | 3,4-dichlorophenyl |
| 1.172 | H | 3,5-dichlorophenyl |
| 1.173 | H | 2,3,4-trichlorophenyl |
| 1.174 | H | 2,3,5-trichlorophenyl |
| 1.175 | H | 2,3,6-trichlorophenyl |
| 1.176 | H | 2,4,5-trichlorophenyl |
| 1.177 | H | 2,4,6-trichlorophenyl |
| 1.178 | H | 3,4,5-trichlorophenyl |
| 1.179 | H | 2-chloro-3-fluorophenyl |
| 1.180 | H | 2-chloro-4-fluorophenyl |
| 1.181 | H | 2-chloro-4-fluorophenyl |
| 1.182 | H | 2-chloro-4-fluorophenyl |
| 1.183 | H | 3-chloro-2-fluorophenyl |
| 1.184 | H | 3-chloro-4-fluorophenyl |
| 1.185 | H | 3-chloro-5-fluorophenyl |
| 1.186 | H | 4-chloro-2-fluorophenyl |
| 1.187 | H | 4-chloro-3-fluorophenyl |
| 1.188 | H | 5-chloro-2-fluorophenyl |
| 1.189 | H | 4-chloro-2-methylphenyl |
| 1.190 | H | 4-chloro-3-methylphenyl |
| 1.191 | H | 4-chloro-2-trifluoromethylphenyl |
| 1.192 | H | 4-chloro-3-trifluoromethylphenyl |
| 1.193 | H | 4-chloro-2-cyanophenyl |
| 1.194 | H | 4-chloro-3-cyanophenyl |
| 1.195 | H | 4-chloro-2-methoxyphenyl |
| 1.196 | H | 4-chloro-3-methoxyphenyl |
| 1.197 | H | 4-fluoro-2-methylphenyl |
| 1.198 | H | 4-fluoro-3-methylphenyl |
| 1.199 | H | 4-fluoro-2-trifluoromethylphenyl |
| 1.200 | H | 4-fluoro-3-trifluoromethylphenyl |
| 1.201 | H | 2-fluoro-4-trifluoromethylphenyl |
| 1.202 | H | 3-fluoro-4-thfluoromethylphenyl |
| 1.203 | H | 2,3,4-trifluorophenyl |
| 1.204 | H | 2,3,5-trifluorophenyl |
| 1.205 | H | 2,3,6-trifluorophenyl |
| 1.206 | H | 2,4,5-trifluorophenyl |
| 1.207 | H | 2,4,6-trifluorophenyl |
| 1.208 | H | 3,4,5-trifluorophenyl |
| 1.209 | H | 3,4-dichloro-2-fluorophenyl |
| 1.210 | H | 3,4-dichoro-5-fluorophenyl |
| 1.211 | H | 4,5-dichloro-2-fluorophenyl |
| 1.212 | H | 2-chloro-3,4-difluorophenyl |
| 1.213 | H | 2-chloro-4,5-difluorophenyl |
| 1.214 | H | 2-chloro-4,6-difluorophenyl |
| 1.215 | H | 3-chloro-4,5-difluorophenyl |
| 1.216 | H | 3,4-methylenedioxyphenyl |
| 1.217 | H | benzo[1,3]diox-5-yl |
| 1.218 | H | 2,3-dihydrobenzo[1,4]dioxin-6-yl |
| 1.219 | H | 2-naphthyl |
| 1.220 | H | 2-pyridyl |
| 1.221 | H | 3-pyridyl |
| 1.222 | H | 4-pyridyt |
| 1.223 | H | 3-chloropyridin-2-yl |
| 1.224 | H | 4-chloropyridin-2-yl |

-continued

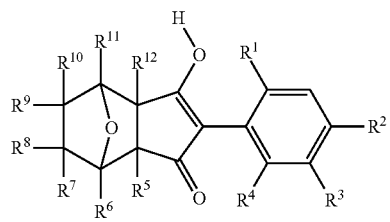

T-1 wherein $R^1$ is methyl, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1.

| Compound Number | $R^2$ | $R^3$ |
|---|---|---|
| 1.225 | H | 5-chloropyridin-2-yl |
| 1.226 | H | 6-chloropyridin-2-yl |
| 1.227 | H | 2-chloropyridin-3-yl |
| 1.228 | H | 4-chloropyridin-3-yl |
| 1.229 | H | 2-chloropyridin-4-yl |
| 1.230 | H | 3-chloropyridin-4-yl |
| 1.231 | H | 2-chloropyridin-5-yl |
| 1.232 | H | 3-chloropyridin-5-yl |
| 1.233 | H | 3-methylpyridin-2-yl |
| 1.234 | H | 4-methylpyridin-2-yl |
| 1.235 | H | 5-methylpyridin-2-yl |
| 1.236 | H | 6-methylpyridin-2-yl |
| 1.237 | H | 2-methylpyridin-3-yl |
| 1.238 | H | 4-methylpyridin-3-yl |
| 1.239 | H | 2-methylpyridin-4-yl |
| 1.240 | H | 3-methylpyridin-4-yl |
| 1.241 | H | 2-methylpyridin-5-yl |
| 1.242 | H | 3-methylpyridinyl-5-yl |
| 1.243 | H | 2-trifluoromethylpyridin-5-yl |
| 1.244 | H | 3-trifluoromethylpyridin-5-yl |
| 1.245 | H | 2,6-dichloropyridin-3-yl |
| 1.246 | H | 2-chloro-4-methylpyridin-5-yl |
| 1.247 | H | 6-chloro-2-methylpyridin-3-yl |
| 1.248 | H | 5-chlorothiophen-2-yl |
| 1.249 | H | 2-chlorothiophen-3-yl |
| 1.250 | H | 2,5-dichlorothiophen-3-yl |
| 1.251 | H | 1-methylpyrazol-4-yl |
| 1.252 | H | 4-chloropyrazol-1-yl |
| 1.253 | $CH_3$ | phenyl |
| 1.254 | $CH_3$ | 2-fluorophenyl |
| 1.255 | $CH_3$ | 3-fluorophenyl |
| 1.256 | $CH_3$ | 4-fluorophenyl |
| 1.257 | $CH_3$ | 2-chlorophenyl |
| 1.258 | $CH_3$ | 3-chlorophenyl |
| 1.259 | $CH_3$ | 4-chlorophenyl |
| 1.260 | $CH_3$ | 2-bromophenyl |
| 1.261 | $CH_3$ | 3-bromophenyl |
| 1.262 | $CH_3$ | 4-bromophenyl |
| 1.263 | $CH_3$ | 2-methylphenyl |
| 1.264 | $CH_3$ | 3-methylphenyl |
| 1.265 | $CH_3$ | 4-methylphenyl |
| 1.266 | $CH_3$ | 4-ethylphenyl |
| 1.267 | $CH_3$ | 4-isopropylphenyl |
| 1.268 | $CH_3$ | 4-isobutylphenyl |
| 1.269 | $CH_3$ | 4-tert-butylphenyl |
| 1.270 | $CH_3$ | 2-cyanophenyl |
| 1.271 | $CH_3$ | 3-cyanophenyl |
| 1.272 | $CH_3$ | 4-cyanophenyl |
| 1.273 | $CH_3$ | 2-methoxyphenyl |
| 1.274 | $CH_3$ | 3-methoxyphenyl |
| 1.275 | $CH_3$ | 4-methoxyphenyl |
| 1.276 | $CH_3$ | 2-trifluoromethylphenyl |
| 1.277 | $CH_3$ | 3-trifluoromethylphenyl |
| 1.278 | $CH_3$ | 4-trifluoromethylphenyl |
| 1.279 | $CH_3$ | 4-triflubromethoxyphenyl |
| 1.280 | $CH_3$ | 4-difluoromethoxyphenyl |
| 1.281 | $CH_3$ | 4-methylthiophenyl |
| 1.282 | $CH_3$ | 4-methylsulfinylphenyl |
| 1.283 | $CH_3$ | 4-methylsulfonylphenyl |
| 1.284 | $CH_3$ | 4-trifluoromethylthiophenyl |
| 1.285 | $CH_3$ | 4-trifluoromethylsulfinylphenyl |

-continued

T-1

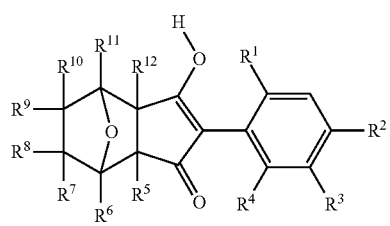

wherein $R^1$ is methyl, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1.

| Compound Number | $R^2$ | $R^3$ |
|---|---|---|
| 1.286 | $CH_3$ | 4-trifluoromethylsulfonylphenyl |
| 1.287 | $CH_3$ | 2,3-difluorophenyl |
| 1.288 | $CH_3$ | 2,4-difluorophenyl |
| 1.289 | $CH_3$ | 2,5-difluorophenyl |
| 1.290 | $CH_3$ | 2,6-difluorophenyl |
| 1.291 | $CH_3$ | 3,4-difluorophenyl |
| 1.292 | $CH_3$ | 3,5-difluorophenyl |
| 1.293 | $CH_3$ | 2,3-dichlorophenyl |
| 1.294 | $CH_3$ | 2,4-dichlorophenyl |
| 1.295 | $CH_3$ | 2,5-dichlorophenyl |
| 1.296 | $CH_3$ | 2,6-dichlorophenyl |
| 1.297 | $CH_3$ | 3,4-dichlorophenyl |
| 1.298 | $CH_3$ | 3,5-dichlorophenyl |
| 1.299 | $CH_3$ | 2,3,4-trichlorophenyl |
| 1.300 | $CH_3$ | 2,3,5-trichlorophenyl |
| 1.301 | $CH_3$ | 2,3,6-trichlorophenyl |
| 1.302 | $CH_3$ | 2,4,5-trichlorophenyl |
| 1.303 | $CH_3$ | 2,4,6-trichlorophenyl |
| 1.304 | $CH_3$ | 3,4,5-trichlorophenyl |
| 1.305 | $CH_3$ | 2-chloro-3-fluorophenyl |
| 1.306 | $CH_3$ | 2-chloro-4-fluorophenyl |
| 1.307 | $CH_3$ | 2-chloro-4-fluorophenyl |
| 1.308 | $CH_3$ | 2-chloro-4-fluorophenyl |
| 1.309 | $CH_3$ | 3-chloro-2-fluorophenyl |
| 1.310 | $CH_3$ | 3-chloro-4-fluorophenyl |
| 1.311 | $CH_3$ | 3-chloro-5-fluorophenyl |
| 1.312 | $CH_3$ | 4-chloro-2-fluorophenyl |
| 1.313 | $CH_3$ | 4-chloro-3-fluorophenyl |
| 1.314 | $CH_3$ | 5-chloro-2-fluorophenyl |
| 1.315 | $CH_3$ | 4-chloro-2-methylphenyl |
| 1.316 | $CH_3$ | 4-chloro-3-methylphenyl |
| 1.317 | $CH_3$ | 4-chloro-2-trifluoromethylphenyl |
| 1.318 | $CH_3$ | 4-chloro-3-trifluoromethylphenyl |
| 1.319 | $CH_3$ | 4-chloro-2-cyanophenyl |
| 1.320 | $CH_3$ | 4-chloro-3-cyanophenyl |
| 1.321 | $CH_3$ | 4-chloro-2-methoxyphenyl |
| 1.322 | $CH_3$ | 4-chloro-3-methoxyphenyl |
| 1.323 | $CH_3$ | 4-fluoro-2-methylphenyl |
| 1.324 | $CH_3$ | 4-fluoro-3-methylphenyl |
| 1.325 | $CH_3$ | 4-fluoro-2-trifluoromethylphenyl |
| 1.326 | $CH_3$ | 4-fluoro-3-trifluoromethylphenyl |
| 1.327 | $CH_3$ | 2-fluoro-4-trifluoromethylphenyl |
| 1.328 | $CH_3$ | 3-fluoro-4-trifluoromethylphenyl |
| 1.329 | $CH_3$ | 2,3,4-trifluorophenyl |
| 1.330 | $CH_3$ | 2,3,5-trifluorophenyl |
| 1.331 | $CH_3$ | 2,3,6-trifluorophenyl |
| 1.332 | $CH_3$ | 2,4,5-trifluorophenyl |
| 1.333 | $CH_3$ | 2,4,6-trifluorophenyl |
| 1.334 | $CH_3$ | 3,4,5-trifluorophenyl |
| 1.335 | $CH_3$ | 3,4-dichloro-2-fluorophenyl |
| 1.336 | $CH_3$ | 3,4-dichoro-5-fluorophenyl |
| 1.337 | $CH_3$ | 4,5-dichloro-2-fluorophenyl |
| 1.338 | $CH_3$ | 2-chloro-3,4-difluorophenyl |
| 1.339 | $CH_3$ | 2-chloro-4,5-difluorophenyl |
| 1.340 | $CH_3$ | 2-chloro-4,6-difluorophenyl |
| 1.341 | $CH_3$ | 3-chloro-4,5-difluorophenyl |
| 1.342 | $CH_3$ | 3,4-methylenedioxyphenyl |
| 1.343 | $CH_3$ | benzo[1,3]diox-5-yl |
| 1.344 | $CH_3$ | 2,3-dihydrobenzo[1,4]dioxin-6-yl |
| 1.345 | $CH_3$ | 2-naphthyl |
| 1.346 | $CH_3$ | 2-pyridyl |

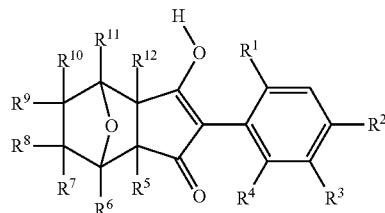

T-1 wherein $R^1$ is methyl, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1.

| Compound Number | $R^2$ | $R^3$ |
|---|---|---|
| 1.347 | CH$_3$ | 3-pyridyl |
| 1.348 | CH$_3$ | 4-pyridyl |
| 1.349 | CH$_3$ | 3-chloropyridin-2-yl |
| 1.350 | CH$_3$ | 4-chloropyridin-2-yl |
| 1.351 | CH$_3$ | 5-chloropyridin-2-yl. |
| 1.352 | CH$_3$ | 6-chloropyridin-2-yl |
| 1.353 | CH$_3$ | 2-chloropyridin-3-yl |
| 1.354 | CH$_3$ | 4-chloropyridin-3-yl |
| 1.355 | CH$_3$ | 2-chloropyridin-4-yl |
| 1.356 | CH$_3$ | 3-chloropyridin-4-yl |
| 1.357 | CH$_3$ | 2-chloropyridin-5-yl |
| 1.358 | CH$_3$ | 3-chloropyridin-5-yl |
| 1.359 | CH$_3$ | 3-methylpyridin-2-yl |
| 1.360 | CH$_3$ | 4-methylpyridin-2-yl |
| 1.361 | CH$_3$ | 5-methylpyridin-2-yl |
| 1.362 | CH$_3$ | 6-methylpyridin-2-yl |
| 1.363 | CH$_3$ | 2-methylpyridin-3-yl |
| 1.364 | CH$_3$ | 4-methylpyridin-3-yl |
| 1.365 | CH$_3$ | 2-methylpyridin-4-yl |
| 1.366 | CH$_3$ | 3-methylpyridin-4-yl |
| 1.367 | CH$_3$ | 2-methylpyridin-5-yl |
| 1.368 | CH$_3$ | 3-methylpyridinyl-5-yl |
| 1.369 | CH$_3$ | 2-trifluoromethylpyridin-5-yl |
| 1.370 | CH$_3$ | 3-trifluoromethylpyridin-5-yl |
| 1.371 | CH$_3$ | 2,6-dichloropyridin-3-yl |
| 1.372 | CH$_3$ | 2-chloro-4-methylpyridin-5-yl |
| 1.373 | CH$_3$ | 6-chloro-2-methylpyridin-3-yl |
| 1.374 | CH$_3$ | 5-chlorothiophen-2-yl |
| 1.375 | CH$_3$ | 2-chlorothiophen-3-yl |
| 1.376 | CH$_3$ | 2,5-dichlorothiophen-3-yl |
| 1.377 | CH$_3$ | 1-methylpyrazol-4-yl |
| 1.378 | CH$_3$ | 4-chloropyrazol-1-yl |

Table 2 covers 378 compounds of the type T-1 wherein $R^1$ is methyl, $R^4$ is hydrogen, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 3 covers 378 compounds of the type T-1 wherein $R^1$ is methyl, $R^4$ is hydrogen, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 4 covers 378 compounds of the type T-1 wherein $R^1$ is methyl, $R^4$ is hydrogen, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 5 covers 378 compounds of the type T-1 wherein $R^1$ is methyl, $R^4$ is hydrogen, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 6 covers 378 compounds of the type T-1 wherein $R^1$ is methyl, $R^4$ is hydrogen, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 7 covers 378 compounds of the type T-1 wherein $R^1$ is methyl, $R^4$ is hydrogen, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 8 covers 378 compounds of the type T-1 wherein $R^1$ is methyl, $R^4$ is hydrogen, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 9 covers 378 compounds of the type T-1 wherein $R^1$ is methyl, $R^4$ is hydrogen, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 10 covers 378 compounds of the type T-1 wherein $R^1$ is methyl, $R^4$ is hydrogen, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 11 covers 378 compounds of the type T-1 wherein $R^1$ is methyl, $R^4$ is hydrogen, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 12 covers 378 compounds of the type T-1 wherein $R^1$ is methyl, $R^4$ is hydrogen, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 13 covers 378 compounds of the type T-1 wherein $R^1$ is ethyl, $R^4$ is hydrogen, $R^5$, $R^6$, $R^7$, $R^5$, $R^9$, $R^{10}$, $R^{11}$ and $R^{12}$ are hydrogen and $R^2$ and $R^3$ are as defined in Table 1.

Table 14 covers 378 compounds of the type T-1 wherein $R^1$ is ethyl, $R^4$ is hydrogen, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 15 covers 378 compounds of the type T-1 wherein $R^1$ is ethyl, $R^4$ is hydrogen, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 16 covers 378 compounds of the type T-1 wherein $R^1$ is ethyl, $R^4$ is hydrogen, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 17 covers 378 compounds of the type T-1 wherein $R^1$ is ethyl, $R^4$ is hydrogen, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 18 covers 378 compounds of the type T-1 wherein $R^1$ is ethyl, $R^4$ is hydrogen, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 19 covers 378 compounds of the type T-1 wherein $R^1$ is ethyl, $R^4$ is hydrogen, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 20 covers 378 compounds of the type T-1 wherein $R^1$ is ethyl, $R^4$ is hydrogen, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 21 covers 378 compounds of the type T-1 wherein $R^1$ is ethyl, $R^4$ is hydrogen, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 22 covers 378 compounds of the type T-1 wherein $R^1$ is ethyl, $R^4$ is hydrogen, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 23 covers 378 compounds of the type T-1 wherein $R^1$ is ethyl, $R^4$ is hydrogen, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 24 covers 378 compounds of the type T-1 wherein $R^1$ is ethyl, $R^4$ is hydrogen, $R^5$ is hydrogen, $R^6$ is methyl $R^7$, $R^8$, $R^9$, $R^{10}$, $R^{11}$ are hydrogen, $R^{12}$ is methyl, $R^2$ is hydrogen and $R^2$ and $R^3$ are as defined in Table 1.

Table 25 covers 378 compounds of the type T-1 wherein $R^1$ and $R^4$ are methyl, $R^5$, $R^6$, $R^7$, $R^8$, $R^9$, $R^{10}$, $R^{11}$ and $R^{12}$ are hydrogen and $R^2$ and $R^3$ are as defined in Table 1.

Table 26 covers 378 compounds of the type T-1 wherein $R^1$ and $R^4$ are methyl, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 27 covers 378 compounds of the type T-1 wherein $R^1$ and $R^4$ are methyl, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 28 covers 378 compounds of the type T-1 wherein $R^1$ and $R^4$ are methyl, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 29 covers 378 compounds of the type T-1 wherein $R^1$ and $R^4$ are methyl, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 30 covers 378 compounds of the type T-1 wherein $R^1$ and $R^4$ are methyl, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 31 covers 378 compounds of the type T-1 wherein $R^1$ and $R^4$ are methyl, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 32 covers 378 compounds of the type T-1 wherein $R^1$ and $R^4$ are methyl, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 33 covers 378 compounds of the type T-1 wherein $R^1$ and $R^4$ are methyl, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 34 covers 378 compounds of the type T-1 wherein $R^1$ and $R^4$ are methyl, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 35 covers 378 compounds of the type T-1 wherein $R^1$ and $R^4$ are methyl, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 36 covers 378 compounds of the type T-1 wherein $R^1$ and $R^4$ are methyl, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 37 covers 378 compounds of the type T-1 wherein $R^1$ and $R^4$ are ethyl, $R^5$, $R^6$, $R^7$, $R^8$, $R^9$, $R^{10}$, $R^{11}$ and $R^{12}$ are hydrogen and $R^2$ and $R^3$ are as defined in Table 1.

Table 38 covers 378 compounds of the type T-1 wherein $R^1$ and $R^4$ are ethyl, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 39 covers 378 compounds of the type T-1 wherein $R^1$ and $R^4$ are ethyl, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 40 covers 378 compounds of the type T-1 wherein $R^1$ and $R^4$ are ethyl, $R^5$ is hydrogen, $R^6$ is methoxymethyl, $R^7$, $R^8$, $R^9$, $R^{10}$, $R^{11}$ and $R^{12}$ are hydrogen and $R^2$ and $R^1$ are as defined in Table 1.

Table 41 covers 378 compounds of the type T-1 wherein $R^1$ and $R^4$ are ethyl, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 42 covers 378 compounds of the type T-1 wherein $R^1$ and $R^4$ are ethyl, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 43 covers 378 compounds of the type T-1 wherein $R^1$ and $R^4$ are ethyl, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 44 covers 378 compounds of the type T-1 wherein $R^1$ and $R^4$ are ethyl, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 45 covers 378 compounds of the type T-1 wherein $R^1$ and $R^4$ are ethyl, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 46 covers 378 compounds of the type T-1 wherein $R^1$ and $R^4$ are ethyl, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 47 covers 378 compounds of the type T-1 wherein $R^1$ and $R^4$ are ethyl, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 48 covers 378 compounds of the type T-1 wherein $R^1$ and $R^4$ are ethyl, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 49 covers 378 compounds of the type T-1 wherein $R^1$ is difluoromethoxy, $R^4$ is hydrogen, $R^5$, $R^6$, $R^8$, $R^9$, $R^{10}$, $R^{11}$ and $R^{12}$ are hydrogen and $R^2$ and $R^3$ are as defined in Table 1.

Table 50 covers 378 compounds of the type T-1 wherein $R^1$ is difluoromethoxy, $R^4$ is hydrogen, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 51 covers 378 compounds of the type T-1 wherein $R^1$ is difluoromethoxy, $R^4$ is hydrogen, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 52 covers 378 compounds of the type T-1 wherein $R^1$ is difluoromethoxy, $R^4$ is hydrogen, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 53 covers 378 compounds of the type T-1 wherein $R^1$ is difluoromethoxy, $R^4$ is hydrogen, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 54 covers 378 compounds of the type T-1 wherein $R^1$ is difluoromethoxy, $R^4$ is hydrogen, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 55 covers 378 compounds of the type T-1 wherein $R^1$ is difluoromethoxy, $R^4$ is hydrogen, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 56 covers 378 compounds of the type T-1 wherein $R^1$ is difluoromethoxy, $R^4$ is hydrogen, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 57 covers 378 compounds of the type T-1 wherein $R^1$ is difluoromethoxy, $R^4$ is hydrogen, $R^5$, $R^6$, $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 58 covers 378 compounds of the type T-1 wherein $R^1$ is difluoromethoxy, $R^4$ is hydrogen, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 59 covers 378 compounds of the type T-1 wherein $R^1$ is difluoromethoxy, $R^4$ is hydrogen, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 60 covers 378 compounds of the type T-1 wherein $R^1$ is difluoromethoxy, $R^4$ is hydrogen, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 61 covers 378 compounds of the type T-1 wherein $R^1$ is trifluoromethoxy, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1.

Table 62 covers 378 compounds of the type T-1 wherein $R^1$ is trifluoromethoxy, $R^4$ is hydrogen, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 63 covers 378 compounds of the type T-1 wherein $R^1$ is trifluoromethoxy, $R^4$ is hydrogen, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 64 covers 378 compounds of the type T-1 wherein $R^1$ is trifluoromethoxy, $R^4$ is hydrogen, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 65 covers 378 compounds of the type T-1 wherein $R^1$ is trifluoromethoxy, $R^4$ is hydrogen, $R^5$ is hydrogen, $R^6$ is ethoxymethyl $R^7$, $R^8$, $R^9$, $R^{10}$, $R^{11}$, and $R^{12}$ are hydrogen and $R^2$ and $R^3$ are as defined in Table 1.

Table 66 covers 378 compounds of the type T-1 wherein $R^1$ is trifluoromethoxy, $R^4$ is hydrogen, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 67 covers 378 compounds of the type T-1 wherein $R^1$ is trifluoromethoxy, $R^4$ is hydrogen, $R^5$, $R^6$ and $R^7$ are hydrogen, $R^8$ is methyl $R^9$, $R^{10}$, $R^{11}$ and $R^{12}$ are hydrogen and $R^2$ and $R^3$ are as defined in Table 1.

Table 68 covers 378 compounds of the type T-1 wherein $R^1$ is trifluoromethoxy, $R^4$ is hydrogen, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 69 covers 378 compounds of the type T-1 wherein $R^1$ is trifluoromethoxy, $R^4$ is hydrogen, $R^5$, $R^8$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 70 covers 378 compounds of the type T-1 wherein $R^1$ is trifluoromethoxy, $R^4$ is hydrogen, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 71 covers 378 compounds of the type T-1 wherein $R^1$ is trifluoromethoxy, $R^4$ is hydrogen, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 72 covers 378 compounds of the type T-1 wherein $R^1$ is trifluoromethoxy, $R^4$ is hydrogen, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 73 covers 378 compounds of the type T-1 wherein $R^1$ is cyclopropyl, $R^4$ is hydrogen, $R^5$, $R^6$, $R^7$, $R^8$, $R^9$, $R^{10}$, $R^{11}$ and $R^2$ are hydrogen and $R^2$ and $R^3$ are as defined in Table 1

Table 74 covers 378 compounds of the type T-1 wherein $R^1$ is cyclopropyl, $R^4$ is hydrogen, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 75 covers 378 compounds of the type T-1 wherein $R^1$ is cyclopropyl, $R^4$ is hydrogen, $R^5$ is hydrogen, $R^6$ is ethyl, $R^7$, $R^8$, $R^9$, $R^{10}$, $R^{11}$ and $R^{12}$ are hydrogen and $R^2$ and $R^3$ are as defined in Table 1.

Table 76 covers 378 compounds of the type T-1 wherein $R^1$ is cyclopropyl, $R^4$ is hydrogen, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 77 covers 378 compounds of the type T-1 wherein $R^1$ is cyclopropyl, $R^4$ is hydrogen, $R^5$ is hydrogen, $R^6$ is ethoxymethyl $R^7$, $R^8$, $R^9$, $R^{10}$, $R^{11}$ and $R^{12}$ are hydrogen and $R^2$ and $R^3$ are as defined in Table 1.

Table 78 covers 378 compounds of the type T-1 wherein $R^1$ is cyclopropyl, $R^4$ is hydrogen, $R^5$ is hydrogen, $R^6$ is methoxyethyl $R^7$, $R^8$, $R^9$, $R^{10}$, $R^{11}$ and $R^{12}$ are hydrogen and $R^2$ and $R^3$ are as defined in Table 1.

Table 79 covers 378 compounds of the type T-1 wherein $R^1$ is cyclopropyl, $R^4$ is hydrogen, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 80 covers 378 compounds of the type T-1 wherein $R^1$ is cyclopropyl, $R^4$ is hydrogen, $R^5$, $R^6$ and $R^7$ are hydrogen, $R^8$ is ethyl, $R^9$, $R^{10}$, $R^{11}$, and $R^{12}$ are hydrogen and $R^2$ and $R^3$ are as defined in Table 1.

Table 81 covers 378 compounds of the type T-1 wherein $R^1$ is cyclopropyl, $R^4$ is hydrogen, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 82 covers 378 compounds of the type T-1 wherein $R^1$ is cyclopropyl, $R^4$ is hydrogen, $R^5$, $R^6$ and $R^7$ are hydrogen, $R^8$ is ethoxymethyl, $R^9$, $R^{10}$, $R^{11}$ and $R^{12}$ are hydrogen and $R^2$ and $R^3$ are as defined in Table 1.

Table 83 covers 378 compounds of the type T-1 wherein $R^1$ is cyclopropyl, $R^4$ is hydrogen, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 84 covers 378 compounds of the type T-1 wherein $R^1$ is cyclopropyl, $R^4$ is hydrogen, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 85 covers 378 compounds of the type T-1 wherein $R^1$ is chlorine, $R^4$ is hydrogen, $R^5$, $R^6$, $R^7$, $R^8$, $R^9$, $R^{10}$, $R^{11}$ and $R^{12}$ are hydrogen and $R^2$ and $R^3$ are as defined in Table 1

Table 86 covers 378 compounds of the type T-1 wherein $R^1$ is chlorine, $R^4$ is hydrogen, $R^5$ is hydrogen, $R^6$ is methyl, $R^7$, $R^8$, $R^9$, $R^{10}$, $R^{11}$ and $R^{12}$ are hydrogen and $R^2$ and $R^3$ are as defined in Table 1.

Table 87 covers 378 compounds of the type T-1 wherein $R^1$ is chlorine, $R^4$ is hydrogen, $R^5$ is hydrogen, $R^6$ is ethyl, $R^7$, $R^8$, $R^9$, $R^{10}$, $R^{11}$ and $R^{12}$ are hydrogen and $R^5$ and $R^3$ are as defined in Table 1.

Table 88 covers 378 compounds of the type T-1 wherein $R^1$ is chlorine, $R^4$ is hydrogen, $R^5$ is hydrogen, $R^6$ is methoxymethyl, $R^7$, $R^8$, $R^9$, $R^{10}$, $R^{11}$ and $R^{12}$ are hydrogen and $R^2$ and $R^3$ are as defined in Table 1.

Table 89 covers 378 compounds of the type T-1 wherein $R^1$ is chlorine, $R^4$ is hydrogen, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 90 covers 378 compounds of the type T-1 wherein $R^1$ is chlorine, $R^4$ is hydrogen, $R^5$ is hydrogen, $R^6$ is methoxyethyl, $R^7$, $R^8$, $R^9$, $R^{10}$, $R^{11}$ and $R^{12}$ are hydrogen and $R^2$ and $R^3$ are as defined in Table 1.

Table 91 covers 378 compounds of the type T-1 wherein $R^1$ is chlorine, $R^4$ is hydrogen, $R^5$, $R^6$ and $R^7$ are hydrogen, $R^8$ is methyl, $R^9$, $R^{10}$, $R^{11}$ and $R^{12}$ are hydrogen and $R^2$ and $R^3$ are as defined in Table 1.

Table 92 covers 378 compounds of the type T-1 wherein $R^1$ is chlorine, $R^4$ is hydrogen, $R^5$, $R^6$ and $R^7$ are hydrogen, $R^8$ is ethyl, $R^9$, $R^{10}$, $R^{11}$ and $R^{12}$ are hydrogen and $R^2$ and $R^3$ are as defined in Table 1.

Table 93 covers 378 compounds of the type T-1 wherein $R^1$ is chlorine, $R^4$ is hydrogen, $R^5$, $R^6$ and $R^7$ are hydrogen, $R^8$ is methoxymethyl, $R^9$, $R^{10}$, $R^{11}$ and $R^{12}$ are hydrogen and $R^2$ and $R^3$ are as defined in Table 1.

Table 94 covers 378 compounds of the type T-1 wherein $R^1$ is chlorine, $R^4$ is hydrogen, $R^5$, $R^6$ and $R^7$ are hydrogen, $R^5$ is ethoxymethyl, $R^9$, $R^{10}$, $R^{11}$ and $R^{12}$ are hydrogen and $R^2$ and $R^3$ are as defined in Table 1.

Table 95 covers 378 compounds of the type T-1 wherein $R^1$ is chlorine, $R^4$ is hydrogen, $R^5$, $R^6$ and $R^7$ are hydrogen, $R^8$ is methoxyethyl, $R^9$, $R^{10}$, $R^{11}$ and $R^{12}$ are hydrogen and $R^2$ and $R^3$ are as defined in Table 1.

Table 96 covers 378 compounds of the type T-1 wherein $R^1$ is chlorine, $R^4$ is hydrogen, $R^5$ is hydrogen, $R^6$ is methyl, $R^7$, $R^8$, $R^9$, $R^{10}$ are hydrogen, $R^{11}$ is methyl, $R^{12}$ is hydrogen and $R^2$ and $R^3$ are as defined in Table 1.

Table 97 covers 378 compounds of the type T-2

T-2 wherein $R^1$ is methyl, $R^4$ is hydrogen, $R^5$, $R^6$, $R^8$, $R^9$, $R^{11}$ and $R^{12}$ are hydrogen and $R^2$ and $R^3$ are as defined in Table 1.

Table 98 covers 378 compounds of the type T-2 wherein $R^1$ is methyl, $R^4$ is hydrogen, $R^5$ is hydrogen, $R^6$ is methyl, $R^8$, $R^9$, $R^{11}$ and $R^{12}$ are hydrogen and $R^2$ and $R^3$ are as defined in Table 1.

Table 99 covers 378 compounds of the type T-2 wherein $R^1$ is methyl, $R^4$ is hydrogen, $R^5$ is hydrogen, $R^6$ is ethyl, $R^8$, $R^9$, $R^{11}$ and $R^{12}$ are hydrogen and $R^2$ and $R^3$ are as defined in Table 1.

Table 100 covers 378 compounds of the type T-2 wherein $R^1$ is methyl, $R^4$ is hydrogen, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 101 covers 378 compounds of the type T-2 wherein $R^1$ is methyl, $R^4$ is hydrogen, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 102 covers 378 compounds of the type T-2 wherein $R^1$ is methyl, $R^4$ is hydrogen, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 103 covers 378 compounds of the type T-2 wherein $R^1$ is methyl, $R^4$ is hydrogen, $R^5$ and $R^6$ are hydrogen, $R^8$ is methyl, $R^9$, $R^{11}$ and $R^{12}$ are hydrogen and $R^2$ and $R^3$ are as defined in Table 1.

Table 104 covers 378 compounds of the type T-2 wherein $R^1$ is methyl, $R^4$ is hydrogen, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 105 covers 378 compounds of the type T-2 wherein $R^1$ is methyl, $R^4$ is hydrogen, $R^5$ and $R^6$ are hydrogen, $R^8$ is methoxymethyl, $R^9$, $R^{11}$ and $R^2$ are hydrogen and $R^2$ and $R^3$ are as defined in Table 1.

Table 106 covers 378 compounds of the type T-2 wherein $R^1$ is methyl, $R^4$ is hydrogen, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 107 covers 378 compounds of the type T-2 wherein $R^1$ is methyl, $R^4$ is hydrogen, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 108 covers 378 compounds of the type T-2 wherein $R^1$ is methyl, $R^4$ is hydrogen, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Table 109 covers 378 compounds of the type T-2 wherein $R^1$ is ethyl, $R^4$ is hydrogen, $R^5$, $R^6$, $R^8$, $R^9$, $R^{11}$ and $R^{12}$ are hydrogen and $R^2$ and $R^1$ are as defined in Table 1.

Table 110 covers 378 compounds of the type T-2 wherein $R^1$ is ethyl, $R^4$ is hydrogen, $R^5$ is hydrogen, $R^6$ is methyl, $R^8$, $R^9$, $R^{11}$ and $R^{12}$ are hydrogen and $R^2$ and $R^3$ are as defined in Table 1.

Table 111 covers 378 compounds of the type T-2 wherein $R^1$ is ethyl, $R^4$ is hydrogen, $R^5$ is hydrogen, $R^6$ is ethyl, $R^8$, $R^9$, $R^{11}$ and $R^2$ are hydrogen and $R^2$ and $R^3$ are as defined in Table 1.

Table 112 covers 378 compounds of the type T-2 wherein $R^1$ is ethyl, $R^4$ is hydrogen, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 113 covers 378 compounds of the type T-2 wherein $R^1$ is ethyl, $R^4$ is hydrogen, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 114 covers 378 compounds of the type T-2 wherein $R^1$ is ethyl, $R^4$ is hydrogen, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 115 covers 378 compounds of the type T-2 wherein $R^1$ is ethyl, $R^4$ is hydrogen, $R^5$ and $R^6$ are hydrogen, $R^8$ is methyl, $R^9$, $R^{11}$ and $R^{12}$ are hydrogen and $R^2$ and $R^3$ are as defined in Table 1.

Table 116 covers 378 compounds of the type T-2 wherein $R^1$ is ethyl, $R^4$ is hydrogen, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 117 covers 378 compounds of the type T-2 wherein $R^1$ is ethyl, $R^4$ is hydrogen, $R^5$ and $R^6$ are hydrogen, $R^8$ is methoxy methyl, $R^9$, $R^{11}$ and $R^{12}$ are hydrogen and $R^2$ and $R^3$ are as defined in Table 1.

Table 118 covers 378 compounds of the type T-2 wherein $R^1$ is ethyl, $R^4$ is hydrogen, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 119 covers 378 compounds of the type T-2 wherein $R^1$ is ethyl, $R^4$ is hydrogen, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 120 covers 378 compounds of the type T-2 wherein $R^1$ is ethyl, $R^4$ is hydrogen, $R^5$ is hydrogen, $R^6$ is methyl, $R^7$ and $R^9$ are hydrogen, $R^{11}$ is methyl, $R^{12}$ is hydrogen and $R^2$ and $R^3$ are as defined in Table 1.

Table 121 covers 378 compounds of the type T-2 wherein $R^1$ and $R^4$ are methyl, $R^5$, $R^6$, $R^8$, $R^9$, $R^{11}$ and $R^{12}$ are hydrogen and $R^2$ and $R^3$ are as defined in Table 1.

Table 122 covers 378 compounds of the type T-2 wherein $R^1$ and $R^4$ are methyl, $R^5$ is hydrogen, $R^6$ is methyl, $R^8$, $R^9$, $R^{11}$ and $R^{12}$ are hydrogen and $R^2$ and $R^3$ are as defined in Table 1.

Table 123 covers 378 compounds of the type T-2 wherein $R^1$ and $R^4$ are methyl, $R^5$ is hydrogen, $R^6$ is ethyl, $R^8$, $R^9$, $R^{11}$ and $R^{12}$ are hydrogen and $R^2$ and $R^3$ are as defined in Table 1.

Table 124 covers 378 compounds of the type T-2 wherein $R^1$ and $R^4$ are methyl, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 125 covers 378 compounds of the type T-2 wherein $R^1$ and $R^4$ are methyl, $R^5$ is hydrogen, $R^6$ is ethoxymethyl, $R^7$, $R^8$, $R^9$, $R^{10}$, $R^{11}$ and $R^{12}$ are hydrogen and $R^2$ and $R^3$ are as defined in Table 1.

Table 126 covers 378 compounds of the type T-2 wherein $R^1$ and $R^4$ are methyl, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 127 covers 378 compounds of the type T-2 wherein $R^1$ and $R^4$ are methyl, $R^5$ and $R^6$ are hydrogen, $R^8$ is methyl, $R^9$, $R^{11}$ and $R^{12}$ are hydrogen and $R^2$ and $R^3$ are as defined in Table 1.

Table 128 covers 378 compounds of the type T-2 wherein $R^1$ and $R^4$ are methyl, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 129 covers 378 compounds of the type T-2 wherein $R^1$ and $R^4$ are methyl, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 130 covers 378 compounds of the type T-2 wherein $R^1$ and $R^4$ are methyl, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 131 covers 378 compounds of the type T-2 wherein $R^1$ and $R^4$ are methyl, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 132 covers 378 compounds of the type T-2 wherein $R^1$ and $R^4$ are methyl, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Table 133 covers 378 compounds of the type T-2 wherein $R^1$ and $R^4$ are ethyl, $R^5$, $R^6$, $R^8$, $R^9$, $R^{11}$ and $R^{12}$ are hydrogen and $R^2$ and $R^3$ are as defined in Table 1.

Table 134 covers 378 compounds of the type T-2 wherein $R^1$ and $R^4$ are ethyl, $R^5$ is hydrogen, $R^6$ is methyl, $R^8$, $R^9$, $R^{11}$ and $R^{12}$ are hydrogen and $R^2$ and $R^3$ are as defined in Table 1.

Table 135 covers 378 compounds of the type T-2 wherein $R^1$ and $R^4$ are ethyl, $R^5$ is hydrogen, $R^6$ is ethyl, $R^8$, $R^9$, $R^{11}$ and $R^{12}$ are hydrogen and $R^2$ and $R^3$ are as defined in Table 1.

Table 136 covers 378 compounds of the type T-2 wherein $R^1$ and $R^4$ are ethyl, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 137 covers 378 compounds of the type T-2 wherein $R^1$ and $R^4$ are ethyl, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 138 covers 378 compounds of the type T-2 wherein $R^1$ and $R^4$ are ethyl, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 139 covers 378 compounds of the type T-2 wherein $R^1$ and $R^4$ are ethyl, $R^5$ and $R^6$ are hydrogen, $R^8$ is methyl, $R^9$, $R^{11}$ and $R^{12}$ are hydrogen and $R^2$ and $R^3$ are as defined in Table 1.

Table 140 covers 378 compounds of the type T-2 wherein $R^1$ and $R^4$ are ethyl, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 141 covers 378 compounds of the type T-2 wherein $R^1$ and $R^4$ are ethyl, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 142 covers 378 compounds of the type T-2 wherein $R^1$ and $R^4$ are ethyl, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 143 covers 378 compounds of the type T-2 wherein $R^1$ and $R^4$ are ethyl, $R^5$ and $R^6$ and are hydrogen, $R^8$ is methoxyethyl, $R^9$, $R^{11}$ and $R^{12}$ are hydrogen and $R^2$ and $R^3$ are as defined in Table 1.

Table 144 covers 378 compounds of the type T-2 wherein $R^1$ and $R^4$ are ethyl, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Table 145 covers 378 compounds of the type T-2 wherein $R^1$ is difluoromethoxy, $R^4$ is hydrogen, $R^5$, $R^6$, $R^8$, $R^9$, $R^{11}$ and $R^{12}$ are hydrogen and $R^2$ and $R^3$ are as defined in Table 1

Table 146 covers 378 compounds of the type T-2 wherein $R^1$ is difluoromethoxy, $R^4$ is hydrogen, $R^5$ is hydrogen, $R^6$ is methyl, $R^8$, $R^9$, $R^{11}$ and $R^{12}$ are hydrogen and $R^2$ and $R^3$ are as defined in Table 1.

Table 147 covers 378 compounds of the type T-2 wherein $R^1$ is difluoromethoxy, $R^4$ is hydrogen, $R^5$ is hydrogen, $R^6$ is ethyl, $R^8$, $R^9$, $R^{11}$ and $R^{12}$ are hydrogen and $R^2$ and $R^3$ are as defined in Table 1.

Table 148 covers 378 compounds of the type T-2 wherein $R^1$ is difluoromethoxy, $R^4$ is hydrogen, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 149 covers 378 compounds of the type T-2 wherein $R^1$ is difluoromethoxy, $R^4$ is hydrogen, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 150 covers 378 compounds of the type T-2 wherein $R^1$ is difluoromethoxy, $R^4$ is hydrogen, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 151 covers 378 compounds of the type T-2 wherein $R^1$ is difluoromethoxy, $R^4$ is hydrogen, $R^5$ and $R^6$ are hydrogen, $R^5$ is methyl, $R^9$, $R^{11}$ and $R^{12}$ are hydrogen and $R^2$ and $R^3$ are as defined in Table 1.

Table 152 covers 378 compounds of the type T-2 wherein $R^1$ is difluoromethoxy, $R^4$ is hydrogen, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 153 covers 378 compounds of the type T-2 wherein $R^1$ is difluoromethoxy, $R^4$ is hydrogen, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 154 covers 378 compounds of the type T-2 wherein $R^1$ is difluoromethoxy, $R^4$ is hydrogen, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 155 covers 378 compounds of the type T-2 wherein $R^1$ is difluoromethoxy, $R^4$ is hydrogen, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 156 covers 378 compounds of the type T-2 wherein $R^1$ is difluoromethoxy, $R^4$ is hydrogen, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Table 157 covers 378 compounds of the type T-2 wherein $R^1$ is trifluoromethoxy, $R^4$ is hydrogen, $R^5$, $R^6$, $R^8$, $R^9$, $R^1$ and $R^{12}$ are hydrogen and $R^2$ and $R^3$ are as defined in Table 10

Table 158 covers 378 compounds of the type T-2 wherein $R^1$ is trifluoromethoxy, $R^4$ is hydrogen, $R^5$ is hydrogen, $R^6$ is methyl, $R^8$, $R^9$, $R^{11}$ and $R^{12}$ are hydrogen and $R^2$ and $R^3$ are as defined in Table 1.

Table 159 covers 378 compounds of the type T-2 wherein $R^1$ is trifluoromethoxy, $R^4$ is hydrogen, $R^5$ is hydrogen, $R^6$ is ethyl, $R^5$, $R^9$, $R^{11}$ and $R^{12}$ are hydrogen and $R^2$ and $R^3$ are as defined in Table 1.

Table 160 covers 378 compounds of the type T-2 wherein $R^1$ is trifluoromethoxy, $R^4$ is hydrogen, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 161 covers 378 compounds of the type T-2 wherein $R^1$ is trifluoromethoxy, $R^4$ is hydrogen, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 162 covers 378 compounds of the type T-2 wherein $R^1$ is trifluoromethoxy, $R^4$ is hydrogen, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 163 covers 378 compounds of the type T-2 wherein $R^1$ is trifluoromethoxy, $R^4$ is hydrogen, $R^5$ and $R^6$ are hydrogen, $R^8$ is methyl, $R^9$, $R^{11}$ and $R^{12}$ are hydrogen and $R^2$ and $R^3$ are as defined in Table 1.

Table 164 covers 378 compounds of the type T-2 wherein $R^1$ is trifluoromethoxy, $R^4$ is hydrogen, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 165 covers 378 compounds of the type T-2 wherein $R^1$ is trifluoromethoxy, $R^4$ is hydrogen, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 166 covers 378 compounds of the type T-2 wherein $R^1$ is trifluoromethoxy, $R^4$ is hydrogen, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 167 covers 378 compounds of the type T-2 wherein $R^1$ is trifluoromethoxy, $R^4$ is hydrogen, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 168 covers 378 compounds of the type T-2 wherein $R^1$ is trifluoromethoxy, $R^4$ is hydrogen, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Table 169 covers 378 compounds of the type T-2 wherein $R^1$ is cyclopropyl, $R^4$ is hydrogen, $R^5$, $R^6$, $R^8$, $R^9$, $R^{11}$ and $R^{12}$ are hydrogen and $R^2$ and $R^3$ are as defined in Table 1.

Table 170 covers 378 compounds of the type T-2 wherein $R^1$ is cyclopropyl, $R^4$ is hydrogen, $R^5$ is hydrogen, $R^6$ is methyl, $R^8$, $R^9$, $R^{11}$ and $R^{12}$ are hydrogen and $R^2$ and $R^3$ are as defined in Table 1.

Table 171 covers 378 compounds of the type T-2 wherein $R^1$ is cyclopropyl, $R^4$ is hydrogen, $R^5$ is hydrogen, $R^6$ is ethyl, $R^8$, $R^9$, $R^{11}$ and $R^{12}$ are hydrogen and $R^2$ and $R^3$ are as defined in Table 1.

Table 172 covers 378 compounds of the type T-2 wherein $R^1$ is cyclopropyl, $R^4$ is hydrogen, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 173 covers 378 compounds of the type T-2 wherein $R^1$ is cyclopropyl, $R^4$ is hydrogen, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 174 covers 378 compounds of the type T-2 wherein $R^1$ is cyclopropyl, $R^4$ is hydrogen, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 175 covers 378 compounds of the type T-2 wherein $R^1$ is cyclopropyl, $R^4$ is hydrogen, $R^5$ and $R^6$ are hydrogen, $R^8$ is methyl, $R^9$, $R^{11}$ and $R^{12}$ are hydrogen and $R^2$ and $R^3$ are as defined in Table 1.

Table 176 covers 378 compounds of the type T-2 wherein $R^1$ is cyclopropyl, $R^4$ is hydrogen, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 177 covers 378 compounds of the type T-2 wherein $R^1$ is cyclopropyl, $R^4$ is hydrogen, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 178 covers 378 compounds of the type T-2 wherein $R^1$ is cyclopropyl, $R^4$ is hydrogen, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 179 covers 378 compounds of the type T-2 wherein $R^1$ is cyclopropyl, $R^4$ is hydrogen, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 180 covers 378 compounds of the type T-2 wherein $R^1$ is cyclopropyl, $R^4$ is hydrogen, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

Table 181 covers 378 compounds of the type T-2 wherein $R^1$ is chlorine, $R^4$ is hydrogen, $R^5$, $R^6$, $R^8$, $R^9$, $R^{11}$ and $R^{12}$ are hydrogen and $R^2$ and $R^3$ are as defined in Table 1

Table 182 covers 378 compounds of the type T-2 wherein $R^1$ is chlorine, $R^4$ is hydrogen, $R^5$ is hydrogen, $R^6$ is methyl, $R^8$, $R^9$, $R^{11}$ and $R^{12}$ are hydrogen and $R^2$ and $R^3$ are as defined in Table 1.

Table 183 covers 378 compounds of the type T-2 wherein $R^1$ is chlorine, $R^4$ is hydrogen, $R^5$ is hydrogen, $R^6$ is ethyl, $R^8$, $R^9$, $R^{11}$ and $R^{12}$ are hydrogen and $R^2$ and $R^3$ are as defined in Table 1.

Table 184 covers 378 compounds of the type T-2 wherein $R^1$ is chlorine, $R^4$ is hydrogen, $R^5$ is hydrogen, $R^6$ is methoxymethyl, $R^8$, $R^9$, $R^{11}$ and $R^{12}$ are hydrogen and $R^2$ and $R^3$ are as defined in Table 1.

Table 185 covers 378 compounds of the type T-2 wherein $R^1$ is chlorine, $R^4$ is hydrogen, $R^5$ is hydrogen, $R^6$ is ethoxymethyl, $R^8$, $R^9$, $R^{11}$ and $R^{12}$ are hydrogen and $R^2$ and $R^3$ are as defined in Table 1.

Table 186 covers 378 compounds of the type T-2 wherein $R^1$ is chlorine, $R^4$ is hydrogen, $R^5$ is hydrogen, $R^6$ is methoxyethyl, $R^8$, $R^9$, $R^{11}$ and $R^{12}$ are hydrogen and $R^2$ and $R^3$ are as defined in Table 1.

Table 187 covers 378 compounds of the type T-2 wherein $R^1$ is chlorine, $R^4$ is hydrogen, $R^5$ and $R^6$ are hydrogen, $R^8$ is methyl, $R^9$, $R^{11}$ and $R^{12}$ are hydrogen and $R^2$ and $R^3$ are as defined in Table 1.

Table 188 covers 378 compounds of the type T-2 wherein $R^1$ is chlorine, $R^4$ is hydrogen, $R^5$ and $R^6$ are hydrogen, $R^8$ is ethyl, $R^9$, $R^{11}$ and $R^{12}$ are hydrogen and $R^2$ and $R^3$ are as defined in Table 1.

Table 189 covers 378 compounds of the type T-2 wherein $R^1$ is chlorine, $R^4$ is hydrogen, $R^5$ and $R^6$ are hydrogen, $R^8$ is methoxymethyl, $R^9$, $R^{11}$ and $R^{12}$ are hydrogen and $R^2$ and $R^3$ are as defined in Table 1.

Table 190 covers 378 compounds of the type T-2 wherein $R^1$ is chlorine, $R^4$ is hydrogen, $R^5$ and $R^6$ are hydrogen, $R^8$ is ethoxymethyl, $R^9$, $R^{11}$ and $R^{12}$ are hydrogen and $R^2$ and $R^3$ are as defined in Table 1.

Table 191 covers 378 compounds of the type T-2 wherein $R^1$ is chlorine, $R^4$ is hydrogen, $R^5$ and $R^6$ are hydrogen, $R^8$ is methoxyethyl, $R^9$, $R^{11}$ and $R^{12}$ are hydrogen and $R^2$ and $R^3$ are as defined in Table 1.

Table 192 covers 378 compounds of the type T-2 wherein $R^1$ is chlorine, $R^4$ is hydrogen, $R^5$ is hydrogen, $R^6$ is methyl, $R^8$ and $R^9$ are hydrogen, $R^{11}$ is methyl, $R^{12}$ is hydrogen and $R^2$ and $R^3$ are as defined in Table 1.

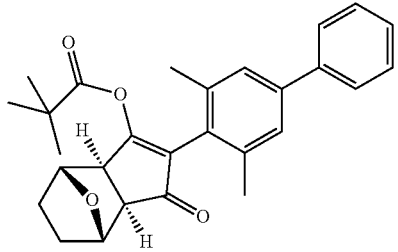 [SMILES: Cc1cc(-c2ccccc2)cc(C)c1C1=C(OC(=O)C(C)(C)C)[C@H]2[C@@H](C1=O)[C@@H]1CC[C@H]2O1]

TABLE P1

| Compound Number | Structure | $^1$H nmr (CDCl$_3$ unless stated) or other physical data |
|---|---|---|
| P1 | 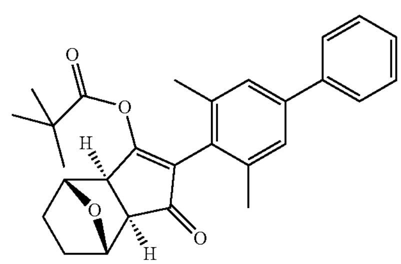 [SMILES: Cc1cc(-c2ccccc2)cc(C)c1C1=C(OC(=O)C(C)(C)C)[C@H]2[C@@H](C1=O)[C@@H]1CC[C@H]2O1] | $\delta_H$ 7.62 (2H, d), 7.46 (t, 2H), 7.37 (1H, t), 7.32 (1H, s), 7.30 (1H, s), 4.82 (1H, d), 4.64 (1H, d), 3.53 (1H, d), 2.87 (1H, d), 2.25 (3H, s), 2.19 (3H, s), 2.00-1.86 (2H, m), 1.73-1.63 (2H, m), 1.16 (9H, s). |
| P2 | 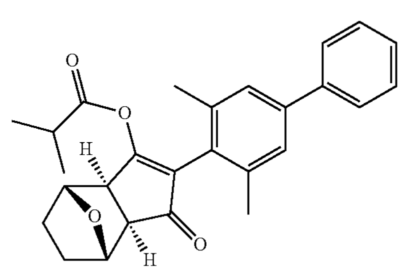 [SMILES: Cc1cc(-c2ccccc2)cc(C)c1C1=C(OC(=O)C(C)C)[C@H]2[C@@H](C1=O)[C@@H]1CC[C@H]2O1] | $\delta_H$ 7.57 (2H, d), 7.41 (2H, t), 7.32 (1H, t), 7.27 (1H, s), 7.25 (1H, a), 4.77 (1H, d), 4.60 (1H, d), 3.52 (1H, d), 2.82 (1H, d), 2.63 (1H, sept), 2.20 (3H, s), 2.14 (3H, s), 1.95-1.81 (2H, m), 1.67-1.58 (2H, m), 1.13 (3H, d), 1.06 (3H, d). |

TABLE P1-continued

| Compound Number | Structure | ¹H nmr (CDCl₃ unless stated) or other physical data |
|---|---|---|
| P3 | 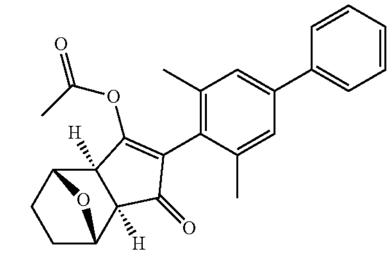 [SMILES: CC(=O)OC1=C(c2c(C)cc(-c3ccccc3)cc2C)C(=O)[C@@H]2[C@H]1[C@H]1CC[C@@H]2O1] | δ$_H$ 7.57 (2H, d), 7.42 (2H, t). 7.32 (1H, t), 7.28 (1H, s), 7.26 (1H, s), 4.76 (1H, d), 4.61 (1H, d), 3.58 (1H, d), 2.82 (1H, d), 2.20 (3H, s), 2.17 (3H, s), 2.15 (3H, s), 1.95-1.81 (2H, m), 1.67-1.58 (2H, m). |
| P4 | 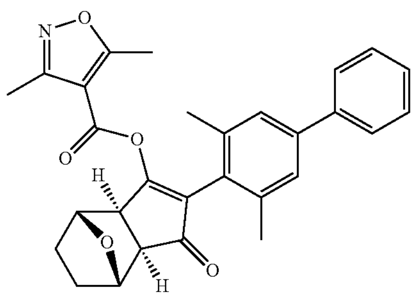 [SMILES: Cc1cc(-c2ccccc2)cc(C)c1C1=C(OC(=O)c2c(C)noc2C)[C@H]2[C@@H](C1=O)[C@@H]1CC[C@H]2O1] | δ$_H$ 7.55 (2H, d), 7.42 (2H, t), 7.33 (1H, t), 7.29 (1H, s), 7.26 (1H, s), 4.81 (1H, d), 4.67 (1H, d), 3.81 (1H, d), 2.87 (1H, d), 2.36 (3H, s), 2.22 (3H, s), 2.20 (3H, s), 2.15 (3H, s), 1.99-1.84 (2H, m), 1.77-1.62 (1H, m). |
| P5 | 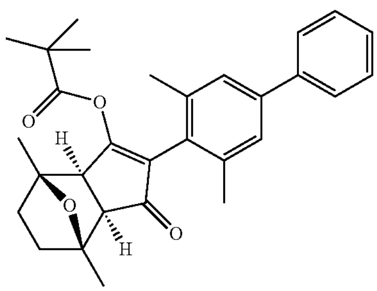 [SMILES: Cc1cc(-c2ccccc2)cc(C)c1C1=C(OC(=O)C(C)(C)C)[C@H]2[C@@H](C1=O)[C@]1(C)CC[C@@]2(C)O1] | δ$_H$ 7.57 (2H, d), 7.41 (2H, t), 7.32 (1H, t), 7.27 (11-1, s), 7.25 (1H, s), 3.48 (1H, d), 2.80 (1H, d), 2.24 (3H, s), 2.12 (3H, s), 1.84-1.67 (4H, m), 1.57 (6H, d), 1.06 (9H. s). |
| P6 | 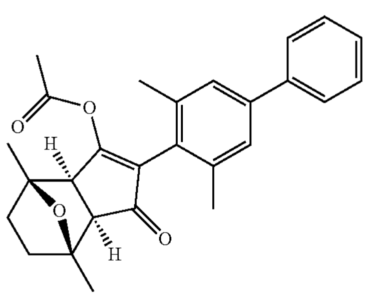 [SMILES: CC(=O)OC1=C(c2c(C)cc(-c3ccccc3)cc2C)C(=O)[C@@H]2[C@H]1[C@@]1(C)CC[C@]2(C)O1] | δ$_H$ 7.57 (2H, d), 7.41 (2H, t), 7.32 (1H, 0, 7.29 (1H, s), 7.27 (1H, s), 3.63 (1H, d), 2.79 (1H, d), 2.23 (3H, s), 2.15 (3H, s), 2.13 (3H, s), 1.85-1.69 (4H, m), 1.57 (6H, d). |
| P7 | 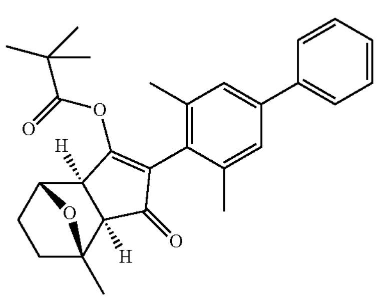 [SMILES: Cc1cc(-c2ccccc2)cc(C)c1C1=C(OC(=O)C(C)(C)C)[C@H]2[C@@H](C1=O)[C@]1(C)CC[C@H]2O1] | δ$_H$ 7.57 (2H, d), 7.41 (2H, t), 7.32 (1H, t), 7.27 (1H, s), 7.25 (1H, s), 4.49 (1H, d), 3.58 (1H, d), 2.70 (1H, d), 2.21 (3H, s), 2.14 (3H, s), 2.03-1.97 (1H, m), 1.72-1.61 (3H, m), 1.58 (3H, s), 1.11 (9H, s). |

TABLE P1-continued

| Compound Number | Structure | ¹H nmr (CDCl₃ unless stated) or other physical data |
|---|---|---|
| P8 | 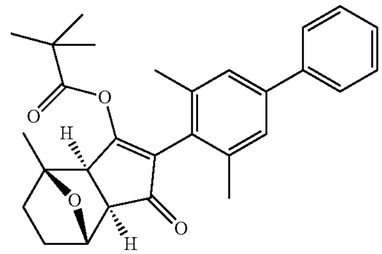 [SMILES: Cc1cc(-c2ccccc2)cc(C)c1C1=C(OC(=O)C(C)(C)C)[C@H]2[C@@H](C1=O)[C@@H]1CC[C@@]2(C)O1] | $\delta_H$ 7.57 (2H, d), 7.41 (2H, t), 7.32 (1H, t), 7.27 (1H, s), 7.25 (1H, s), 4.72 (1H, d), 3.38 (1H, d), 2.94 (1H, d), 2.24 (3H, s), 2.12 (3H, s), 1.80-1.61 (4H, m), 1.60 (3H, s), 1.07 (9H, s). |
| P9 | 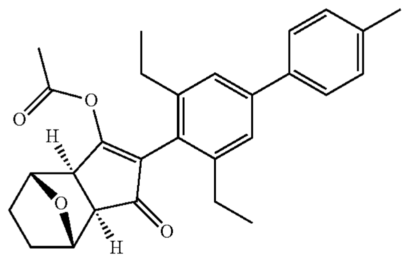 [SMILES: CCc1cc(-c2ccc(C)cc2)cc(CC)c1C1=C(OC(C)=O)[C@H]2[C@@H](C1=O)[C@@H]1CC[C@H]2O1] | $\delta_H$ 7.47 (2H, d), 7.30 (2H, dd), 7.20 (2H, d), 4.70 (1H, d), 4.60 (1H, d), 3.60 (1H, d), 2.80 (1H, d), 2.39-2.49 (4H, m), 2.37 (3H, s), 2.17 (3H, s), 1.90-1.84 (2H, m), 1.67-1.60 (2H, m), 1.15-1.08 (6H, m) |
| P10 | 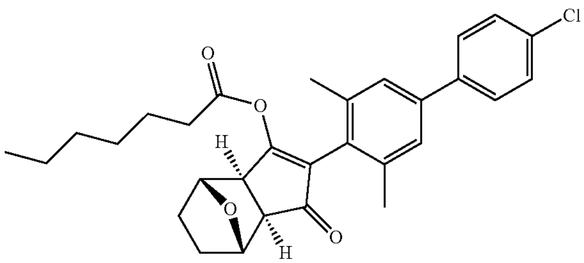 [SMILES: CCCCCCC(=O)OC1=C(c2c(C)cc(-c3ccc(Cl)cc3)cc2C)C(=O)[C@@H]2[C@H]1[C@H]1CC[C@@H]2O1] | $\delta_H$ 7.54 (2H, d), 7.42 (2H, d), 7.28 (1H, s), 7.26 (1H, s), 4.80 (1H, d), 4.65 (1H, d), 3.56 (1H. d). 2.85 (1H, d), 2.24 (3H, s), 2.19 (3H, s), 1.99-1.85 (2H, m), 1.72-1.54 (4H, m), 1.40-1.22 (5H, m), 0.94-0.84 (4H, m). |
| P11 | 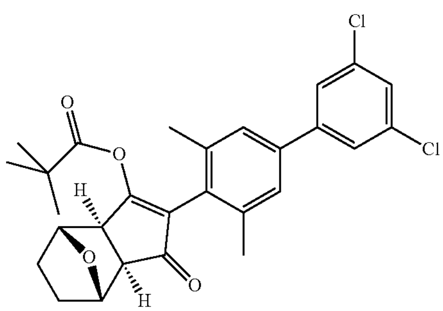 [SMILES: Cc1cc(-c2cc(Cl)cc(Cl)c2)cc(C)c1C1=C(OC(=O)C(C)(C)C)[C@H]2[C@@H](C1=O)[C@@H]1CC[C@H]2O1] | $\delta_H$ 7.50 (1H, d), 7.40 (1H, s), 7.30 (1H, d), 7.20 (2H, d), 4.80 (1H. d), 4.60 (1H, d), 3.50 (1H. d). 2.80 (1H, d), 2.20 (3H, s), 2.10 (3H, s), 1.85 (2H, m), 1.60 (2H, m), 1.10 (9H. s). |
| P12 | 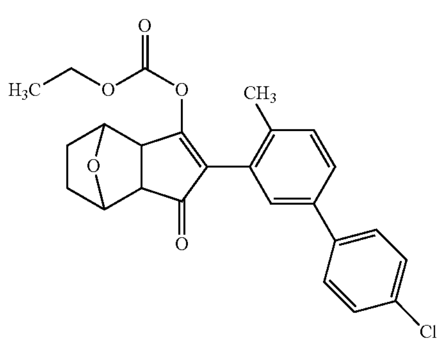 [SMILES: CCOC(=O)OC1=C(c2cc(-c3ccc(Cl)cc3)ccc2C)C(=O)C2C3CCC(O3)C12] | $\delta$ = 1.21 and 1.29 (triplets, 3H in total), 1.61 and 1.88 (each mc, each 2H), 2.11 and 2.20 (2 singlets, 3H in total), 2.78 (mc, 1H), 3.51 (mc, 1H) 4.22 (mc, 2H), 4.63 and 4.76 (each mc, each 1H), 7.10-7.48 (m, 7H) |

Preparation of P 12

300 mg from Example T1 are introduced in 10 ml of dichloromethane, 0.34 ml of triethylamine is added, and then 0.09 ml of ethyl chloroformate is added dropwise. The mixture is stirred at room temperature for 30 minutes and then concentrated, and the residue is chromatographed on silica gel using 7:3 heptane/ethyl acetate as the solvent system. This gives 272 mg of product (=75% of theory).

The active compounds of the invention, in combination with good plant tolerance and favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can be preferably employed as plant protection agents. They are active against normally sensitive and resistant species and against all or some stages of development. The abovementioned pests include:

From the phylum of Mollusca e.g. from the class of the Lamellibranchiata e.g. *Dreissena* spp.

From the class of the Gastropoda e.g. *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

From the phylum: Arthropoda e.g. from the order of Isopoda e.g. *Armadillidium vulgare, Oniscus asellus, Porcellio scaber.*

From the class of the Arachnida e.g. *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Centruroides* spp., *Chorioptes* spp., *Dermanyssus gallinae, Dermatophagoides* pteronyssius, *Dermatophagoides farinae, Dermacentor* spp., *Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vaejovis* spp., *Vasates lycopersici.*

From the order of Symphyla e.g. *Scutigerella* spp.

From the order of Chilopoda e.g. *Geophilus* spp., *Scutigera* spp.

From the order of Collembola e.g. *Onychiurus armatus.*

From the order of Diplopoda e.g. *Blaniulus guttulatus.*

From the order of Zygentoma e.g. *Lepisma saccharina, Thermobia domestica.*

From the order of Orthoptera e.g. *Acheta domesticus, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria, Supella longipalpa.*

From the order of Isoptera e.g. *Coptotermes* spp., *Cornitermes cumulans, Cryptotermes* spp., *Incisitermes* spp., *Microtermes obesi, Odontotermes* spp., *Reticulitermes* spp., From the order of Heteroptera e.g. *Anasa tristis, Antestiopsis* spp., *Boisea* spp., *Blissus* spp., *Calocoris* spp., *Campylomma livida, Cavelerius* spp., *Cimex lectularius, Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., Pseudacysta *persea, Rhodnius* spp., *Sahlbergella singularis, Scaptocoris castanea, Scotinophora* spp., *Stephanitis nashi, Tibraca* spp., *Triatoma* spp.

From the order of Anoplura (Phthiraptera) e.g. *Damalinia* spp., *Haematopinus* spp., *Linognathus* spp., *Pediculus* spp., *Ptirus pubis, Trichodectes* spp.

From the order of Homoptera e.g. *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., Lao-delphax striatellus, *Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of Coleoptera e.g. *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., Lisso-rhoptrus oryzophilus, *Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sphenophorus* spp., *Stegobium paniceum,*

*Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp.

From the order of Hymenoptera e.g. *Acromyrmex* spp., *Athalia* spp., *Atta* spp., *Diprion* spp., Hop-locampa spp., *Lasius* spp., *Monomorium pharaonis*, *Solenopsis invicta*, *Tapinoma* spp., *Vespa* spp.

From the order of Lepidoptera e.g. *Acronicta major*, *Adoxophyes* spp., *Aedia leucomelas*, *Agrotis* spp., *Alabama* spp., *Amyelois transitella*, *Anarsia* spp., *Anticarsia* spp., *Argyroploce* spp., *Barathra brassicae*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Chematobia brumata*, *Chilo* spp., *Choristoneura* spp., *Clysia ambiguella*, *Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia* spp., *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phylloenistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp., *Sparganothis* spp., *Spodoptera* spp., *Stathmopoda* spp., *Stomopteryx subsecivella*, *Synanthedon* spp., *Tecia solanivora*, *Thermesia gemmatalis*, *Tinea pellionella*, *Tineola bisselliella*, *Tortrix* spp., *Trichophaga tapetzella*, *Trichoplusia* spp., *Tuta absoluta*, *Virachola* spp.

From the order of Diptera e.g. *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Chrysops* spp., *Cochliomyia* spp., *Contarinia* spp., *Cordylobia anthropophaga*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp. *Lucilia* spp., *Lutzomia* spp., *Mansonia* spp., *Musca* spp., *Nezara* spp., *Oestrus* spp., *Oscinella frit*, *Pegomyia* spp., *Phlebotomus* spp., *Phorbia* spp., *Phormia* spp., *Prodiplosis* spp., *Psila rosae*, *Rhagoletis* spp., *Sarcophaga* spp., *Simulium* spp, *Stomoxys* spp., *Tabanus* spp., *Tannia* spp., *Tetanops* spp., *Tipula* spp.

From the order of Thysanoptera e.g. *Anaphothrips obscurus*, *Baliothrips biformis*, *Drepanothris reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamoni*, *Thrips* spp.

From the order of Siphonaptera e.g. *Ceratophyllus* spp., *Ctenocephalides* spp., *Tunga penetrans*, *Xenopsylla cheopis*.

From the phylums Plathelminthes and Nematoda as animal parasites e.g. from the class of the Helminths e.g. *Ancylostoma duodenale*, *Ancylostoma ceylanicum*, *Acylostoma braziliensis*, *Ancylostoma* spp., *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., Loa Loa, *Nematodirus* spp., *Oesophagostomum* spp., *Opisthorchis* spp., *Onchocerca volvulus*, *Ostertagia* spp., *Paragonimus* spp., *Schistosomen* spp, *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

From the phylum Nematoda as plant pests e e.g. *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis*, *Trichodorus* spp., *Tylenchulus semipenetrans*, *Xiphinema* spp.

From the subphylum of protozoa e.g. Eimeria.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example by immersion, spraying, evaporation, fogging, scattering, painting on, injection and, in the case of propagation material, in particular in the case of seeds, also by applying one or more coats.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or —POP-ethers, acid and/or POP—POE esters, alkyl aryl and/or POP—POE ethers, fat- and/or POP—POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly) amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compound according to the invention can be used in its commercially available formulations and in the use forms, prepared from these formulations, as a mixture with other active compounds, such as insecticides, attractants, sterilizing agents, bactericides, acaricides, nematicides, fungicides, growth-regulating substances, herbicides, safeners, fertilizers or semiochemicals.

A mixture with other known active compounds, such as herbicides, fertilizers, growth regulators, safeners, semiochemicals, or else with agents for improving the plant properties, is also possible.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acari (Acariha) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, portions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus, Chlorophorus pilosis, Anobium punctatum, Xestobium rufovillosum, Ptilinus pectinicornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenopterons, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, such as hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Avicullariidae, Araneidae.*

From the order of the Opiliones, for example, *Pseudoscorpiones chelifer, Pseudoscorpiones cheiridium,* Opiliones *phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the *Dermaptera*, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The compounds according to the invention exhibit a strong microbicidal action and can be used for combating undesirable microorganisms, such as fungi and bacteria, in plant protection and in material protection.

Fungicides can be used in plant protection for combating Plasmodiophoromycetes, Oomycetes, Chytridiomycetes, Zygomycetes, Ascomycetes, Basidiomycetes and Deuteromycetes.

Bactericides can be used in plant protection for combating Pseudomonadaceae, Rhizobiaceae, Enterobacteriaceae, Corynebacteriaceae and Streptomycetaceae.

Mention may be made, by way of example but without limitation, of some pathogens of fungal and bacterial diseases which come under the generic terms listed above:

diseases caused by pathogens of powdery mildew, such as, for example,

*Blumeria* species, such as, for example, *Blumeria graminis*;
*Podosphaera* species, such as, for example, *Podosphaera leucotricha*;
*Sphaerotheca* species, such as, for example, *Sphaerotheca fuliginea*;
*Uncinula* species, such as, for example, *Uncinula necator*;

diseases caused by rust pathogens, such as, e.g.,

*Gymnosporangium* species, such as, for example, *Gymnosporangium sabinae*;
*Hemileia* species, such as, for example, *Hemileia vastatrix*;
*Phakopsora* species, such as, for example, *Phakopsora pachyrhizi* and *Phakopsora meibomiae*;
*Puccinia* species, such as, for example, *Puccinia recondita*;
*Uromyces* species, such as, for example, *Uromyces appendiculatus*;

diseases caused by pathogens of the Oomycetes group, such as, e.g.,

*Bremia* species, such as, for example, *Bremia lactucae*;
*Peronospora* species, such as, for example, *Peronospora pisi* or *P. brassicae*;
*Phytophthora* species, such as, for example, *Phytophthora infestans*;
*Plasmopara* species, such as, for example, *Plasmopara viticola*;
*Pseudoperonospora* species, such as, for example, *Pseudoperonospora humuli* or *Pseudoperonospora cubensis*;
*Pythium* species, such as, for example, *Pythium ultimum*;

leaf spot diseases and leaf wilts caused by, e.g.,

*Alternaria* species, such as, for example, *Alternaria solani*;
*Cercospora* species, such as, for example, *Cercospora beticola*;
*Cladosporium* species, such as, for example, *Cladosporium cucumerinum*;
*Cochliobolus* species, such as, for example, *Cochliobolus sativus* (conidial form: *Drechslera*, syn: *Helminthosporium*);
*Colletotrichum* species, such as, for example, *Colletotrichum lindemuthanium*;
*Cycloconium* species, such as, for example, *Cycloconium oleaginum*;
*Diaporthe* species, such as, for example, *Diaporthe citri*;
*Elsinoe* species, such as, for example, *Elsinoe fawcettii*;
*Gloeosporium* species, such as, for example, *Gloeosporium laeticolor*;
*Glomerella* species, such as, for example, *Glomerella cingulata*;
*Guignardia* species, such as, for example, *Guignardia bidwelli*;
*Leptosphaeria* species, such as, for example, *Leptosphaeria maculans*;
*Magnaporthe* species, such as, for example, *Magnaporthe grisea*;
*Mycosphaerella* species, such as, for example, *Mycosphaerella graminicola* and *Mycosphaerella fijiensis*;
*Phaeosphaeria* species, such as, for example, *Phaeosphaeria nodorum*;

*Pyrenophora* species, such as, for example, *Pyrenophora teres*;
*Ramularia* species, such as, for example, *Ramularia collocygni*;
*Rhynchosporium* species, such as, for example, *Rhynchosporium secalis*;
*Septoria* species, such as, for example, *Septoria apii*;
*Typhula* species, such as, for example, *Typhula incarnata*;
*Venturia* species, such as, for example, *Venturia inaequalis*;
root and stalk diseases caused by, e.g.,
*Corticium* species, such as, for example, *Corticium graminearum*;
*Fusarium* species, such as, for example, *Fusarium oxysporum*;
*Gaeumannomyces* species, such as, for example, *Gaeumannomyces graminis*;
*Rhizoctonia* species, such as, for example, *Rhizoctonia solani*;
*Tapesia* species, such as, for example, *Tapesia acuformis*;
*Thielaviopsis* species, such as, for example, *Thielaviopsis basicola*;
ear and panicle diseases (including maize cobs) caused by, e.g.,
*Alternaria* species, such as, for example, *Alternaria* spp.;
*Aspergillus* species, such as, for example, *Aspergillus flavus*;
*Cladosporium* species, such as, for example, *Cladosporium cladosporioides*;
*Claviceps* species, such as, for example, *Claviceps purpurea*;
*Fusarium* species, such as, for example, *Fusarium culmorum*;
*Gibberella* species, such as, for example, *Gibberella zeae*;
*Monographella* species, such as, for example, *Monographella nivalis*;
diseases caused by smuts, such as, e.g.,
*Sphacelotheca* species, such as, for example, *Sphacelotheca reiliana*;
*Tilletia* species, such as, for example, *Tilletia caries*;
*Urocystis* species, such as, for example, *Urocystis occulta*;
*Ustilago* species, such as, for example, *Ustilago nuda*;
fruit rot caused by, e.g.,
*Aspergillus* species, such as, for example, *Aspergillus flavus*;
*Botrytis* species, such as, for example, *Botrytis cinerea*;
*Penicillium* species, such as, for example, *Penicillium expansum* and *Penicillium purpurogenum*;
*Sclerotinia* species, such as, for example, *Sclerotinia sclerotiorum*;
*Verticilium* species, such as, for example, *Verticilium alboatrum*;
seed- and soil-borne rots and wilts, and seedling diseases, caused by, e.g.,
*Alternaria* species, such as, for example, *Alternaria brassicicola*;
*Aphanomyces* species, such as, for example, *Aphanomyces euteiches*;
*Ascochyta* species, such as, for example, *Ascochyta lentis*;
*Aspergillus* species, such as, for example, *Aspergillus flavus*;
*Cladosporium* species, such as, for example, *Cladosporium herbarum*;
*Cochliobolus* species, such as, for example, *Cochliobolus sativus* (conidial form: *Drechslera, Bipolaris* syn: *Helminthosporium*);
*Colletotrichum* species, such as, for example, *Colletotrichum coccodes*;
*Fusarium* species, such as, for example, *Fusarium culmorum*;
*Gibberella* species, such as, for example, *Gibberella zeae*;
*Macrophomina* species, such as, for example, *Macrophomina phaseolina*;
*Monographella* species, such as, for example, *Monographella nivalis*;
*Penicillium* species, such as, for example, *Penicillium expansum*;
*Phoma* species, such as, for example, *Phoma lingam*;
*Phomopsis* species, such as, for example, *Phomopsis sojae*;
*Phytophthora* species, such as, for example, *Phytophthora cactorum*;
*Pyrenophora* species, such as, for example, *Pyrenophora graminea*;
*Pyricularia* species, such as, for example, *Pyricularia oryzae*;
*Pythium* species, such as, for example, *Pythium ultimum*;
*Rhizoctonia* species, such as, for example, *Rhizoctonia solani*;
*Rhizopus* species, such as, for example, *Rhizopus oryzae*;
*Sclerotium* species, such as, for example, *Sclerotium rolfsii*;
*Septoria* species, such as, for example, *Septoria nodorum*;
*Typhula* species, such as, for example, *Typhula incarnata*;
*Verticillium* species, such as, for example, *Verticillium dahliae*;
cankers, galls and witches' broom disease caused by, e.g.,
*Nectria* species, such as, for example, *Nectria galligena*;
wilts caused by, e.g.,
*Monilinia* species, such as, for example, *Monilinia laxa*;
deformations of leaves, flowers and fruits caused by, e.g.,
*Taphrina* species, such as, for example, *Taphrina deformans*;
degenerative diseases of woody plants caused by, e.g.,
*Esca* species, such as, for example, *Phaeomoniella chlamydospora*, *Phaeoacremonium aleophilum* and *Fomitiporia mediterranea*;
flower and seed diseases caused by, e.g.,
*Botrytis* species, such as, for example, *Botrytis cinerea*;
diseases of plant tubers caused by, e.g.,
*Rhizoctonia* species, such as, for example, *Rhizoctonia solani*;
*Helminthosporium* species, such as, for example, *Helminthosporiu solani*;
diseases caused by bacterial pathogens, such as, e.g.,
*Xanthomonas* species, such as, for example, *Xanthomonas campestris* pv. *oryzae*;
*Pseudomonas* species, such as, for example, *Pseudomonas syringae* pv. *lachrymans*;
*Erwinia* species, such as, for example, *Erwinia amylovora*.

Preferably, the following diseases of soybeans can be combated:

fungal diseases on leaves, stalks, pods and seeds caused by, e.g.,
alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (Dactuliophora glycines), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (Pyrenochaeta glycines), *rhizoctonia* aerial, foliage, and web blight (*Rhizoctonia solani*), rust (*Phakopsora pachyrhizi*), scab (Sphaceloma glycines), *stemphylium* leaf blight (*Stemphylium botryosum*), target spot (*Corynespora cassiicola*)

fungal diseases on roots and the stem base caused by, e.g., black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The active substances according to the invention also exhibit a strong strengthening activity in plants. They are accordingly suitable for mobilizing intrinsic defences of plants against attack by undesirable microorganisms.

In the present context, plant-strengthening (resistance-inducing) substances are to be understood as meaning those materials which are capable of stimulating the defence system of plants such that the treated plants, on subsequent inoculation with undesirable microorganisms, exhibit extensive resistance to these microorganisms.

In the present case, undesirable microorganisms are to be understood as meaning phytopathogenic fungi, bacteria and viruses. The substances according to the invention can thus be used to protect plants from attack by the harmful pathogens mentioned for a certain period of time after the treatment. The period of time for which protection is brought about generally ranges from 1 to 10 days, preferably 1 to 7 days, after the treatment of the plants with the active substances.

The fact that the active substances are well tolerated by plants in the concentrations necessary for combating plant diseases makes possible treatment of aboveground plant parts, of plant propagation material and seed, and of the soil.

In this connection, the active substances according to the invention can be used particularly successfully in combating cereal diseases, such as, e.g., *Puccinia* species, and diseases in viticulture and in the cultivation of fruit and vegetables, such as, e.g., *Botrytis, Venturia* or *Alternaria* species.

The active substances according to the invention are also suitable for increasing the crop yield. In addition, they are of lower toxicity and are well tolerated by plants.

The active substances according to the invention can also optionally be used, in specific concentrations and application amounts, as herbicides, for affecting plant growth and for combating animal pests. They can optionally also be used as intermediates and precursors for the synthesis of additional active substances.

All plants and plant parts can be treated according to the invention. In this connection, plants are to be understood as meaning all plants and plant populations, such as desirable and undesirable wild plants or cultivated plants (including naturally occurring cultivated plants). Cultivated plants can be plants which can be obtained by conventional breeding and optimization methods or by biotechnological and genetic engineering methods or combinations of these methods, including transgenic plants and including plant varieties which may or may not be protected by laws on variety certification. Plant parts should be understood as meaning all aboveground and subsoil parts and organs of plants, such as shoot, leaf, flower and root, examples which are listed being leaves, needles, stalks, stems, flowers, fruiting bodies, fruits and seeds, and also roots, tubers and rhizomes. Plant parts also include harvested crops, and also vegetative and generative propagation material, for example cuttings, tubers, rhizomes, layers and seeds.

The treatment according to the invention of the plants and plant parts with the active substances is carried out directly or by acting on the environment, habitat or storage area thereof using conventional treatment methods, e.g. by dipping, spraying, evaporating, atomizing, scattering, spreading and, with propagation material, in particular with seeds, furthermore by coating with one or more layers.

In addition, it is possible, by the treatment according to the invention, to reduce the mycotoxin content in harvested crops and the foodstuffs and feedstuffs prepared therefrom. In this connection, mention may in particular but not exclusively be made of the following mycotoxins: deoxynivalenol (DON), nivalenol, 15-Ac-DON, 3-Ac-DON, T2 and HT2 toxin, fumonisins, zearalenone, moniliformin, fusarin, diacetoxyscirpenol (DAS), beauvericin, enniatin, fusaroproliferin, fusarenol, ochratoxins, patulin, ergot alkaloids and aflatoxins, which can be caused, for example, by the following fungi: *Fusarium* spec., such as *Fusarium acuminatum, F. avenaceum, F. crookwellense, F. culmorum, F. graminearum (Gibberella zeae), F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, and others, and also by *Aspergillus* spec., *Penicillium* spec., *Claviceps purpurea, Stachybotrys* spec., and others.

In material protection, the substances according to the invention can be used for the protection of industrial materials from attack and destruction by undesirable microorganisms.

Industrial materials are to be understood in the present context as meaning nonliving materials which have been prepared for use in industry. For example, industrial materials which are to be protected by active substances according to the invention from microbial change or destruction can be adhesives, sizes, paper and board, textiles, leather, wood, paints and plastic articles, cooling lubricants and other materials which can be attacked or destroyed by microorganisms. In the context of the materials to be protected, mention may also be made of parts of production plants, for example cooling water circuits, which can be detrimentally affected by proliferation of microorganisms. In the context of the present invention, mention may preferably be made, as industrial materials, of adhesives, sizes, papers and boards, leather, wood, paints, cooling lubricants and heat-transfer liquids, particularly preferably of wood.

Examples which may be mentioned of microorganisms which can decompose or modify industrial materials are bacteria, fungi, yeasts, algae and slime organisms. The active substances according to the invention are preferably active against fungi, in particular moulds, wood-discolouring and wood-destroying fungi (Basidiomycetes), and against slime organisms and algae.

Mention may be made, by way of example, of microorganisms of the following genera:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,

*Escherichia*, such as *Escherichia coli*,
*Pseudomonas*, such as *Pseudomonas aeruginosa*,
*Staphylococcus*, such as *Staphylococcus aureus*.

The present invention relates to a composition for combating undesirable microorganisms, comprising at least one of the compounds according to the invention.

The compounds according to the invention can for this, depending on their respective physical and/or chemical properties, be converted into the standard formulations, such as solutions, emulsions, suspensions, powders, foams, pastes, granules, aerosols, very fine encapsulations in polymeric substances and in coating materials for seed, and also ULV cold- and hot-fogging formulations.

These formulations are prepared in a known way, e.g. by mixing the active substances with extenders, that is liquid solvents, liquefied gases under pressure and/or solid carriers, optionally with the use of surface-active agents, that is emulsifiers and/or dispersants and/or foaming agents. In the case of the use of water as extender, use may also be made, e.g., of organic solvents as cosolvents. Possible liquid solvents are essentially: aromatic hydrocarbons, such as xylene, toluene or alkylnaphthalenes, chlorinated aromatic hydrocarbons or chlorinated aliphatic hydrocarbons, such as chlorobenzenes, chloroethylenes or methylene chloride, aliphatic hydrocarbons, such as cyclohexane or paraffinins, e.g. petroleum fractions, alcohols, such as butanol or glycol, and the ethers and esters thereof, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are to be understood as meaning those liquids which are in the gas form at standard temperature and at standard pressure, e.g. aerosol propellants, such as halogenated hydrocarbons and also butane, propane, nitrogen and carbon dioxide. Possible solid carriers are, e.g., ground natural minerals, such as kaolins, argillaceous earths, talc, chalk, quartz, attapulgite, montmorillonite or diatomaceous earth, and ground synthetic minerals, such as highly dispersed silica, aluminium oxide and silicates. Possible solid carriers for granules are, e.g., broken and fractionated natural rocks, such as calcite, pumice, marble, sepiolite or dolomite, and also synthetic granules formed from inorganic and organic dusts, and also granules formed from organic material, such as sawdust, coconut shells, maize cobs and tobacco stalks. Possible emulsifiers and/or foaming agents are, e.g., nonionic and anionic emulsifiers, such as polyoxyethylene fatty acid esters, polyoxyethylene fatty alcohol ethers, e.g. alkylaryl polyglycol ethers, alkylsulphonates, alkyl sulphates, arylsulphonates, and also protein hydrolysates. Possible dispersants are, e.g., lignosulphite, waste liquors and methylcellulose.

Use may be made, in the formulations, of stickers, such as carboxymethylcellulose, natural and synthetic polymers in the powder, granule or latex form, such as gum arabic, polyvinyl alcohol, polyvinyl acetate, and also natural phospholipids, such as cephalins and lecithins, and synthetic phospholipids. Other possible additives are mineral and vegetable oils.

Use may also be made of colorants, such as inorganic pigments, e.g. iron oxide, titanium oxide, Prussian blue, and organic colorants, such as alizarin dyes, azo dyes and metal phthalocyanine dyes, and trace elements, such as salts of iron, manganese, boron, copper, cobalt, molybdenum and zinc.

The formulations generally comprise between 0.1 and 95% by weight of active substance, preferably between 0.5 and 90%.

The formulations described above can be used in a method according to the invention for combating undesirable microorganisms, in which the compounds according to the invention are applied to the microorganisms and/or to the habitat thereof.

The combating of phytopathogenic fungi by the treatment of the seed of plants has been known for a long time and is the subject-matter of continuous improvements. Nevertheless, a series of problems arises in the treatment of seed, which problems may not always be satisfactorily solved. Thus, it is desirable to develop methods for protecting the seed and the germinating plant which render superfluous or at least markedly reduce the additional application of plant protection compositions after sowing or after emergence of the plants. It is furthermore desirable to optimize the amount of the active substance used, so that the seed and the germinating plant are given the best possible protection against attack by phytopathogenic fungi but without the plant itself being damaged by the active substance used. In particular, methods for the treatment of seed should also include the intrinsic fungicidal properties of transgenic plants in order to achieve optimum protection of the seed and the germinating plant with a minimum expenditure of plant protection compositions.

The present invention therefore also relates in particular to a method for the protection of seed and germinating plants from attack by phytopathogenic fungi, by treating the seed with a composition according to the invention.

The invention likewise relates to the use of the compositions according to the invention for the treatment of seed to protect the seed and the germinating plant from phytopathogenic fungi.

Furthermore, the invention relates to seed which has been treated with a composition according to the invention in order to protect from phytopathogenic fungi.

One of the advantages of the present invention is that, because of the particular systemic properties of the compositions according to the invention, the treatment of the seed with these compositions not only protects the seed itself from phytopathogenic fungi but also protects the plants resulting therefrom after emergence from phytopathogenic fungi. In this way, the immediate treatment of the crop at the time of sowing or shortly thereafter can be dispensed with.

It is likewise to be regarded as advantageous that the mixtures according to the invention can in particular also be used with transgenic seed.

The compositions according to the invention are suitable for the protection of seed of any plant variety used in agriculture, in the greenhouse, in forests or in horticulture. The seed concerned in this connection is in particular seed of cereals (such as wheat, barley, rye, millet and oats), maize, cotton, soya, rice, potatoes, sunflowers, beans, coffee, beet (e.g., sugarbeet and forage beet), peanuts, vegetables (such as tomatoes, cucumbers, onions and lettuce), lawns and ornamental plants. The treatment of the seed of cereals (such as wheat, barley, rye and oats), maize and rice is of particular importance.

In the context of the present invention, the composition according to the invention is applied to the seed alone or in a suitable formulation. Preferably, the seed is treated in a condition sufficiently stable for no damage to occur during the treatment. In general, the treatment of the seed can be carried out at any point in time between harvesting and sowing. Use is usually made of seed which has been separated from the plant and freed from pods, shells, stalks, skins, hairs or fruit flesh. Thus, it is possible, for example, to use seed which has been harvested, cleaned and dried up to a moisture content of less than 15% by weight. Alternatively, it is also possible to use seed which, after drying, has been treated, e.g. with water, and then dried again.

In general, care must be taken, in the treatment of the seed, that the amount of the composition according to the invention and/or of additional additives applied to the seed is chosen so that the germination of the seed is not impaired or that the plant resulting therefrom is not damaged. This is to be taken into consideration in particular with active substances which may show phytotoxic effects at certain application rates.

The compositions according to the invention can be applied immediately, thus without comprising additional components and without having been diluted. It is generally preferable to apply the compositions to the seed in the form of a suitable formulation. Suitable formulations and methods for seed treatment are known to a person skilled in the art and are described, e.g., in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active substance combinations which can be used according to the invention can be converted into the usual seed dressing formulations, such as solutions, emulsions, suspensions, powders, foams, slurries or other coating materials for seed, and also ULV formulations.

These formulations are prepared in a known way by mixing the active substances or active substance combinations with conventional additives, such as, for example, conventional extenders and also solvents or diluents, colorants, wetting agents, dispersants, emulsifiers, antifoaming agents, preservatives, secondary thickeners, adhesives, gibberellins and also water.

Suitable colorants which may be present in the seed dressing formulations which can be used according to the invention comprise all colorants conventional for such purposes. In this connection, use may be made both of pigments, which are sparingly soluble in water, and dyes, which are soluble in water. Mention may be made, as examples, of the colorants known under the descriptions Rhodamine B, C.I. Pigment Red 112 and C.I. Solvent Red 1.

Possible wetting agents which can be present in the seed dressing formulations which can be used according to the invention comprise all substances which promote wetting and are conventional in the formulation of agrochemical active substances. Use may preferably be made of alkylnaphthalenesulphonates, such as diisopropyl- or diisobutylnaphthalenesulphonates.

Suitable dispersants and/or emulsifiers which may be present in the seed dressing formulations which can be used according to the invention comprise all nonionic, anionic and cationic dispersants conventional in the formulation of agrochemical active substances. Use may preferably be made of nonionic or anionic dispersants or mixtures of nonionic or anionic dispersants. Mention may in particular be made, as suitable nonionic dispersants, of ethylene oxide/propylene oxide block polymers, alkylphenol polyglycol ethers and also tristyrylphenol polyglycol ethers, and the phosphated or sulphated derivatives thereof. Suitable anionic dispersants are in particular lignosulphonates, polyacrylic acid salts and arylsulphonate/formaldehyde condensates.

Antifoaming agents which may be present in the seed dressing formulations which can be used according to the invention comprise all foam-inhibiting substances conventional in the formulation of agrochemical active substances. Use may preferably be made of silicone defoaming agents and magnesium stearate.

Preservatives which may be present in the seed dressing formulations which can be used according to the invention comprise all substances which can be used in agrochemical compositions for such purposes. Mention may be made, by way of example, of dichlorophen and benzyl alcohol hemiformal.

Possible secondary thickeners which may be present in the seed dressing formulations which can be used according to the invention comprise all substances which can be used in agrochemical compositions for such purposes. Preferably suitable are cellulose derivatives, acrylic acid derivatives, xanthan, modified clays and highly dispersed silica.

Possible adhesives which may be present in the seed dressing formulations which can be used according to the invention comprise all conventional binders which can be used in seed dressings. Mention may preferably be made of polyvinylpyrrolidone, polyvinyl acetate, polyvinyl alcohol and tylose.

Possible gibberellins which may be present in the seed dressing formulations which can be used according to the invention preferably comprise gibberellins A1, A3 (=gibberellic acid), A4 and A7; use is particularly preferably made of gibberellic acid. Gibberellins are known (cf. R. Wegler, "Chemie der Pflanzenschutz-und Schädlingsbekämpfungsmittel" [Chemistry of Plant Protection and Pest Control Agents], Vol. 2, Springer Verlag, 1970, pp. 401-412).

The seed dressing formulations which can be used according to the invention can be used, either directly or after prior diluting with water, for the treatment of seed of the most varied species. Thus, the concentrates or the compositions which can be obtained therefrom by diluting with water can be used for the dressing of the seed of cereals, such as wheat, barley, rye, oats and triticale, and also the seed of maize, rice, rape, peas, beans, cotton, sunflowers and beet, or also of vegetable seed of the most varied natures. The seed dressing formulations which can be used according to the invention or the diluted compositions thereof can also be used for the dressing of seed of transgenic plants. In this connection, additional synergistic effects may also occur in interaction with the substances formed by expression.

All mixing devices which can be conventionally used for dressing are suitable for the treatment of seed with the seed dressing formulations which can be used according to the invention or the compositions prepared therefrom by addition of water. Specifically, the dressing procedure is such that the seed is introduced into a mixer, the amount of seed dressing formulation desired each time is added, either as such or after prior dilution with water, and mixing is carried out until the formulation is uniformly distributed over the seed. If appropriate, a drying operation follows.

The application rate of the seed dressing formulations which can be used according to the invention can be varied within a relatively wide range. It depends on the respective content of the active substances in the formulations and on the seed. The application rates of active substance combination are generally between 0.001 and 50 g per kilogram of seed, preferably between 0.01 and 15 g per kilogram of seed.

The compounds according to the invention can be used, as such or in their formulations, also in a mixture with known fungicides, bactericides, acaricides, nematicides or insecticides, in order thus, e.g., to broaden the spectrum of activity or to prevent the development of resistance.

A mixture with other known active substances, such as herbicides, or with fertilizers and growth regulators, safeners or semiochemicals is also possible.

In addition, the compounds of the formula (I) according to the invention also exhibit very good antimycotic activities. They have a very broad spectrum of antimycotic activity, in particular against dermatophytes and budding fungi, moulds and diphasic fungi (e.g. against *Candida* species, such as

*Candida albicans, Candida glabrata*), and also *Epidermophyton floccosum, Aspergillus* species, such as *Aspergillus niger* and *Aspergillus fumigatus, Trichophyton* species, such as *Trichophyton mentagrophytes, Microsporon* species, such as *Microsporon canis* and audouinii. The enumeration of these fungi does not represent in any way a limitation on the mycotic spectrum which can be included but has only an illustrative nature.

The compounds according to the invention can accordingly be used both in medicinal and in nonmedicinal applications.

The active substances can be applied as such, in the form of their formulations or in the form of the application forms prepared therefrom, such as ready-to-use solutions, suspensions, wettable powders, pastes, soluble powders, dusts and granules. Application takes place in standard fashion, e.g. by pouring, spraying, atomizing, scattering, dusting, foaming, spreading, and the like. It is furthermore possible to apply the active substances by the ultra-low-volume method or to inject the active substance composition or the active substance itself into the soil.

The seed of the plant can also be treated.

When the compound according to the invention are used as fungicides, the application rates can be varied within a relatively wide range depending on the type of application. In the treatment of plant parts, the application rates of active substance are generally between 0.1 and 10 000 g/ha, preferably between 10 and 1000 g/ha. In seed treatment, the application rates of active substance are generally between 0.001 and 50 g per kilogram of seed, preferably between 0.01 and 10 g per kilogram of seed. In soil treatment, the application rates of active substance are generally between 0.1 and 10 000 g/ha, preferably between 1 and 5000 g/ha.

As already mentioned above, all plants and the parts thereof can be treated according to the invention. In a preferred embodiment, plant species and plant varieties occurring in the wild or obtained by conventional biological breeding methods, such as crossing or protoplast fusion, and the parts thereof are treated. In an additional preferred embodiment, transgenic plants and plant varieties obtained by genetic engineering methods, optionally in combination with conventional methods, (genetically modified organisms) and the parts thereof are treated. The term "parts" or "parts of plants" or "plant parts" was explained above.

The method of treatment according to the invention can be used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new. or improved agronomic or other properties by expressing a protein or polypeptide of interest or by downregulating or silencing other gene(s) which are present in the plant (using, for example, antisense technology, cosuppression technology or RNA interference—RNAi technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active substances and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active substance combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active substances.

Plants and plant cultivars which are preferably treated according to the invention include all plants which have genetic material which imparts particularly advantageous, useful traits to these plants (whether obtained by breeding and/or biotechnological means).

Plants and plant cultivars which are also preferably treated according to the invention are resistant against one or more biotic stresses, i.e. the said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention are those plants characterized by enhanced yield characteristics. Increased yield in the said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pot dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis or hybrid vigour which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in maize) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants that contain the genetic determinants responsible for male sterility is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in Brassica species (WO 1992/005251, WO 1995/009910, WO 1998/27806, WO 2005/002324, WO 2006/021972 and U.S. Pat. No. 6,229,072). However, genetic determinants for male sterility can also be located in the nuclear genome. Male sterile plants can also be obtained by plant biotechnology methods, such as genetic engineering. A particularly useful means of obtaining male-sterile plants is described in WO 89/10396 in which, for example, a ribonuclease, such as barnase, is selectively expressed in the tapetum cells in the stamens. Fertility can then be restored by expression in the tapetum cells of a ribonuclease inhibitor, such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a petunia EPSPS (Shah et al., Science (1986), 233, 478-481), a tomato EPSPS (Gasser et al., J. Biol. Chem. (1988), 263, 4280-4289) or an *eleusine* EPSPS (WO 2001/66704). It can also be a mutated EPSPS as described in for example EP-A 0837944, WO 2000/066746, WO 2000/066747 or WO 2002/026995. Glyphosate-tolerant plants can also be obtained by expressing a gene that encodes a glyphosate oxidoreductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described in for example WO 2002/036782, WO 2003/092360, WO 2005/012515 and WO 2007/024782. Glyphosate-tolerant plants can also be obtained by selecting plants containing naturally-occurring mutations of the abovementioned genes, as described in for example WO 2001/024615 or WO 2003/013226.

Other herbicide-resistant plants are for example plants that are made tolerant to herbicides inhibiting the enzyme glutamine synthase, such as bialaphos, phosphinotricin or glufosinate. Such plants can be obtained by expressing an enzyme detoxifying the herbicide or a mutant of the glutamine synthase enzyme that is resistant to inhibition. One such efficient detoxifying enzyme is an enzyme encoding a phosphinotricin acetyltransferase (such as the bar or pat protein from *Streptomyces* species). Plants expressing an exogenous phosphinotricin acetyltransferase are for example described in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme as described in WO 1996/038567, WO 1999/024585 and WO 1999/024586. Tolerance to HPPD inhibitors can also be obtained by transforming plants with genes encoding certain enzymes enabling the formation of homogentisate despite the inhibition of the native HPPD enzyme by the HPPD inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Further herbicide-resistant plants are plants that are made tolerant to acetolactate synthase (ALS) inhibitors. Known ALS inhibitors include, for example, sulphonylurea, imidazolinone, triazolopyrimidines, pyrimidinyloxy(thio)benzoates and/or sulphonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also in U.S. Pat. No. 5,605,011, U.S. Pat. No. 5,378,824, U.S. Pat. No. 5,141,870 and U.S. Pat. No. 5,013,659. The production of sulphonylurea-tolerant plants and imidazolinone-tolerant plants is described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and international publication WO 1996/033270. Other imidazolinone-tolerant plants are also described in, for example, WO 2004/040012, WO 2004/106529, WO 2005/020673, WO 2005/093093, WO 2006/007373, WO 2006/015376, WO 2006/024351 and WO 2006/060634. Further sulphonylurea- and imidazolinone-tolerant plants are also described in, for example, WO 2007/024782.

Other plants tolerant to imidazolinone and/or sulphonylurea can be obtained by induced mutagenesis, selection in cell cultures in the presence of herbicide or mutation breeding as described for example for soybeans in U.S. Pat. No. 5,084,082, for rice in WO 1997/41218, for sugarbeet in U.S. Pat. No. 5,773,702 and WO 1999/057965, for lettuce in U.S. Pat. No. 5,198,599, or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g. proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins (Moellenbeck et al., Nat. Biotechnol. (2001), 19, 668-72; Schnepf et al., Applied Environm. Microb. (2006), 71, 1765-1774); or 3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by maize event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in maize events MON863 or MON88017, or the Cry3A protein in maize event MIR 604;

5) an insecticidal secreted protein from *Bacillus thuringiensis* or *Bacillus cereus*, or an insecticidal portion thereof, such as the vegetative insecticidal (VIP) proteins listed at http://www.lifesci.sussex.ac.uk/Home/Neil_Crickmore/Bt/vip.html, e.g., proteins from VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795);

7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT 102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of the poly(ADP-ribose)polymerase (PARP) gene in the plant cells or plants as described in WO 2000/004173 or EP 04077984.5 or EP 06009836.5;

b. plants which contain a stress tolerance enhancing transgene capable of reducing the expression and/or activity of the PARG encoding genes of the plants or plant cells, as described e.g. in WO 2004/090140;

c. plants which contain a stress tolerance enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase, as described, e.g., in EP 04077624.7 or WO 2006/133827 or PCT/EP07/002,433.

Plants or plant cultivars (obtained by plant biotechnology methods such as genetic engineering) which may also be treated according to the invention show altered quantity, quality and/or storage stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications. The said transgenic plants synthesizing a modified starch are disclosed, for example, in EP 0 571 427, WO 1995/004826, EP 0 719 338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO 99/58688, WO 1999/58690, WO 1999/58654, WO 2000/008184, WO 2000/008185, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026 or WO 1997/20936.

2) transgenic plants which synthesize nonstarch carbohydrate polymers or which synthesize nonstarch carbohydrate polymers with altered properties in comparison to wild type plants without genetic modification. Examples are plants producing polyfructose, especially of the inulin and levan type, as disclosed in EP 0 663 956, WO 1996/001904, WO 1996/021023, WO 1998/039460 and WO 1999/024593, plants producing alpha-1,4-glucans as disclosed in WO 1995/031553, US 2002/031826, U.S. Pat. No. 6,284,479, U.S. Pat. No. 5,712,107, WO 1997/047806, WO 1997/047807, WO 1997/047808 and WO 2000/14249, plants producing alpha-1,6 branched alpha-1,4-glucans, as disclosed in WO 2000/73422, and plants producing alternan, as disclosed in WO 2000/047727, EP 06077301.7, U.S. Pat. No. 5,908,975 and EP 0 728 213.

3) transgenic plants which produce hyaluronan, as for example disclosed in WO 2006/032538, WO 2007/039314, WO 2007/039315, WO 2007/039316, JP 2006/304779 and WO 2005/012529.

Plants or plant cultivars (obtained by plant biotechnology methods, such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants, containing an altered form of cellulose synthase genes as described in WO 1998/000549,
b) plants, such as cotton plants, containing an altered form of rsw2 or rsw3 homologous nucleic acids as described in WO 2004/053219;
c) plants, such as cotton plants, with increased expression of sucrose phosphate synthase as described in WO 2001/017333;
d) plants, such as cotton plants, with increased expression of sucrose synthase as described in WO 02/45485;
e) plants, such as cotton plants, wherein the timing of the plasmodesmatal gating at the basis of the fibre cell is altered, e.g. through downregulation of fibre selective β-1,3-glucanase as described in WO 2005/017157;
f) plants, such as cotton plants, having fibres with altered reactivity, e.g. through the expression of N-acetylglucosamine transferase gene including nodC and chitin synthase genes as described in WO 2006/136351.

Plants or plant cultivars (obtained by plant biotechnology methods, such as genetic engineering) which may also be treated according to the invention are plants, such as oilseed rape or related Brassica plants, with altered oil profile characteristics. Such plants can be obtained by genetic transformation or by selection of plants containing a mutation imparting such altered oil characteristics and include:

a) plants, such as oilseed rape plants, producing oil having a high oleic acid content as described, e.g., in U.S. Pat. No. 5,969,169, U.S. Pat. No. 5,840,946, U.S. Pat. No. 6,323,392 or U.S. Pat. No. 6,063,947;
b) plants such as oilseed rape plants, producing oil having a low linolenic acid content as described in U.S. Pat. No. 6,270,828, U.S. Pat. No. 6,169,190 or U.S. Pat. No. 5,965,755;
c) plants such as oilseed rape plants, producing oil having a low level of saturated fatty acids as described, e.g., in U.S. Pat. No. 5,434,283.

Particularly useful transgenic plants which may be treated according to the invention are plants which comprise one or more genes which encode one or more toxins are the transgenic plants which are sold under the following trade names: YIELD GARD® (for example maize, cotton, soybeans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeafl (potato). Examples of herbicide-tolerant plants which may be mentioned are maize varieties, cotton varieties and soybean varieties which are sold under the following trade names: Roundup Ready® (tolerance to glyphosate, for example maize, cotton, soybean), Liberty Link® (tolerance to phosphinotricin, for example oilseed rape), IMI® (tolerance to imidazolinone) and SCS® (tolerance to sulphonylurea), for example maize. Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases from various national or regional regulatory agencies (see for example http://gmoinfo.jrc.it/gmp_browse.aspx and http://www.agbios.com/dbase.php).

EXAMPLE 1

Phaedon cochleariae

Test; (PHAECO Spray Application)

Solvent: 78.0 parts by weight of acetone
1.5 parts by weight of dimethylformamide
Emulsifier: 0.5 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration. Chinese cabbage (Brassica pekinesis) leaf-disks are sprayed with a preparation of the active ingredient of the desired concentration. Once dry, the leaf disks are infested with mustard beetle larvae (Phaedon cochleariae).

After 7 days mortality in % is determined. 100% means that all beetle larvae have been killed and 0% means that none of the beetle larvae have been killed.

EXAMPLE 2

Spodoptera frugiperda

Test (SPODFR Spray Application)

Solvent: 78.0 parts by weight acetone
1.5 parts by weight dimethylformamide
Emulsifier: 0.5 parts by weight alkylarylpolyglycolether To produce a suitable preparation of the active compound, 1 part by weight of active compound is mixed with the stated amount of solvent and emulsifier, and the concentrate is dilutes with emulsifier-containing water to the desired concentration. Maize (Zea mais) leaf sections are sprayed with a preparation of the active ingredient of the desired concentration. Once dry, the leaf sections are infested with fall armyworm larvae (Spodoptera frugiperda).

After 7 days mortality in % is determined. 100% means that all caterpillars have been killed and 0% means that none of the caterpillars have been killed.

EXAMPLE 3

*Myzus persicae*

Test; (MYZUPE Spray Application)

Solvent: 78.0 parts by weight acetone
1.5 parts by weight dimethylformamide
Emulsifier: 0.5 parts by weight alkylarylpolyglycolether To produce a suitable preparation of active compound, 1 part by weight of active compound is mixed with the stated amount of solvent and emulsifier, and the concentrate is diluted with emulsifier-containing water to the desired concentration. Chinese cabbage (*Brassica pekinesis*) leaf-disks infected with all instars of the green peach aphid (*Myzus persicae*), are sprayed with a preparation of the active ingredient at the desired concentration.

After 6 days mortality in % is determined. 100% means that all aphids have been killed; 0% means that none of the aphids have been killed.

EXAMPLE 4

*Meloidogyne* Test (MELGIN)

Solvent: 80.0 parts by weight of acetone

To produce a suitable preparation of active compound, 1 part by weight of active compound is mixed with the stated amount of solvent, and the concentrate is diluted with emulsifier-containing water to the desired concentration.

Vessels are filled with sand, a solution of the active ingredient, a suspension containing eggs and larvae of *Meloidogyne incognita* and salad seeds. The salade seeds germinate and the seedlings grow. Galls develop in the roots.

After 14 days the nematicidal activity is determined on the basis of the percentage of gall formation. 100% means that no galls were found; 0% means that the number of galls found on the roots of the treated plants was equal to that in untreated control plants.

EXAMPLE 5

*Tetranychus urticae*

Test; OP-Resistant (TETRUR Spray Application)

Solvent: 78.0 parts by weight acetone
1.5 parts by weight dimethylformamide
Emulsifier: 0.5 parts by weight alkylarylpolyglycolether To produce a suitable preparation of active compound, 1 part by weight of active compound is mixed with the stated amount of solvent and emulsifier, and the concentrate is diluted with emulsifier-containing water to the desired concentration. French beans (*Phaseolus vulgaris*) which are heavily infested with all stages of the two spotted spidermite (*Tetranychus urticae*), are sprayed with a preparation of the active ingredient at the desired concentration.

After 6 days mortality in % is determined. 100% means that all spider mites have been killed and 0% means that none of the spider mites have been killed.

| Substance | Object | Concentration | Efficacy % |
|---|---|---|---|
| Ex No. T 1 | PHAECO | 100 g/ha | 83 |
| | SPODFR | 500 g/ha | 100 |
| | MYZUPE | 500 g/ha | 90 |
| | TETRUR | 500 g/ha | 100 |
| | MELGIN | 20 ppm | 100 |
| Ex No. P 12 | PHAECO | 500 g/ha | 83 |
| | SPODFR | 500 g/ha | 100 |
| | MYZUPE | 500 g/ha | 90 |
| | TETRUR | 500 g/ha | 100 |

What is claimed is:

1. A method of controlling insects, pests or fungi, comprising applying to an insect, pest, fungus or a habitat thereof a compound of Formula (I)

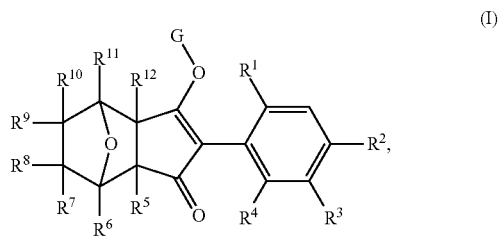

(I)

wherein
$R^1$ is methyl, ethyl, n-propyl, isopropyl, halomethyl, haloethyl, halogen, vinyl, ethynyl, methoxy, ethoxy, halomethoxy, haloethoxy or cyclopropyl,
$R^2$ is hydrogen or $C_1$-$C_6$alkyl,
$R^3$ is optionally substituted aryl, or optionally substituted heteroaryl,
$R^4$ is hydrogen, methyl, ethyl, n-propyl, isopropyl, halomethyl, haloethyl, halogen, vinyl, ethynyl, methoxy, ethoxy, halomethoxy or haloethoxy,
$R^5$ and $R^{12}$ are independently of each other hydrogen,
$R^7$, $R^8$, $R^9$, and $R^{10}$ are independently of each other hydrogen, or
$R^7$ and $R^8$ or $R^9$ and $R^{10}$, together with the carbon atoms to which they are attached form an alkenyl unit,
$R^6$ and $R^{11}$ are independently of each other hydrogen or an alkyl,
G represents hydrogen (a) or represents one of the groups

(b)

(c)

(d)

(e)

E or (f)

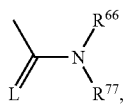
(g)

in which

E represents a metal ion or an ammonium ion,
L represents oxygen or sulphur,
M represents oxygen or sulphur,
$R^{22}$ represents optionally halogen- or cyano-substituted $C_2$-$C_{20}$-alkenyl, $C_1$-$C_8$-alkoxy-$C_2$-$C_8$-alkyl or poly-$C_1$-$C_8$-alkoxy-$C_2$-$C_8$-alkyl,
represents optionally halogen-, $C_1$-$C_6$-alkyl- or $C_1$-$C_6$-alkoxy-substituted $C_3$-$C_8$-cycloalkyl, or
represents optionally halogen-, cyano-, nitro-, $C_1$-$C_6$-alkyl-, $C_1$-$C_6$-alkoxy-, $C_1$-$C_6$-haloalkyl- or $C_1$-$C_6$-haloalkoxy-substituted phenyl or benzyl,
$R^{33}$ represents optionally halogen-substituted $C_1$-$C_8$-alkyl or optionally halogen-, $C_1$-$C_6$-alkyl-, $C_1$-$C_6$-alkoxy-, $C_1$-$C_4$-haloalkyl-, $C_1$-$C_4$-haloalkoxy-, cyano- or nitro-substituted phenyl or benzyl,
$R^{44}$ and $R^{55}$ independently of one another represent in each case optionally halogen-substituted $C_1$-$C_8$-alkyl, $C_1$-$C_8$-alkoxy, $C_1$-$C_8$-alkylamino, di($C_1$-$C_8$-alkyl)amino, $C_1$-$C_8$-alkylthio or $C_3$-$C_8$-alkenylthio, or represent in each case optionally halogen-, nitro-, cyano-, $C_1$-$C_4$-alkoxy-, $C_1$-$C_4$-haloalkoxy-, $C_1$-$C_4$-alkylthio-, $C_1$-$C_4$-halo-alkylthio-, $C_1$-$C_4$-alkyl- or $C_1$-$C_4$-haloalkyl-substituted phenyl, phenoxy or phenylthio, and
$R^{66}$ and $R^{77}$ independently of one another represent hydrogen, represent in each case optionally halogen- or cyano-substituted $C_1$-$C_8$-alkyl, $C_3$-$C_8$-cycloalkyl, $C_1$-$C_8$-alkoxy, $C_3$-$C_8$-alkenyl or $C_1$-$C_8$-alkoxy-$C_2$-$C_8$-alkyl, represent in each case optionally halogen-, $C_1$-$C_8$-alkyl-, $C_1$-$C_8$-haloalkyl- or $C_1$-$C_8$-alkoxy-substituted phenyl or benzyl, or together represent an optionally $C_1$-$C_6$-alkyl-substituted $C_3$-$C_6$-alkylene radical in which optionally one methylene group is replaced by oxygen or sulphur.

2. The method according to claim 1, wherein
$R^1$ is methyl, ethyl, vinyl, ethynyl, cyclopropyl, difluoromethoxy or trifluoromethoxy.

3. The method according to claim 1, wherein
$R^3$ is phenyl or phenyl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano, or is heteroaryl or heteroaryl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano.

4. The method according to claim 1, wherein
$R^4$ is hydrogen, methyl, ethyl, vinyl or ethynyl.

5. The method according to claim 1, wherein
$R^6$ and $R^{11}$ are independently of each other hydrogen, or
$R^6$ and $R^{11}$ are independently of each other $C_1$-$C_6$alkyl.

6. The method according to claim 1, wherein
$R^7$, $R^8$, $R^9$ and $R^{10}$ are independently of each other hydrogen.

7. The method according to claim 1, wherein
$R^2$ is $C_1$-$C_6$alkyl.

8. The method according to claim 7, wherein
$R^1$ is methyl, ethyl, vinyl, ethynyl, cyclopropyl, difluoromethoxy or trifluoromethoxy.

9. The method according to claim 7, wherein
$R^3$ is phenyl or phenyl substituted by $C_1$-$C_2$alkyl, $C_1$-$C_2$haloalkyl, $C_1$-$C_2$alkoxy, $C_1$-$C_2$haloalkoxy, fluoro, chloro, bromo or cyano, or is heteroaryl or heteroaryl substituted by $C_1$-$C_2$alkyl, $C_1$-$C_2$halo alkyl, $C_1$-$C_2$alkoxy, $C_1$-$C_2$haloalkoxy, fluoro, chloro, bromo or cyano.

10. The method according to claim 7, wherein
$R^4$ is hydrogen, methyl, ethyl, vinyl or ethynyl.

* * * * *